United States Patent
Schillebeeckx et al.

(10) Patent No.: US 11,742,058 B2
(45) Date of Patent: Aug. 29, 2023

(54) METHODS AND SYSTEMS OF PROCESSING COMPLEX DATA SETS USING ARTIFICIAL INTELLIGENCE AND DECONVOLUTION

(71) Applicant: Cofactor Genomics, Inc., St. Louis, MO (US)

(72) Inventors: Ian Schillebeeckx, San Francisco, CA (US); Jon R. Armstrong, San Diego, CA (US); Jeffrey Hiken, St. Louis, MO (US)

(73) Assignee: COFACTOR GENOMICS, INC., St. Louis, MO (US)

( * ) Notice: Subject to any disclaimer, the term of this patent is extended or adjusted under 35 U.S.C. 154(b) by 0 days.

(21) Appl. No.: 17/090,714

(22) Filed: Nov. 5, 2020

(65) Prior Publication Data

US 2021/0133592 A1    May 6, 2021

Related U.S. Application Data

(60) Provisional application No. 62/931,009, filed on Nov. 5, 2019.

(51) Int. Cl.

| | |
|---|---|
| *G16B 40/00* | (2019.01) |
| *G06N 3/126* | (2023.01) |
| *G06N 20/00* | (2019.01) |
| *G06N 3/086* | (2023.01) |
| *G06N 5/047* | (2023.01) |
| *G16B 25/10* | (2019.01) |
| *G06F 18/24* | (2023.01) |
| *G06F 18/213* | (2023.01) |
| *G06F 18/214* | (2023.01) |
| *G06V 10/764* | (2022.01) |
| *G06V 20/69* | (2022.01) |

(52) U.S. Cl.
CPC ........... *G16B 40/00* (2019.02); *G06F 18/213* (2023.01); *G06F 18/214* (2023.01); *G06F 18/24* (2023.01); *G06N 3/086* (2013.01); *G06N 3/126* (2013.01); *G06N 5/047* (2013.01); *G06N 20/00* (2019.01); *G06V 10/764* (2022.01); *G06V 20/695* (2022.01); *G16B 25/10* (2019.02); *C12Q 2600/136* (2013.01)

(58) Field of Classification Search
None
See application file for complete search history.

(56) References Cited

U.S. PATENT DOCUMENTS

| | | | |
|---|---|---|---|
| 10,636,512 B2 * | 4/2020 | Bloom | G16B 20/20 |
| 2012/0107798 A1 | 5/2012 | Santangelo | |
| 2014/0271674 A1 | 9/2014 | Dong et al. | |
| 2018/0023054 A1 | 1/2018 | Kang et al. | |
| 2018/0148717 A1 | 5/2018 | Armstrong et al. | |
| 2018/0357379 A1 | 12/2018 | Koh et al. | |
| 2019/0094223 A1 | 3/2019 | Shen-Orr et al. | |

FOREIGN PATENT DOCUMENTS

| | | | |
|---|---|---|---|
| WO | WO-2021092224 A1 | 5/2021 | |

OTHER PUBLICATIONS

Canale et al., CD39 Expression Defines Cell Exhaustion in Tumor-Infiltrating CD8 + T Cells. Cancer Res 78(1):115-128 (2018).
Cancer Genome Atlas Research Network. Comprehensive and Integrative Genomic Characterization of Hepatocellular Carcinoma. Cell 169(7):1327-1341.e23 (2017).
Gameiro et al., Treatment-naïve HPV+ head and neck cancers display a T-cell-inflamed phenotype distinct from their HPV-counterparts that has implications for immunotherapy. Oncoimmunology 7(10):e1498439 (2018).
Hanna et al., Frameshift events predict anti-PD-1/L1 response in head and neck cancer. JCI Insight 3(4):e98811 (2018).
Hu-Lieskovan et al., Tumor Characteristics Associated with Benefit from Pembrolizumab in Advanced Non-Small Cell Lung Cancer. Clin Cancer Res 25(16):5061-5068 (2019).
Lechner et al., Characterization of tumor-associated T-lymphocyte subsets and immune checkpoint molecules in head and neck squamous cell carcinoma. Oncotarget 8(27):44418-44433 (2017).
Meng et al., PD-L1 Expression Correlates With Tumor Infiltrating Lymphocytes and Response to Neoadjuvant Chemotherapy in Cervical Cancer. J Cancer 9(16): 2938-2945 (2018).
Riaz et al., Tumor and Microenvironment Evolution during Immunotherapy with Nivolumab. Cell 171(4):934-949 (2017).
Simoni et al., Bystander CD8 + T cells are abundant and phenotypically distinct in human tumour infiltrates. Nature 557(7706):575-579 (2018).
Thommen et al., A transcriptionally and functionally distinct PD-1 + CD8 + T cell pool with predictive potential in non-small-cell lung cancer treated with PD-1 blockade. Nat Med 24(7):994-1004 (2018).
Guo et al., Global characterization of T cells in non-small-cell lung cancer by single-cell sequencing. Nat Med 24(7):978-985 (2018).
PCT/US2020/059179 International Search Report and Written Opinion dated Mar. 30, 2021.

* cited by examiner

*Primary Examiner* — Nancy J Leith
(74) *Attorney, Agent, or Firm* — Wilson Sonsini Goodrich & Rosati

(57) ABSTRACT

Disclosed herein, are systems and methods for analyzing complex data signals using artificial intelligence and/or deconvolution algorithms to determine output pertaining to the state or status of one or more parameters. Data sets may include signals from various sources that can confound or distort the signals of interest. Accordingly, disclosed herein are deconvolution algorithms that enable the determination of the status of sources that correspond to the signals of interest.

22 Claims, 34 Drawing Sheets
(31 of 34 Drawing Sheet(s) Filed in Color)

METHODS AND SYSTEMS OF PROCESSING COMPLEX DATA SETS USING ARTIFICIAL INTELLIGENCE AND DECONVOLUTION

CROSS-REFERENCE

This application claims the benefit of U.S. Provisional Patent Application No. 62/931,009, filed Nov. 5, 2019, which is entirely incorporated herein by reference.

BACKGROUND

Cancer is a complex group of diseases involving abnormal cell growth with the potential to invade or spread to other parts of the body. Millions of new cases of cancer occur globally each year. Immune cells such as Tumor Infiltrating Lymphocytes (TILs) can detect and destroy tumors. Understanding the status of such immune cells may help with diagnosis and treatment. Heterogeneous tissue samples can give rise to complex data signals from which meaningful information is difficult to extract.

SUMMARY

Disclosed herein, in some embodiments, are systems and methods for analyzing complex data signals using artificial intelligence and/or deconvolution algorithms to determine output pertaining to the state or status of one or more parameters. Data sets may include signals from various sources that can confound or distort the signals of interest. Accordingly, disclosed herein are deconvolution algorithms that enable the determination of the status of sources that correspond to the signals of interest.

One aspect of the present disclosure is a computer-implemented system for complex signal deconvolution and status classification for a data set comprising a heterogeneous set of signals, the system comprising: (a) one or more processors; (b) a non-transitory computer readable storage medium encoded with instructions that cause the one or more processors to: (i) receive the data set comprising a heterogeneous set of signals, wherein the heterogeneous set of signals correspond to distinct signal sources: (ii) process the data set comprising the heterogeneous set of signals to generate a processed data set; (iii) analyze the processed data set using a machine learning deconvolution algorithm configured to deconvolve the heterogeneous set of signals to identify and quantify the distinct signal sources that correspond to the heterogeneous set of signals; and (iv) generate a status classification for the data set using a machine learning classifier based on analysis of at least on the identification and quantification of the distinct signal sources. In some embodiments, the machine learning deconvolution algorithm is configured to deconvolve at least 5 distinct signal sources that correspond to the heterogeneous set of signals. In some embodiments, the machine learning deconvolution algorithm identifies and quantifies the one or more distinct signal sources using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some embodiments, the machine learning classifier comprises a model comprising features generated using a feature selection technique. In some embodiments, the feature selection technique comprises one or more filters for evaluating feature relevance by examining data properties, wrappers that embed a model hypothesis within a feature subset search, or building into the classifier algorithm one or more embedded protocols that build a search for an optimal feature set. In some embodiments, the status classification is determined with an AUC of at least 0.8. In some embodiments, the data set comprises RNA-seq data. In some embodiments, the data set is derived from a cancer tissue sample. In some embodiments, the heterogeneous set of signals corresponds to immune expression signature genes for determining T cell state. In some embodiments, the distinct signal sources correspond to distinct cell populations corresponding to distinct cell states. In some embodiments, the distinct signal sources are identified and quantified as a percentage of total signal sources in the sample. In some embodiments, the status classification corresponds to responsiveness to a therapy.

Disclosed herein, in another aspect, is a computer-implemented method for complex signal deconvolution and status classification for a data set comprising a heterogeneous set of signals, the method comprising: (a) receive the data set comprising a heterogeneous set of signals, wherein the heterogeneous set of signals correspond to distinct signal sources: (b) process the data set comprising the heterogeneous set of signals to generate a processed data set; (c) analyze the processed data set using a machine learning deconvolution algorithm configured to deconvolve the heterogeneous set of signals to identify and quantify the distinct signal sources that correspond to the heterogeneous set of signals; and (d) generate a status classification for the data set using a machine learning classifier based on analysis of at least on the identification and quantification of the distinct signal sources. In some embodiments, the machine learning deconvolution algorithm is configured to deconvolve at least 5 distinct signal sources that correspond to the heterogeneous set of signals. In some embodiments, the machine learning deconvolution algorithm identifies and quantifies the one or more distinct signal sources using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some embodiments, the machine learning classifier comprises a model comprising features generated using a feature selection technique. In some embodiments, the feature selection technique comprises one or more filters for evaluating feature relevance by examining data properties, wrappers that embed a model hypothesis within a feature subset search, or building into the classifier algorithm one or more embedded protocols that build a search for an optimal feature set. In some embodiments, the status classification is determined with an AUC of at least 0.8. In some embodiments, the data set comprises RNA-seq data. In some embodiments, the data set is derived from a cancer tissue sample. In some embodiments, the heterogeneous set of signals corresponds to immune expression signature genes for determining T cell state. In some embodiments, the distinct signal sources correspond to distinct cell populations corresponding to distinct cell states. In some embodiments, the distinct signal sources are identified and quantified as a percentage of total signal sources in the sample. In some embodiments, the status classification corresponds to responsiveness to a therapy.

Another aspect of the present disclosure provides a method of optimizing an immunotherapy regimen, the method comprising: (a) obtaining RNA sequencing data from a sample obtained from a subject being treated with an immunotherapy regimen: (b) applying a deconvolution algorithm to at least a subset of the RNA sequencing data to identify and quantify an amount or percentage of exhausted T-cells in the sample based on expression levels of one or more cell status signature genes; (c) determining if the sample displays an elevated level of exhausted T-cells; and i) recommending an alternative therapy based on a determination that the sample has an elevated level of exhausted T-cells in (c); or (ii) recommending continuing with the immunotherapy regimen based on a determination that the sample does not have an elevated level of exhausted T-cells. In some instances, the immunotherapy regimen comprises an immune cell therapy, a cancer vaccine, a cytokine therapy, an antibody therapy, or any combination thereof. In some instances, the antibody therapy comprises tumor targeting monoclonal antibodies, immune cell activating antibodies, or a combination thereof. In some instances, the immune cell therapy comprises chimeric antigen receptor T-cell (CAR-T) therapy. In some instances, the immunotherapy regimen comprises an active immunotherapy, a passive immunotherapy, or a combination thereof. In some instances, the elevated level of exhausted T-cells is at least 50% of the T-cells of the sample. In some instances, the elevated level of exhausted T-cells indicates the subject will not respond to the immunotherapy regimen. In some instances, the elevated level of exhausted T-cells indicates the subject is not responding to the immunotherapy regimen. In some instances, the elevated level of exhausted T-cells indicates the immunotherapy regimen is ineffective. In some instances, the elevated level of exhausted T-cells indicates the immunotherapy regimen has lost efficacy. In some instances, applying the deconvolution algorithm further identifies or quantifies an amount or percentage of activated T-cells in the sample. In some instances, the method further comprises recommending the alternative therapy if the sample displays a low level of activated T-cells. In some instances, the low level of activated T-cells comprises 20% or less of the T-cells of the sample. In some instances, the alternative therapy comprises chemotherapy, radiation therapy, surgery, or any combination thereof. In some instances, the alternative therapy is an additional immunotherapy. In some instances, the alternative therapy is a non-immunotherapy. In some instances, the T-cells comprise CD4+ cells, CD8+ cells, Natural Killer T-Cells (NKT), or any combination thereof. In some instances, the one or more cell status signature genes comprise one or more genes selected from Table 1. In some instances, the deconvolution algorithm applies a deconvolution matrix to the RNA sequencing data to quantify the T-cells having a particular status. In some instances, the deconvolution matrix comprises a plurality of cell status signature genes. In some instances, the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some instances, the one or more cell status signature genes comprises at least 100 cell status signature genes. In some instances, the one or more cell status signature genes comprises at least 10 cell status signature genes. In some instances, the one or more exhaustion status signature genes have a bimodal expression signature between at least two different cell statuses with no more than a 50% overlap between modes. In some instances, the deconvolution algorithm requires no more than 100 cell status signature genes to identify and quantify the amount or percentage of T-cells in the sample having a particular status with a 90% accuracy for 100 independent samples. In some instances, wherein (a) comprises obtaining RNA molecules from the sample and measuring the level of gene expression on the RNA molecules. In some instances, (a) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances, (a) comprises performing next generation RNA sequencing on a cDNA library generated from the sample. In some instances, the sample is a tumor biopsy. In some instances, the sample is at least one formalin-fixed paraffin-embedded (FFPE) curl. In some instances, wherein the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the immunotherapy regimen is a cancer vaccine, cytokine therapy, immune cell therapy, antibody therapy, or a combination thereof. In some instances, the immunotherapy regimen is chimeric antigen receptor T-cell (CAR-T) therapy. In some instances, the method further comprises the step of determining or predicting the effectiveness of the immunotherapy regimen based on the identification and quantification of the amount or percentage of T-cells having an exhausted status. In some instances, determining or predicting the effectiveness of the immunotherapy regimen comprises determining a ratio of activated:exhausted T-cells in the sample. In some instances, the method further comprises the step of applying a second deconvolution algorithm to at least a second subset of the RNA sequencing data to identify and quantify one or more T-cell subtypes that are present in the sample based on expression levels of one or more expression signature genes. In some instances, the method further comprises analyzing at least a subset of the RNA sequencing data to determine level of gene expression for at least one immune modulatory gene.

Another aspect of the present disclosure provides a method for treating a subject, the method comprising: (a) administering an immunotherapy regimen to a subject in need thereof; (b) obtaining a sample from the subject; (c) sending the sample for analysis of cell status, wherein the analysis of cell status comprises. (i) generating RNA sequencing data from the sample; and (ii) applying a deconvolution algorithm to at least a subset of the RNA sequencing data to identify and quantify an amount or percentage of cells in the sample having one or more cell statuses based on expression levels of one or more cell status signature genes; and (d) determining if the immunotherapy regimen is effective based on the identity and quantity of the one or more cell statuses. In some instances, analysis of cell status measures the status of at least one immune cell type. In some instances, the at least one immune cell type is selected from T-cells, natural killer (NK) cells, B-cells, macrophages, and plasma cells. In some instances, the at least one immune cell type is selected from the group consisting of CD4+ memory T-cells, CD4+ naive T-cells, CD4+ T-cells, central memory T (Tcm) cells, effector memory T (Tem) cells, CD4+ Tcm, CD4+ Tem. CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the at least one immune cell type is selected from the group consisting of M1 macrophages, M2 macrophages, CD19+ B cells, CD14+ monocytes, CD56+ NK cells, CD8+ T cells, Treg cells, and CD4+ T cells. In some instances, the at least one immune cell type comprises T-cells. In some instances, the T-cells comprise CD8+ cells, CD4+ cells, or a combination thereof. In some instances, the one or more cell statuses comprises naïve status, activated status, activation recovered status, terminally exhausted status, progenitor exhausted stats, central memory status, effector memory status, stem cell memory status or any combination thereof. In some instances, the one or more cell statuses comprises exhausted status. In some instances, the immunotherapy regimen comprises an immune cell therapy, a cancer vaccine, a cytokine therapy, an antibody therapy, or any combination thereof. In some instances, the antibody therapy comprises tumor targeting monoclonal antibodies, immune cell activating antibodies, or a combination thereof. In some instances, the immune cell therapy comprises chimeric antigen receptor T-cell (CAR-T) therapy. In some instances, the immunotherapy regimen comprises an active immunotherapy, a passive immunotherapy, or a combination thereof. In some instances, determining if the immunotherapy regimen is effective based on the identity and quantity of the one or more cell statuses comprises comparing the quantity of cells having a particular cell status to a predetermined threshold for the particular cell status. In some instances, the particular cell status is exhaustion. In some instances, the predetermined threshold is at least 50% of the cells. In some instances, the method further comprises (e) administering an alternative therapy if the immunotherapy is determined to be ineffective. In some instances, the alternative therapy comprises chemotherapy, radiation therapy, surgery, or any combination thereof. In some instances, the alternative therapy is an additional immunotherapy. In some instances, the alternative therapy is a non-immunotherapy. In some instances, the one or more cell status signature genes comprise one or more genes selected from Table 1. In some instances, the deconvolution algorithm applies a deconvolution matrix to the RNA sequencing data to quantify the T-cells having a particular status. In some instances, the deconvolution matrix comprises a plurality of cell status signature genes. In some instances, the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some instances, the one or more cell status signature genes comprises at least 100 cell status signature genes. In some instances, the one or more cell status signature genes comprises at least 10 cell status signature genes. In some instances, the one or more cell status signature genes have a bimodal expression signature between at least two different cell statuses with no more than a 50% overlap between modes. In some instances, the deconvolution algorithm requires no more than 100 cell status signature genes to identify and quantify the amount or percentage of T-cells in the sample having a particular status with a 90% accuracy for 100 independent samples. In some instances, (i) comprises obtaining RNA molecules from the sample and measuring the level of gene expression on the RNA molecules. In some instances, (i) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances, (i) comprises performing next generation RNA sequencing on a cDNA library generated from the sample. In some instances, the sample is a tumor biopsy. In some instances, wherein the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the analysis of cell status further comprises the step of applying a second deconvolution algorithm to at least a second subset of the RNA sequencing data to identify and quantify one or more T-cell subtypes that are present in the sample based on expression levels of one or more expression signature genes. In some instances, the analysis of cell status further comprises the step of comprising analyzing at least a subset of the RNA sequencing data to determine level of gene expression for at least one immune modulatory gene.

Another aspect of the present disclosure provides a method of preparing an immune cell therapy, the method comprising: (a) obtaining immune cells derived from a subject in need immune cell therapy: (b) assessing the status of the immune cells by (i) generating RNA sequencing data from a subset of the immune cells; and (ii) applying a deconvolution algorithm to at least a subset of the RNA sequencing data to identify and quantify an amount or percentage of immune cells in the sample having at least one particular status based on expression levels of one or more cell status signature genes; and (c) activating the immune cells to target cancerous tissue in the subject. In some instances, step (b) is performed multiple times. In some instances, step (b) is performed at a plurality of time points in the process. In some instances, step (b) is performed at least prior to activating the immune cells. In some instances, step (b) is performed at least once after activating the immune cells. In some instances, step (b) is performed multiple times after activating the immune cells. In some instances, the at least one particular status comprises naïve status, activated status, activation recovered status, terminally exhausted status, progenitor exhausted status, central memory status, effector memory status, stem cell memory status or any combination thereof. In some instances, the method further comprises predicting the efficacy of the immune cell therapy based on the identity and quantity of immune cells having at least one particular status. In some instances, predicting the efficacy of the immune cell therapy comprises comparing the identity and quantity of immune cells having at least one particular status to a reference. In some instances, the at least one particular status compared to the reference comprises an exhaustion status. In some instances, the at least one particular status compared to the reference comprises an activated status. In some instances, the at least one particular status compared to the reference comprises a naïve status. In some instances, the efficacy is predicted based on the identity and quantity of immune cells having a particular status prior to activating the immune cells. In some instances, the efficacy is predicted based on the identity and quantity of immune cells having a particular status after activation. In some instances, the immune cells comprise T-cells, natural killer (NK) cells, B-cells, macrophages, plasma cells, or any combination thereof. In some instances, the immune cells comprise CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, plasma cells, or any combination thereof. In some instances, the immune cells comprise M1 macrophages, M2 macrophages, CD19+ B cells, CD14+ monocytes, CD56+ NK cells, CD8+ T cells, Treg cells, CD4+ T cells, or any combination thereof. In some instances, the immune cells comprise CD8+ cells, CD4+ cells, or a combination thereof. In some instances, the immune cell therapy is chimeric antigen receptor T-cell (CAR-T) therapy, tumor-infiltrating lymphocyte (TIL) therapy, engineered T-cell receptor (TCR) therapy, or natural killer (NK) cell therapy. In some instances, the immune cell therapy is CAR-T therapy. In some instances, the CAR-T therapy is a CD19-targeting CAR-T cell therapy. In some instances, the CAR-T therapy is axicabtagene ciloleucel or tisagenlecleucel. In some instances, activating the immune cells comprises, inserting a chimeric antigen receptor gene into the immune cells. In some instances, activating the immune cells comprises inserting an engineered T-cell receptor gene into the immune cells. In some instances, activating the immune cells comprises incubating the immune cells with a tumor cell antigen. In some instances, the method further comprises proliferating the immune cells. In some instances, the method further comprises identifying an optimal dosing status of the immune cells. In some instances, the optimal dosing status is determined by comparing the amount or percentage of immune cells in the sample having at least one particular status to a reference. In some instances, the method further comprises comprising administering the immune cells to the subject. In some instances, the one or more cell status signature genes comprise one or more genes selected from Table 1. In some instances, the deconvolution algorithm applies a deconvolution matrix to the RNA sequencing data to quantify the immune cells having a particular status. In some instances, the deconvolution matrix comprises a plurality of cell status signature genes. In some instances, the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some instances, the one or more cell status signature genes comprises at least 100 exhaustion status signature genes. In some instances, the one or more cell status signature genes comprises at least 10 exhaustion status signature genes. In some instances, the one or more exhaustion status signature genes have a bimodal expression signature between at least two different cell statuses with no more than a 50% overlap between modes. In some instances, the deconvolution algorithm requires no more than 100 cell status signature genes to identify and quantify the amount or percentage of T-cells in the sample having a particular status with a 90% accuracy for 100 independent samples. In some instances, (i) comprises obtaining RNA molecules from the sample and measuring the level of gene expression on the RNA molecules. In some instances, (i) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances, (a) comprises performing next generation RNA sequencing on a cDNA library generated from the sample. In some instances, the sample is a tumor biopsy. In some instances, the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer.

Another aspect of the present disclosure provides a method for processing data to determine cellular status, the method comprising: (a) obtaining RNA sequencing data from a sample obtained from a subject; and (b) applying a deconvolution algorithm to at least a subset of the RNA sequencing data to identify and quantify an amount or percentage of T-cells in the sample having a particular status based on expression levels of one or more cell status signature genes. In some instances, the particular status of the T-cells comprises naïve status, activated status, activation recovered status, terminally exhausted status, progenitor exhausted status, central memory status, effector memory status, stem cell memory status, or any combination thereof. In some instances, the T-cells comprise CD4+ cells, CD8+ cells, Natural Killer T-Cells (NKT), or any combination thereof. In some instances, the one or more cell status signature genes comprise one or more genes selected from Table 1. In some instances, the deconvolution algorithm applies a deconvolution matrix to the RNA sequencing data to quantify the T-cells having a particular status. In some instances, the deconvolution matrix comprises a plurality of cell status signature genes. In some instances, the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. In some instances, the one or more cell status signature genes comprises at least 100 cell status signature genes. In some instances, the one or more cell status signature genes comprises at least 10 cell status signature genes. In some instances, the one or more cell status signature genes have a bimodal expression signature between at least two different cell statuses with no more than a 50% overlap between modes. In some instances, the deconvolution algorithm requires no more than 100 cell status signature genes to identify and quantify the amount or percentage of T-cells in the sample having a particular status with a 90% accuracy for 100 independent samples. In some instances, (a) comprises obtaining RNA molecules from the sample and measuring the level of gene expression on the RNA molecules. In some instances, (a) comprises obtaining RNA molecules from the sample and performing reverse transcription polymerase chain reaction on the RNA molecules to generate complementary deoxyribonucleic acid (cDNA) molecules, and sequencing the cDNA molecules. In some instances, the cDNA molecules are tagged with unique molecular identifiers and amplified by polymerase chain reaction prior to sequencing. In some instances. (a) comprises performing next generation RNA sequencing on a cDNA library generated from the sample. In some instances, the sample is a tumor biopsy. In some instances, the sample is at least one formalin-fixed paraffin-embedded (FFPE) curl. In some instances, the sample has an RNA integrity number (RIN) of no more than 6.0. In some instances, the sample has an RNA integrity number (RIN) of no more than 2.0. In some instances, the sample comprises RNA molecules at least 200 nucleotides in size that constitute no more than 90% of total RNA in the sample. In some instances, the sample comprises RNA molecules at least 200 nucleotides in size that constitute no more than 60% of total RNA in the sample. In some instances, the sample comprises RNA molecules at least 200 nucleotides in size that constitute no more than 30% of total RNA in the sample. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the subject has cancer. In some instances, the subject has received an immunotherapy regimen. In some instances, the immunotherapy regimen is a cancer vaccine, cytokine therapy, immune cell therapy, antibody therapy, or a combination thereof. In some instances, the immunotherapy regimen is chimeric antigen receptor T-cell (CAR-T) therapy. In some instances, the method further comprises the step of determining or predicting the effectiveness of the immunotherapy regimen based on the identification and quantification of the amount or percentage of T-cells having a particular status. In some instances, determining or predicting the effectiveness of the immunotherapy regimen comprises determining a ratio of activated:exhausted T-cells in the sample. In some instances, the immunotherapy regiment is determined or predicted to be effective if at most 10% of T-cells in the sample are exhausted. In some instances, the method further comprises the step of applying a second deconvolution algorithm to at least a second subset of the RNA sequencing data to identify and quantify one or more T-cell subtypes that are present in the sample based on expression levels of one or more expression signature genes. In some instances, the method further comprises the step of analyzing at least a subset of the RNA sequencing data to determine level of gene expression for at least one immune modulatory gene.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
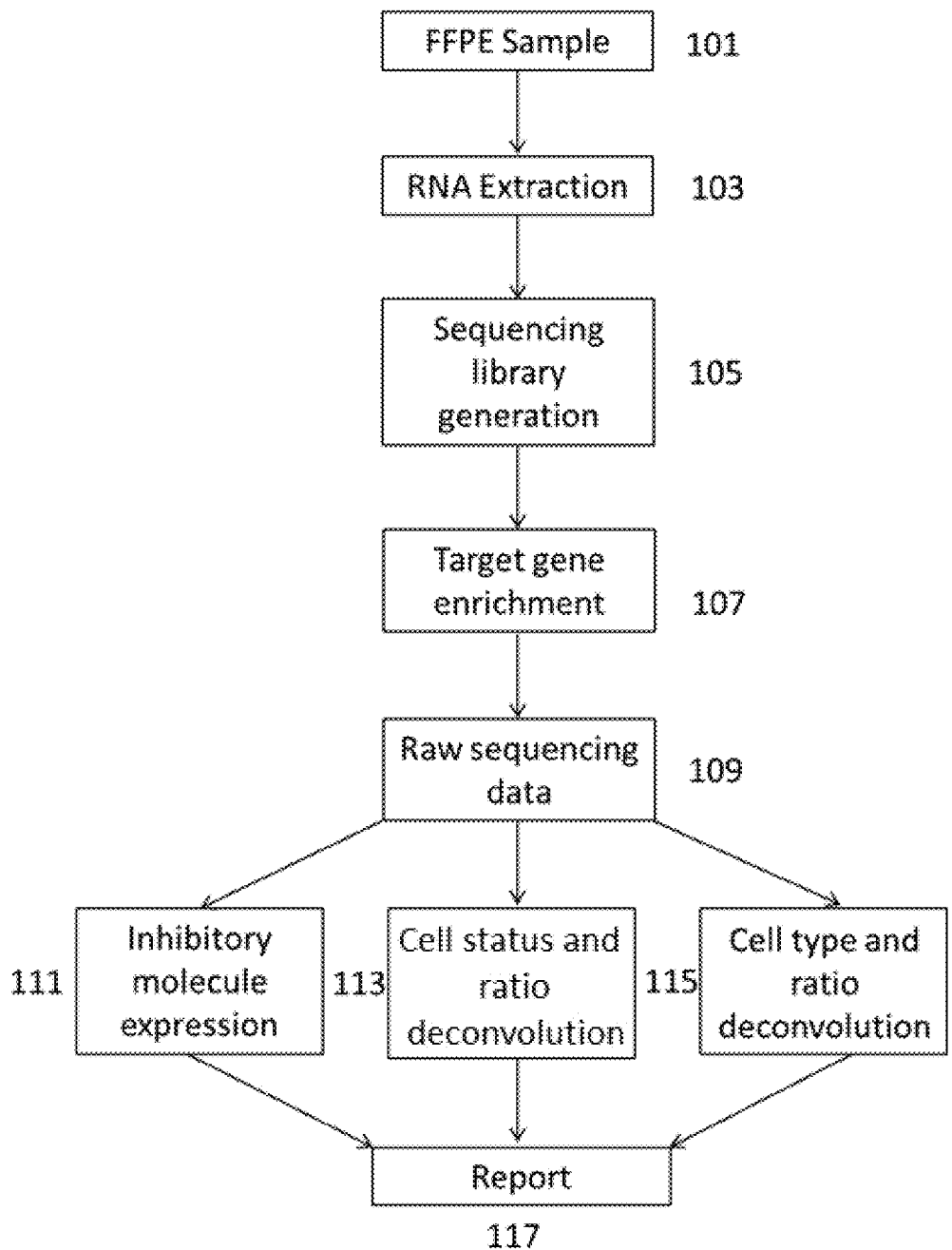
FIG. 1 depicts an example workflow for characterization of immune cell status in a tumor microenvironment.

Disclosed herein, in some embodiments, are systems and methods for analyzing complex data signals using artificial intelligence and/or deconvolution algorithms to determine output pertaining to the state or status of one or more parameters. Data sets may include signals from various sources that can confound or distort the signals of interest. Accordingly, disclosed herein are deconvolution algorithms that enable the determination of the status of sources that correspond to the signals of interest.

Provided herein are systems and methods for determining cellular status using gene expression data. Cellular state or status (used interchangeable herein) refers to a physiological condition of a given cell that defines certain characteristics of the cell. In some instances, cellular state or status refers to a degree of functional differentiation of a cell, for example an immune cell being "naïve" or "activated." In some instances, it may be possible to determine the state or status of a cell given the levels of expression of various genes with the cell. The cell status can be determined using deconvolution algorithms or models including machine learning algorithms. The cellular status information can be used to diagnose or predict treatment outcomes for a subject. The expression information can be next generation RNA sequencing data. In some cases, the samples are FFPE samples.

Provided herein is a method called T Cell State Profiling (TCSP) that characterizes the transient nature of T cells, or T Cell States (TCSs), in FFPE specimens using five RNA models. These TCS RNA models are created using functional methods, and robustly discriminate between Naïve, Activated, Exhausted, Effector Memory, and Central Memory TCSs, without the reliance on non-specific, classical markers. TCSP is analytically valid and corroborates associations between TCSs and clinical outcomes.

Naïve T cells are those which have not encountered cognate antigen via the T cell receptor and a costimulatory molecule. In response to stimuli such as a virus or nascent tumor, Naïve T cells become activated. Activated T cells are associated with expression of effector proteins such as IL-2 and IFN-γ and are most directly responsible for the T cell clearance of an infection or cancer. In addition, activation results in a transient increase in expression of checkpoint proteins such as PD-1, TIM3, and LAG3. As the infection or tumor is cleared, most T cells will undergo apoptosis or be cleared by other immune cells, but a subset will differentiate into T cell subsets including Effector Memory (EM) and Central Memory (CM) cells. These two classes of T cells serve to guard against future infection. EM T cells have little or no proliferative ability but have a rapid effector cytotoxic response to recognized antigens from previous infections or tumors. CM T cells likewise recognize antigens from previous infections or tumors but are more abundant in secondary lymphoid tissues than the periphery. They serve as a reservoir to expand the effector T cell population upon recognition of an antigen. Finally, in the case of an ongoing infection or tumor, i.e., long-term, continuous antigen stimulation. Activated T cells become Exhausted. Exhausted T cells are often found in sites of chronic viral infections and tumors. They are characterized by sustained expression of checkpoint inhibitors such as PD-1, TIM3, and LAG3, diminished effector function, and loss of proliferative ability. As a result, exhausted T cells have a greatly decreased ability to fight infections or tumors.

The abundance of these five TCSs—Naïve, Activated, EM, CM, and Exhausted—in isolation, have offered insights into the status of the immune response to an infection or solid tumor and ultimately response to a particular therapy, such as an immunotherapy.

One such therapy which my benefit from increased knowledge of TSCs a checkpoint inhibitor therapy, such as anti-PD-1 therapy. Anti-PD-1 therapy can provide long, durable benefit to a fraction of patients. However, existing FDA approved PD-L1 test does not accurately predict response For instance, response to anti-PD1 therapy is associated with higher levels of EM cells in Head and Neck Squamous Cell Carcinoma (HNSCC). PD-1 inhibits effector function upon ligand binding and is expressed in Activated and Exhausted T cells, yet paradoxically has been associated with response in Non-small Cell Lung Cancer (NSCLC). In addition, Exhausted T Cells are an important component of the anti-tumor immune response following PD-1 or CTLA-4 blockade in several cancers. These works suggest that the more nuanced and comprehensive characterization of TCS might more successfully predict anti-PD-1 response.

Anti-PD-1 therapies are an increasingly important treatment option across many cancer types. Anti-PD-1 therapy and other checkpoint inhibitors are approved for the treatment of 14 cancer types, making around 39% of all cancer patients eligible for checkpoint therapy. Unfortunately, only approximately 11% of all cancer patients benefit from anti-PD-1 therapies. However, among patients who respond to anti-PD-1 therapy, many experience a robust, durable response even in cancers with historically poor long-term survival. Biomarkers aim to predict which patients will respond to anti-PD-1 treatment, unlocking the improved outcomes, reduced costs, and more efficient treatments promised by precision medicine. The most commonly used biomarker for anti-PD-1 therapies is PD-L1 expression measured by IHC. PD-L1 is the ligand for the PD-1 receptor and a target of checkpoint inhibitors in its own right. Unfortunately, PD-L1 is an unreliable biomarker for predicting response. In fact, across 10 solid tumor types, PD-L1 IHC prediction of clinical response has a Receiver Operating Characteristic (ROC) Area Under the Curve (AUC) of just 0.65, where an AUC of 1 represents perfect prediction and AUC of 0.5 represents random chance.

Although the PD-L1 molecule is involved in the mechanism of action of anti-PD-1 therapies, other characteristics of the adaptive immunity, namely T cells, may be more useful in predicting response. T cells are broadly divided into two classes, CD4-positive and CD8-positive. However, T cells can also be classified according to their activation and differentiation states, which capture the activity, antigen-exposure, and specific role of a T cell population. These states are dynamic states, as T cells and their progeny can progress from one state to another over the course of an adaptive immune response, with each state providing a snapshot of the T cell response to an infection or cancer. In particular, five T cell states (TCSs)—Naïve, Activated. Effector Memory (EM), Central Memory (CM), and Exhausted—are more descriptive of the immunogenic status of T cell adaptive immune response and thus potentially more useful in predicting a patient's response to anti-PD-1 therapy.

Provided herein is a biomarker platform using measurements of these five TCSs in patient tumors. Typically. TCSs are characterized using functional assays or flow cytometry, two methods which are difficult or impossible to perform routinely on common clinical specimens namely, formalin fixed and paraffin embedded (FFPE) tissues. RNA gene-expression biomarkers are feasible in these samples and have found clinical utility with commercial tests such as Oncotype DX, Veracyte Affirma, and Agendia MammaPrint. In addition, substantial RNA-seq datasets are available for validating RNA-based biomarkers. Therefore, we used bulk RNA-seq data to develop and validate novel RNA models for estimating five TCSs in FFPE tumor samples. These TCS models are a type of Health Expression Model which has been described previously. The TCS models were used to characterize infiltrating cells in HNSCC, NSCLC, Melanoma, and other cancers across the Cancer Genome Atlas Program (TCGA). In line with Predictive Immune Modeling, we used machine-learning to build multianalyte biomarkers from the TCS model readouts. These biomarkers predicted response to anti-PD-1 therapies in HNSCC, NSCLC, and Melanoma, and out-performed the clinically indicated PD-L1 test.

Also provided herein, multianalyte biomarkers based on TCSP estimates predicted response to anti-PD-1 therapy in three different cancers and outperformed the indicated PD-L1 test, as well as Tumor Mutational Burden. Given the utility of TCSP, we have investigated herein the TCS of TCGA cancers.

The TCSP described herein is a novel way to characterize T cells. Characterizing the five TCSs in FFPE patient samples enables new opportunities for researching the tumor-immune microenvironment, studying response to immunotherapies, and developing biomarkers to predict patient response to treatment. TCS models were designed to be specific to each TCS, allowing one to discriminate between TCSs in heterogeneous FFPE tumor samples rather than relying on commonly used non-specific markers (e.g., PD-1 as a marker for exhaustion).

Figure 11A:
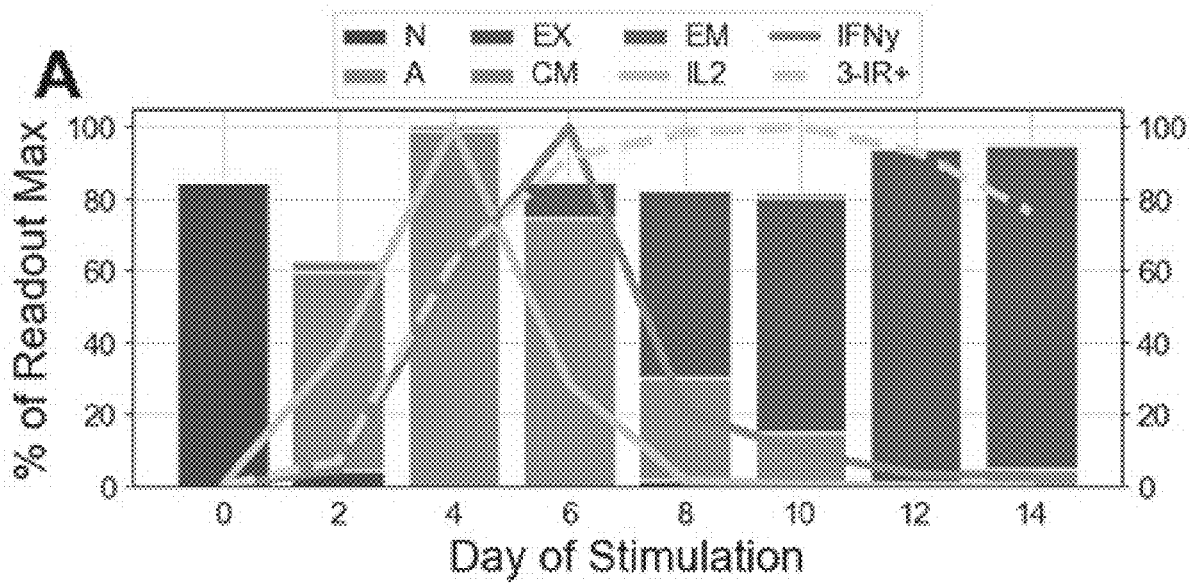
FIG. 11A shows T Cell state profiling results, specifically the transient change of T Cell State of Naïve CD8+ T cells in a chronic stimulation in vitro model.
Figure 14A:
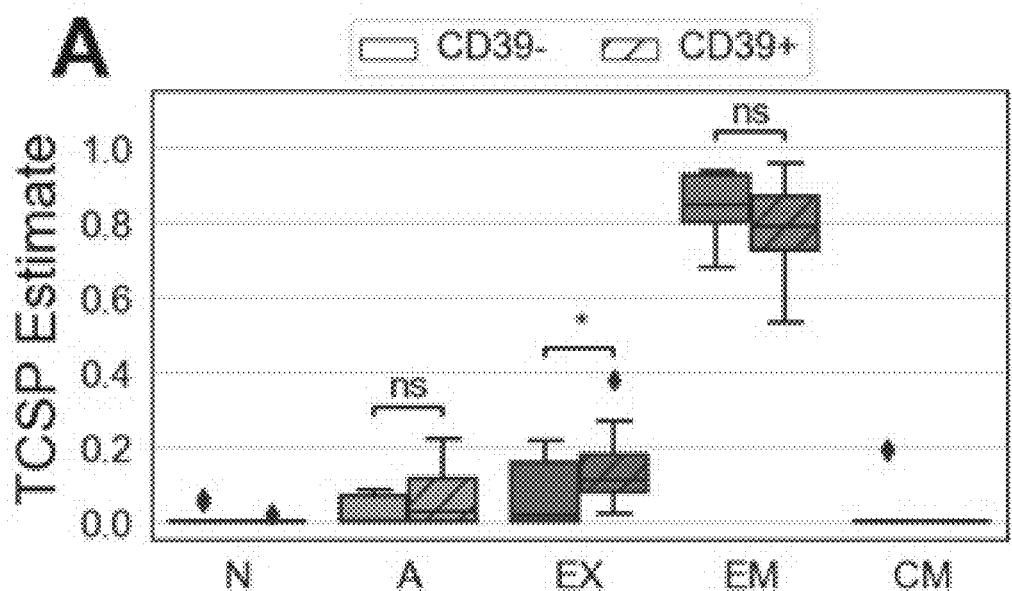
FIG. 14A shows sum-normalized T Cell State estimates for CD39− (n=11) and CD39+(n=12) CD8+ T cells isolated from Non-small Cell Lung Cancer (NSCLC) and Colorectal Cancer (CRC) tumors. The distribution of estimates per group is shown as a box and whisker. The box represents the $1^{st}$ and $3^{rd}$ quartiles, while the center line represents the median. The whiskers encompass 1.5 times past the $1^{st}$ and $3^{rd}$ interquartiles and points outside this range are shown as diamonds. N, Naïve state model; A, Activated state model; EX. Exhausted state model: EM, Effector Memory state model; CM, Central Memory state model.
Figure 14B:
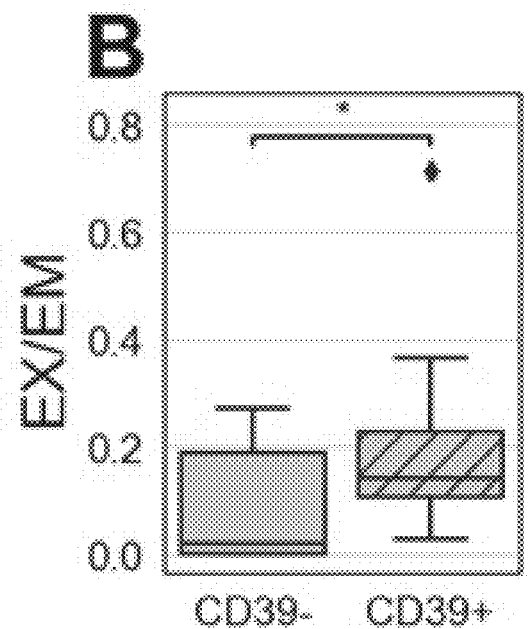
FIG. 14B shows composite exhaustion level for CD39− and CD39+ isolates. The composite level is calculated as Exhaustion divided by EM.
Figure 14D:
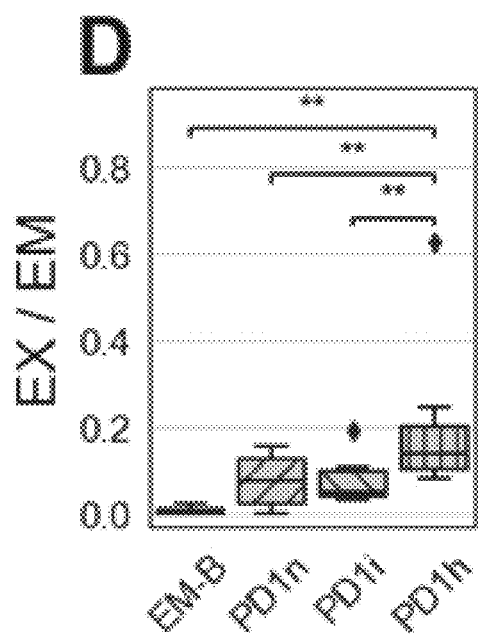
FIG. 14D shows composite exhaustion level for the same isolates as FIG. 14C. The composite level is calculated the same as FIG. 14B.
Figure 15A:
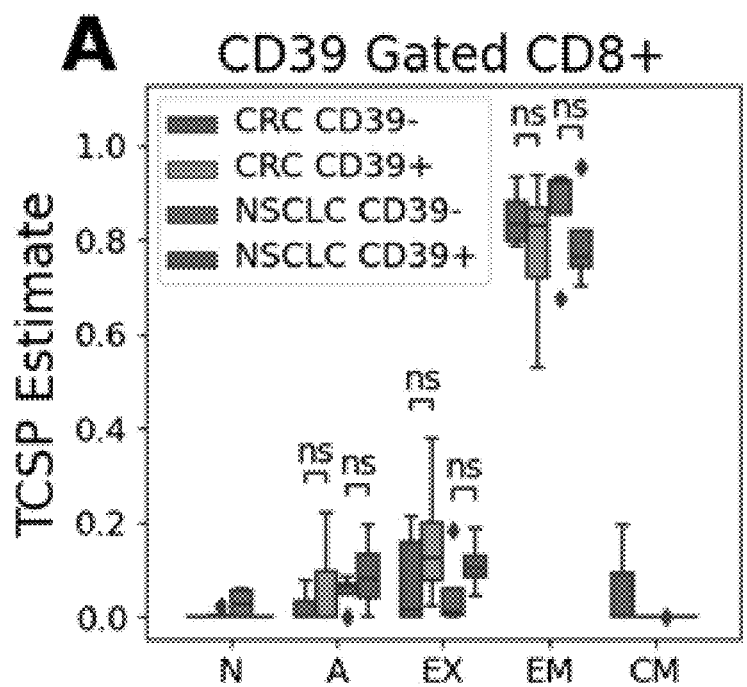
FIG. 15A shows sum-normalized T Cell State estimates for CD39− and CD39+CD8+ T cells isolated from Non-small Cell Lung Cancer (NSCLC, n=4/m=4) and Colorectal Cancer (CRC, n=7/m=8) tumors. In both NSCLC and CRC, the alternative hypothesis is that Activation and Exhaustion are higher in CD39+ isolates, while EM is lower in CD39+ isolates. N, Naïve state model; A, Activated state model; EX, Exhausted state model: EM, Effector Memory state model: CM, Central Memory state model.
Figure 15B:
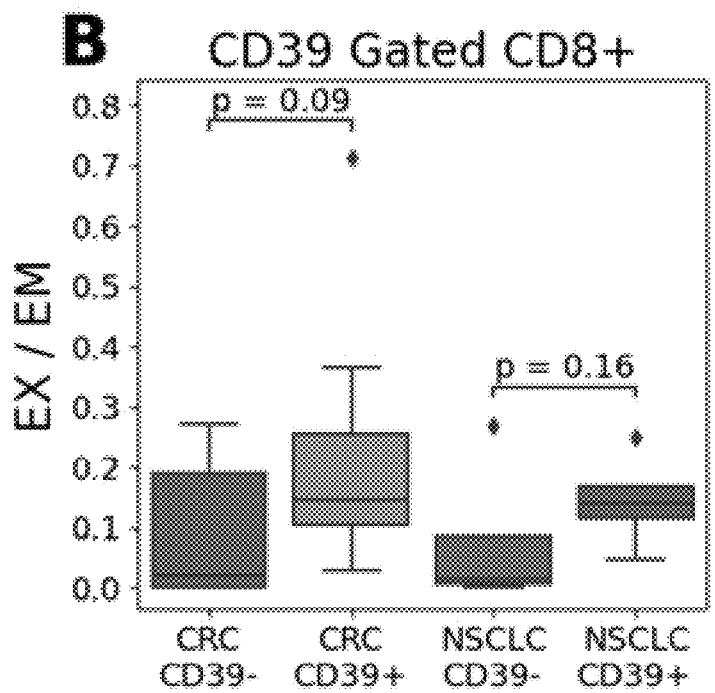
FIG. 15B shows composite exhaustion level for CD39− and CD39+ isolates from FIG. 15A. The composite level is calculated as Exhaustion divided by EM. In both NSCLC and CRC, the alternative hypothesis is that the composite exhaustion level is larger in CD39+ isolates.
Figure 15C:
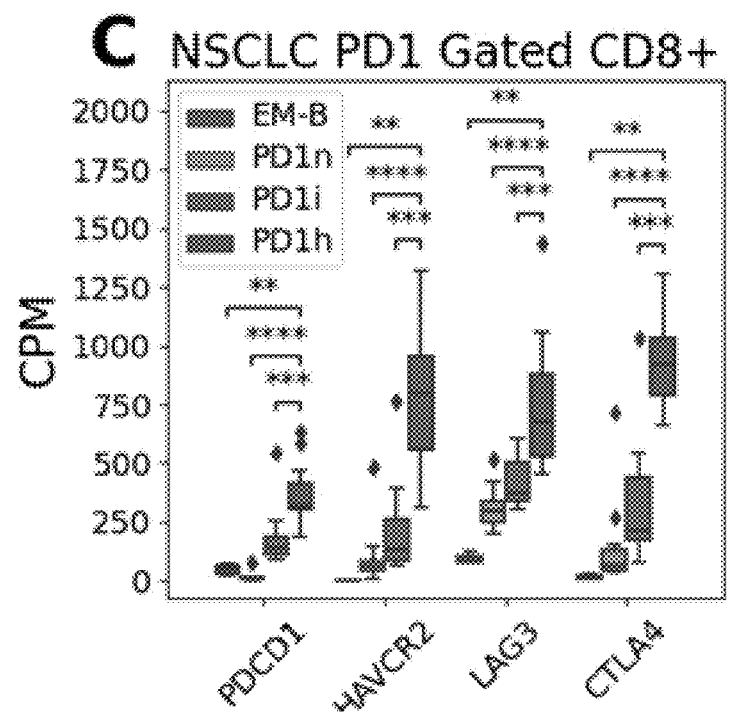
FIG. 15C gene expression of exhaustion associated inhibitory receptors for CD8+ T cell isolates sorted by varying levels of PD1 expression. EM CD8+ T cells isolated from blood (EM-B, n=4) were compared against CD8+ T cells isolated from NSCLC tumors with no PD1 (PD1n, n=11), intermediate PD1 (PD1i, n=11), and high PD1 (PD1h, n=11) expression. For each gene, expression of PD1h isolates are hypothesized to be larger than EM-B, PD1n, and PD1i, respectively.
Figure 15D:
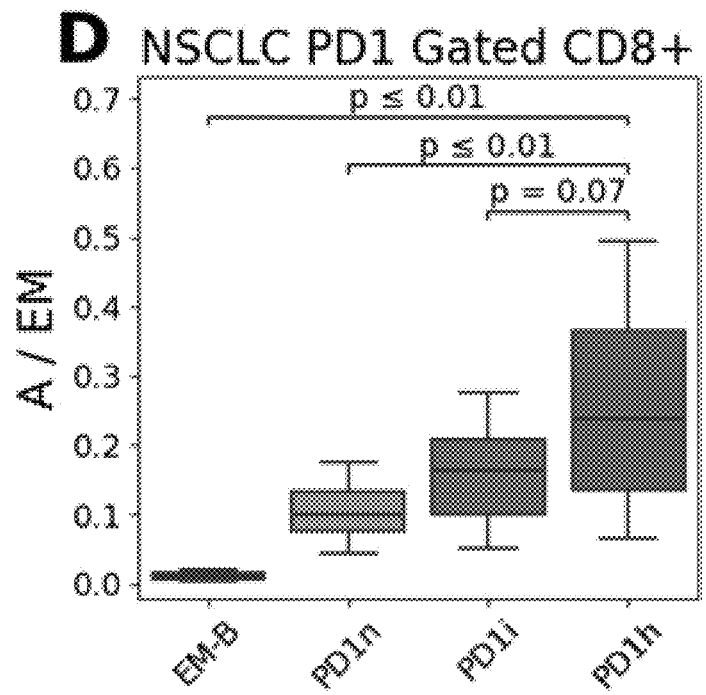
FIG. 15D shows composite activation level for PD1 isolates from FIG. 15C. The composite level is calculated as Activation divided by EM. The alternative hypothesis is that the composite activation level is larger in PD1h isolates than EM-B, PD1n, and PD1i, respectively. For all FIGS. 15A-D, hypotheses were tested using the one-sided Mann-Whitney U test and p-values are denoted or visualized as follows: ns, $p>=0.05$: *, $p<0.05$; , $p<0.01$; *, $p<0.001$; ****, $p<0.0001$.

Herein, we show both in vitro and in-patient samples, many traditional markers for T cell exhaustion are correlated with, but not specific to exhaustion. For instance, gene expression of the inhibitory receptors PD-1, TIM3, and LAG3 is increased in activated T cells as well as exhausted T cells during chronic stimulation (FIG. 11A). In NSCLC patients, PD-1+CD8+ cells are associated with exhaustion (FIG. 14D), however, these PD-1+ cell isolates are also associated with increased Activation (FIG. 15D). Likewise, in NSCLC and CRC patients, CD39+ T cells are associated with both exhausted and EM T cells. While our TCS models corroborated these findings, we also found that CD39+ T cells are associated with higher Activation, suggesting that CD39 is not a specific marker for exhaustion nor EM T cells (FIG. 14A-B, FIG. 15A-B). These findings, paired with observations in literature, suggest a more complex interactions between single-analyte markers and TCS, and point to our TCSP method as a more specific way to characterize infiltrating T cells, especially those in a state of exhaustion.

The use of single-analyte surrogates for complex TCSs is likely driven by the difficulty of comprehensively characterizing TCSs, particularly in FFPE tissue. Typically, accurately estimating TCSs requires flow cytometry and/or functional tests using unpreserved tissue. The TCSP method presented here is the first platform for comprehensive and specific profiling of TCSs in FFPE samples, whether in new or existing RNAseq datasets.

Figure 17A:
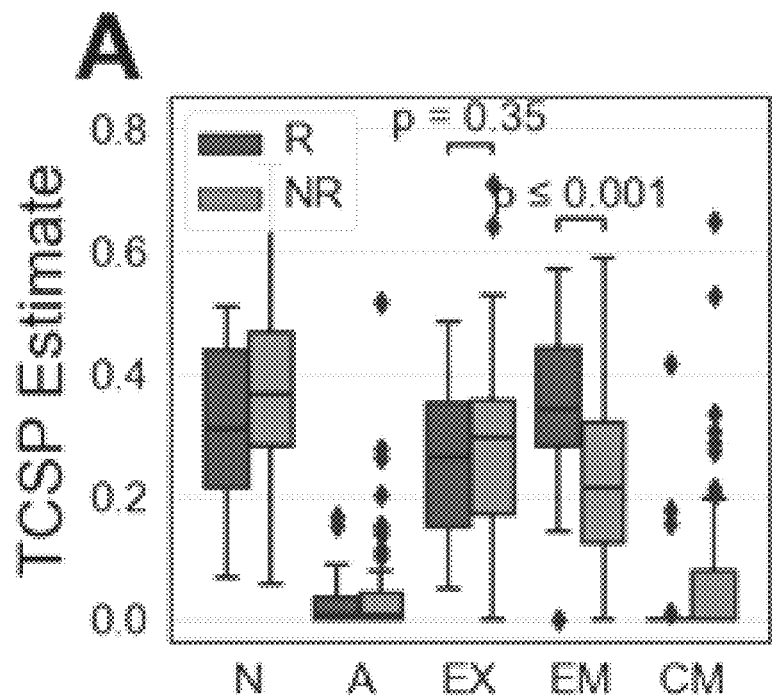
FIG. 17A shows T Cell state profiling as predictive of anti-PD-1 response in patients with recurrent and metastatic Head and Neck Squamous Cell Cancer. Boxplot shows the sum-normalized T Cell State estimates grouped by response to anti-PD1 therapy in the respective indications. R, responder: NR, non-responder, N, Naïve state model: A, Activated state model: EX, Exhausted state model; EM, Effector Memory state model: CM, Central Memory state model: Sum, Sum of all five state models. Hypothesis wastested using the one-sided Mann-Whitney U test. The alternative hypothesis is that EM is higher in responders and EX is higher in non-responders. The following number of samples were in the cohort: R=22 and NR=63.
Figure 17B:
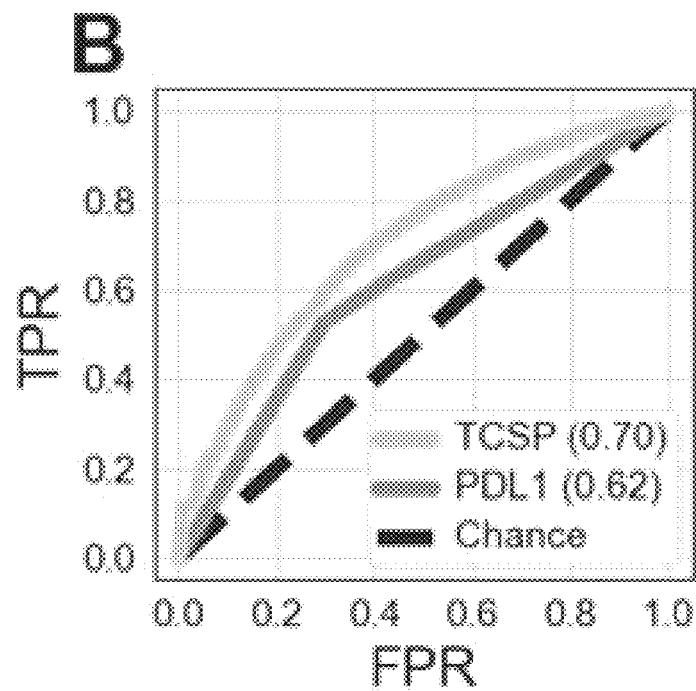
FIG. 17B shows T Cell state profiling as predictive of anti-PD-1 response in patients with recurrent and metastatic Head and Neck Squamous Cell. The receiver operator characteristic (ROC) curves of a biomarker derived from TCSP estimates (TCSP), and where available, PD-L1 IHC (PDL1), and tumor mutational burden (TMB) are shown. Chance is shown as a dotted black line, and the area under each ROC curve (AUC) is detailed in the legend.
Figure 17C:
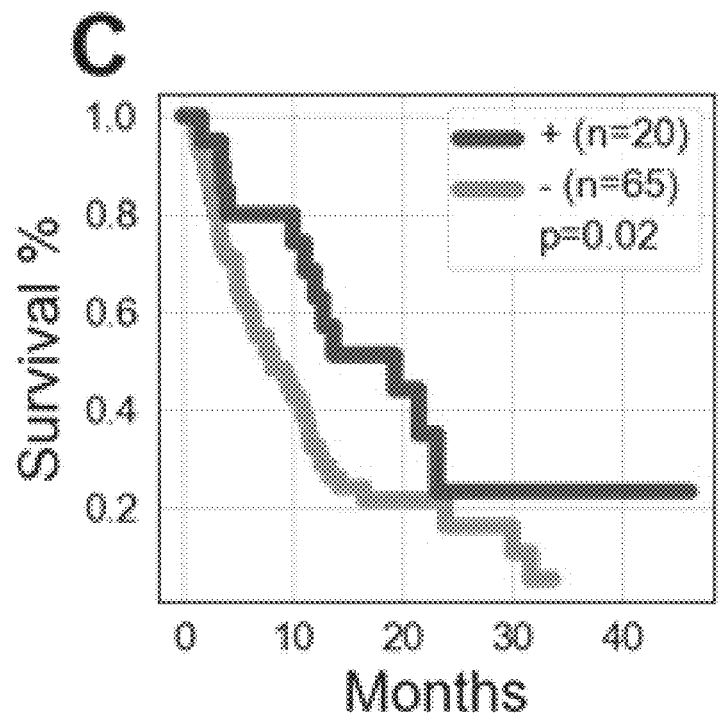
FIG. 17C shows T Cell state profiling as predictive of anti-PD-1 response in patients with recurrent and metastatic Head and Neck Squamous Cell Cancer. Kaplan-Meier plots of overall survival of patients who were predicted by the TCSP biomarker to be responders (+) and non-responder (−) in each respective indication. Hypothesis was tested using the log rank test
Figure 17D:
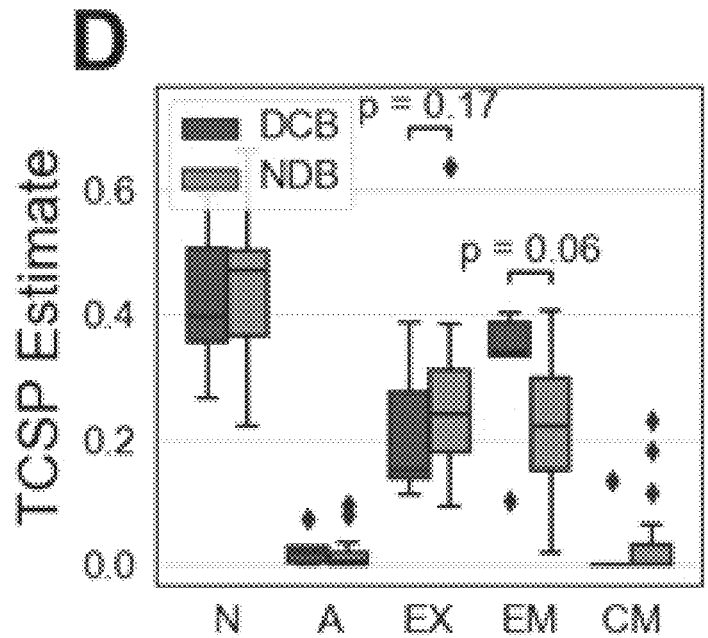
FIG. 17D shows T Cell state profiling as predictive of anti-PD-1 response in patients with recurrent and metastatic Non-small Cell Lung Cancer. Boxplot shows the sum-normalized T Cell State estimates grouped by response to anti-PD therapy Hypothesis was tested using the one-sided Mann-Whitney U test. The alternative hypotheses is that EM is higher in responders and EX is higher in non-responders. The following number of samples were in the cohort: Responder (R)=10 and Non Responders (NR)=21.
Figure 17E:
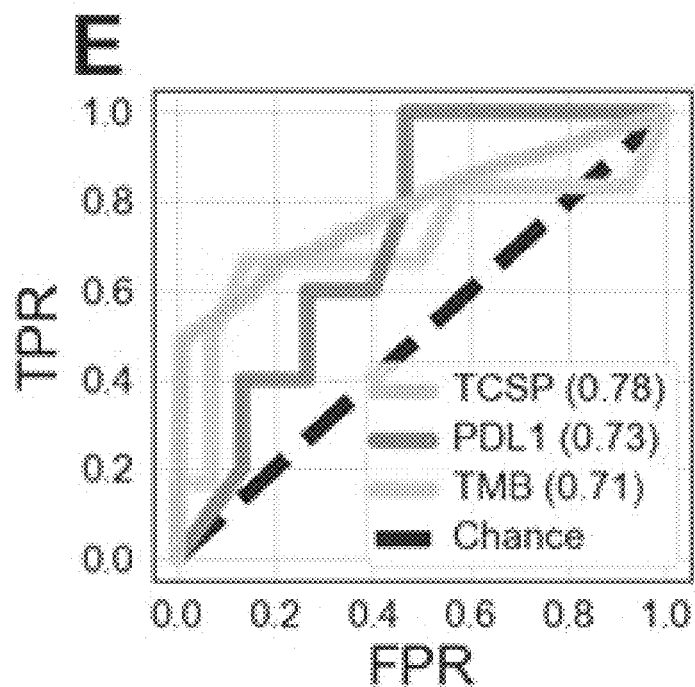
FIG. 17E shows T Cell state profiling as predictive of anti-PD-1 response in patients with recurrent and metastatic Non-small Cell Lung Cancer. The receiver operator characteristic (ROC) curves of a biomarker derived from TCSP estimates (TCSP), and where available, PD-L1 IHC (PDL1), and tumor mutational burden (TMB) are shown. Chance is shown as a dotted black line, and the area under each ROC curve (AUC) is detailed in the legend.
Figure 17F:
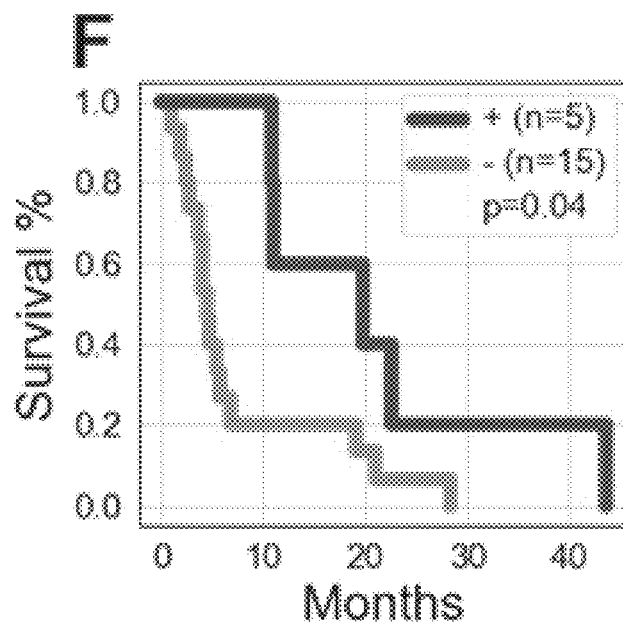
FIG. 17F shows T Cell state profiling as predictive of anti-PD-1 response in patients with recurrent and metastatic Non-small Cell Lung Cancer. Kaplan-Meier plots of overall survival of patients who were predicted by the TCSP biomarker to be responders (+) and non-responder (−) in each respective indication. Hypothesis was tested using the log rank test.
Figure 17G:
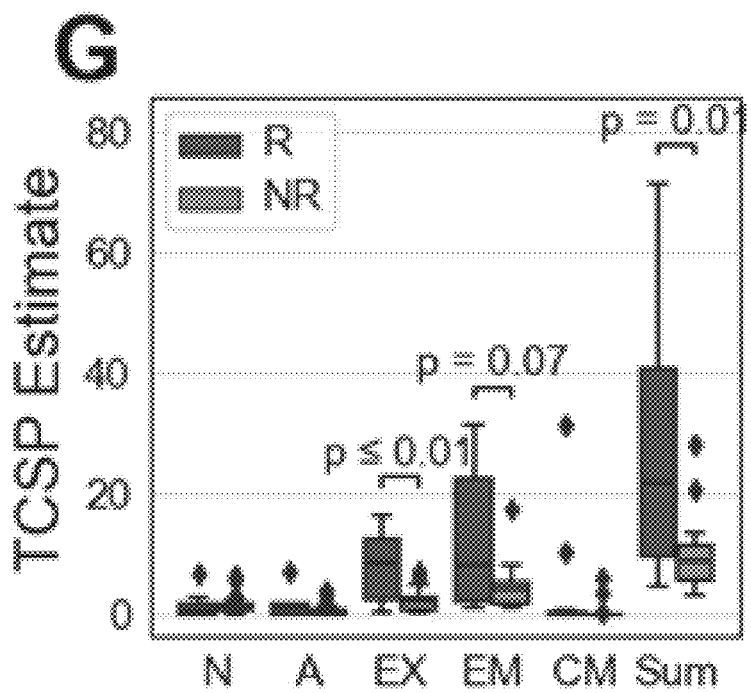
FIG. 17G shows T Cell state profiling as predictive of anti-PD-1 response in patients with recurrent and metastatic Melanoma. Boxplot shows the non-normalized T Cell State estimates grouped by response to anti-PD1 therapy in the respective indications. Hypothesis in was tested using the one-sided Mann-Whitney U test. The alternative hypotheses is that EX, EM, and Sum are higher in responders. The following number of samples were in the cohort: DCB=6 and NDB=15. DCB=durable clinical benefit: NDB=non-durable benefit.
Figure 17H:
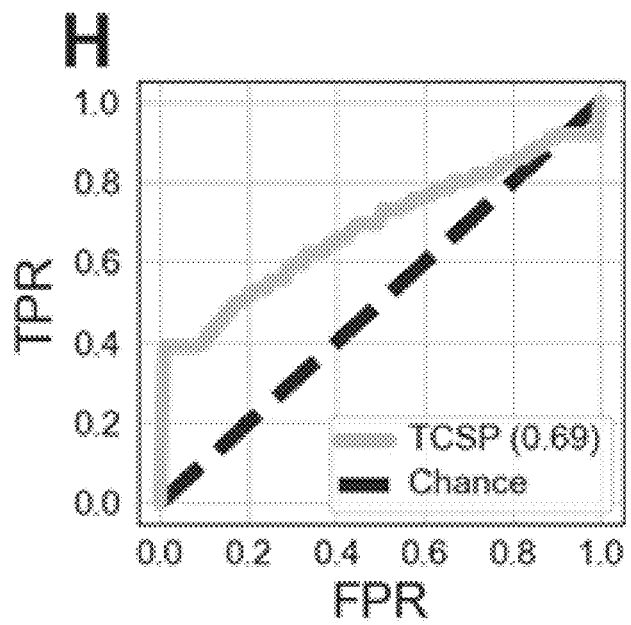
FIG. 17H shows T Cell state profiling as predictive of anti-PD-1 response in patients with recurrent and metastatic Melanoma. The receiver operator characteristic (ROC) curves of a biomarker derived from TCSP estimates (TCSP), and where available. PD-L1 IHC (PDL1), and tumor mutational burden (TMB) are shown for each respective indication. Chance is shown as a dotted black line, and the area under each ROC curve (AUC) is detailed in the legend.
Figure 17I:
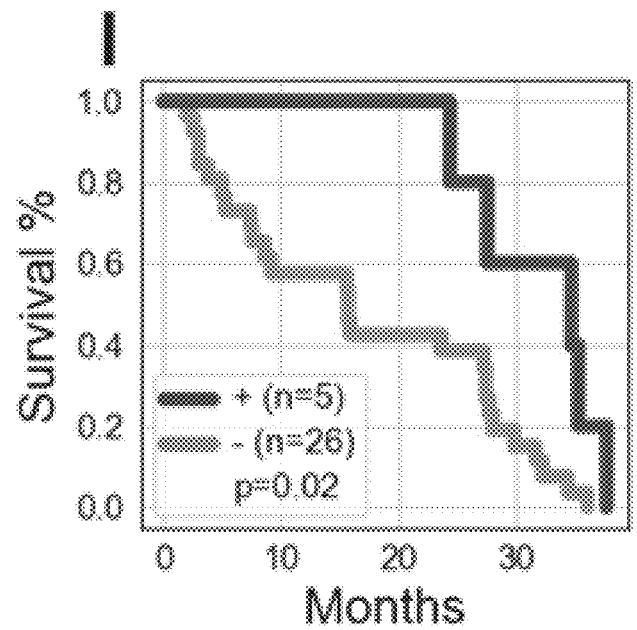
FIG. 17I shows T Cell state profiling as predictive of anti-PD-1 response in patients with recurrent and metastatic Melanoma. Kaplan-Meier plots of overall survival of patients who were predicted by the TCSP biomarker to be responders (+) and non-responder (−) in each respective indication. Hypotheses was tested using the log rank test.

Importantly, the TCSP method provided herein is not only useful for characterizing TCS, but also for developing multianalyte biomarkers to predict patient response to immunotherapy. In HNSCC and NSCLC patients, TCSP-based biomarkers outperformed existing biomarkers, namely the companion diagnostic PD-L1 IHC (FIG. 17A-F). Similarly, a TCSP-based biomarker predicted objective response and overall survival in a public melanoma patient cohort (FIG. 17G-I). Additional studies will be performed to validate these biomarkers, but this work demonstrates the ability of TCSP to serve as a platform not just for characterizing T cells, but for building biomarkers and predicting patient response in multiple cancer types. Supporting the idea that TCSP works across many cancer types, we characterized TCSs across 32 cancer types and found potential indications to pursue for biomarker development.

While the examples provided herein demonstrate that the instant TCSP based methods can be used to predict the efficacy of anti-PD-1 based therapies, it is contemplated that the efficacy of other therapies (including other immunotherapies) could also be predicted using the methods provided herein. For example, it is contemplated that the TCSP based methods could be used to predict efficacy of any immunotherapy, including without limitation other checkpoint inhibitors (e.g. anti-PD-L1 therapies or anti-CTLA4 therapies), cytokine therapies, immunotherapeutic vaccines, antibody therapies, cellular immunotherapies (e.g. dendritic cell therapies, CAR-T cell therapy, CAR-NK cell therapy, CAR-Macrophage cell therapy, autologous or allogeneic T Cell receptor therapy, etc.), or any other therapy. It is also contemplated that the TCSP based methods could be used for other therapies as well, such as chemotherapy or radiotherapy.

A non-limiting example of a workflow process is depicted in FIG. 1. In a first step a formalin-fixed paraffin-embedded (FFPE) sample 101 is provided. RNA extraction 103 is performed followed by sequencing library generation 105. Target gene enrichment 107 is then performed followed by sequencing. Raw sequencing data 109 is generated, which is then used to determine cellular status 113 and, optionally, immune modulatory molecule expression 111 and cell type and ratio deconvolution 115. The cellular status 113 and optional immune modulatory molecule expression 111 and cell type and ratio deconvolution 115 is then used to generate a report 117 describing the status of cells in the sample. The report 117 may contain a breakdown of the amount or percentage of cells of each status in any form, for example a pie chart. The report 117 may display percentages of cells in Exhausted, Naïve, Activated, Effector Memory, and Central Memory states when the sample being analyzed contains T-cells, for example CD4+ or CD8+ T-cells. When the process depicted in FIG. 1 comprises the optional step of measuring cell type and ratio deconvolution 115, the report 117 may further break down cell status according to cell type. For example, a sample being analyzed comprising a mixture of CD4+ and CD8+ T-cells may issue a report describing the percentages of CD4+ cells in Exhausted, Naïve, Activated, Effector Memory, and Central Memory states and the percentages of CD8+ cells in Exhausted, Naïve, Activated, Effector Memory. and Central Memory states separately. If the process depicted in FIG. 1 comprises the optional step of measuring immune modulatory molecule expression 111, the quantity and identity of these molecules may also be included in the report 117.

Provided herein are systems and methods for determining cellular status of cells from a sample of a subject. In some instances, the subject is having or is suspected of having a disease or disorder. In some instances, the determination of cellular is used for diagnosing the subject with a disease or disorder. In some instances, the cellular status is a T cell status as described herein. Alternatively or in combination, the determination of cellular status is used for determining or predicting a response to a therapeutic intervention in the subject.

Determination of cellular status as described herein can comprise first obtaining a sample from a subject. In some instances, the sample is any fluid or other material derived from the body of a normal or disease subject including, but not limited to, blood, serum, plasma, lymph, urine, saliva, tears, cerebrospinal fluid, milk, amniotic fluid, bile, ascites fluid, organ or tissue extract, and culture fluid in which any cells or tissue preparation from a subject has been incubated. In some instances, the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. In some instances, the sample is a cancer sample. The cancer sample is typically a solid tumor sample or a liquid tumor sample. For example, the cancer sample is obtained from excised tissue. In some instances, the sample is fresh, frozen, or fixed. In some instances, a fixed sample comprises paraffin-embedded or fixation by formalin, formaldehyde, or glutaraldehyde. In some instances, the sample is formalin-fixed paraffin-embedded.

In some instances, the sample comprises immune cells from a subject. In some instances, the sample comprises purified immune cells from a subject. In some instances, the purified immune cells are to be used in a cell therapy treatment. In some instances, the immune cells are from a subject receiving an immunotherapy. In some instance, the immune cells are from a subject who is a candidate for an immunotherapy.

In some instances, the sample is stored after it has been collected, but before additional steps are to be performed. In some instances, the sample is stored at less than 8° C. In some instances, the sample is stored at less than 4° C. In some instances, the sample is stored at less than 0° C. In some instances, the sample is stored at less than −20° C. In some instances, the sample is stored at less than −70° C. In some instances, the sample is stored a solution comprising glycerol, glycol, dimethyl sulfoxide, growth media, nutrient broth or any combination thereof. The sample may be stored for any suitable period of time. In some instances the sample is stored for any period of time and remains suitable for downstream applications. For example, the sample is stored for any period of time before nucleic acid (e.g., ribonucleic acid (RNA) or deoxyribonucleic acid (DNA)) extraction. In some instances, the sample is stored for at least or about 1 day, 2 day, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 12 months, or more than 12 months. In some instances, the sample is stored for at least 1 year, 2 years, 3, years, 4 years, 5 years, 6 years, 7 years, 8 years, 9 years, 10 years, 1 years, 12 years, or more than 12 years.

Disclosed herein are methods and systems that generate an immune-oncology profile from a sample of a subject, wherein the sample comprises a nucleic acid molecule. In some instances, the nucleic acid molecule is RNA, DNA, RNA fragments, DNA fragments, or combinations thereof. In some instances, after a sample is obtained, the sample is processed further before analysis. In some instances, the sample is processed to extract the nucleic acid molecule from the sample. In some instances, no extraction or processing procedures are performed on the sample. In some instances, the nucleic acid is extracted using any technique that does not interfere with subsequent analysis. Extraction techniques include, for example, alcohol precipitation using ethanol, methanol or isopropyl alcohol. In some instances, extraction techniques use phenol, chloroform, or any combination thereof. In some instances, extraction techniques use a column or resin based nucleic acid purification scheme such as those commonly sold commercially. In some instances, following extractions, the nucleic acid molecule is purified. In some instances, the nucleic acid molecule is further processed. For example, following extraction and purification, RNA is further reverse transcribed to cDNA. In some instances, processing of the nucleic acid comprises amplification. Following extraction or processing, in some instances, the nucleic acid is stored in water, Tris buffer, or Tris-EDTA buffer before subsequent analysis.

A nucleic acid molecule obtained from a sample comprises may be characterized by factors such as integrity of the nucleic acid molecule or size of the nucleic acid molecule. In some instances, the nucleic acid molecule is DNA. In some instances, the nucleic acid molecule is RNA. In some instances, the RNA or DNA comprises a specific integrity. For example, the RNA integrity number (RN) of the RNA is no more than about 2. In some instances, the RNA molecules in a sample have a RIN of about 2 to about 10. In some instances, the RNA molecules in a sample have a RIN of at least about 2. In some instances, the RNA molecules in a sample have a RIN of at most about 10. In some instances, the RNA molecules in a sample have a RIN of about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10, or about 9 to about 10. The RNA molecule in a sample may be characterized by size. In some instances, at least 10%, 20%, 30%, 40%, 50%, 60%, 70%, 80%, or 90%, or more of the RNA molecules in a sample are at least 150, 175, 200, 225, 250, 275, 300, 325, 350, 375, 400, or more than 400 nucleotides in size. In some instances, the RNA molecules in the sample are at least 200 nucleotides in size. In some instances, the RNA molecules of at least 200 nucleotides in size comprise a percentage of the sample (DV200). For example, the percentage is at least or about 40%, 45%, 50%, 55%, 60%, 65%, 70%, 75%, 80%, 85%, 90%, 95%, or more than 95%. In some instances, the RNA molecules in a sample have a DV200 value of about 10% to about 90%.

In some instances, after the samples have been obtained and nucleic acid molecule isolated, the nucleic acid molecule is prepared for sequencing. In some instances, a sequencing library is prepared. Numerous library generation methods have been described. In some instances, methods for library generation comprise addition of a sequencing adapter. Sequencing adapters may be added to the nucleic acid molecule by ligation. In some instances, library generation comprises an end-repair reaction.

Sometimes, library generation for sequencing comprises an enrichment step. For example, coding regions of the mRNA are enriched. In some instances, the enrichment step is for a subset of genes. In some instances, the enrichment step comprises using a bait set. The bait set may be used to enrich for genes used for specific downstream applications. A bait set generally refers to a set of baits targeted toward a selected set of genomic regions of interest. For example, a bait set may be selected for genomic regions relating to at least one of immune modulatory molecule expression, cell type and ratio, or cellular status. In some instances, one bait set is used for determining immune modulatory molecule expression, a second bait set is used for determining cell type and ratio, and a third bait set is used for determining cellular status. In some instances, the same bait set is used for determining immune modulatory molecule expression, cell type and ratio, cellular status, or combinations thereof. In some instances, a bait set comprises at least one unique molecular identifier (UMI). The term "unique molecular identifier (UMI)" or "UMI" as used herein refers to nucleic acid having a sequence which can be used to identify and/or distinguish one or more first molecules to which the UMI is conjugated from one or more second molecules. In some instances, the UMI is conjugated to one or more target molecules of interest or amplification products thereof. UMIs may be single or double stranded.

The systems and methods disclosed herein provide for the sequencing for a number of genes. In some instances, the number of genes is at least about 10, 50, 100, 200, 300, 400, 500, 600, 70, 800, 900, 1000, 1500, 2000, 2500, 3000, 3500, 4000, 4500, 5000, 5500, 6000, 6500, 7000, 7500, 8000, 8500, 9000, 9500, 10000, or more than 10000 genes. In some instances, the number of genes to be sequenced is in a range of about 5× to about 1000 genes. In some instances, the number of genes to be sequenced is in a range of about at least 200. In some instances, the number of genes to be sequenced is in a range of about at most 10,000. In some instances, the number of genes to be sequenced is in a range of about 1 to 50, 50 to 100, 100 to 200, 200 to 500, 200 to 1,000, 200 to 2.000, 200 to 4,000, 200 to 6.000, 200 to 8,000, 200 to 10,000, 500 to 1,000, 500 to 2,000, 500 to 4,000, 500 to 6,000, 500 to 8,000, 500 to 10,000, 1,000 to 2,000, 1,000 to 4,000, 1,000 to 6,000, 1,000 to 8,000, 1,000 to 10,000, 2,000 to 4,000, 2,000 to 6,000, 2,000 to 8,000, 2,000 to 10,000, 4,000 to 6,000, 4,000 to 8,000, 4,000 to 10,000, 6,000 to 8,000, 6,000 to 10.000, or 8,000 to 10,000. Examples of genes to be sequenced are seen in Table 1 and Tables 2A-2E.

Sequencing may be performed with any appropriate sequencing technology. Examples of sequencing methods include, but are not limited to single molecule real-time sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

Sequencing methods may include, but are not limited to, one or more of high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxim-Gilbert sequencing, and primer walking. Sequencing may generate sequencing reads ("reads"), which may be processed (e.g., alignment) to yield longer sequences, such as consensus sequences. Such sequences may be compared to references (e.g., a reference genome or control) to identify variants, for example.

Sequencing methods may include a barcoding or "tagging" step. In some instances barcoding (or "tagging") can allow for generation of a population of samples of nucleic acids, wherein each nucleic acid can be identified from which sample the nucleic acid originated. In some instances, the barcode comprises oligonucleotides that are ligated to the nucleic acids. In some instances, the barcode is ligated using an enzyme, including but not limited to, *E. coli* ligase, T4 ligase, mammalian ligases (e.g., DNA ligase I, DNA ligase II, DNA ligase III, DNA ligase IV), thermostable ligases, and fast ligases.

Barcoding or tagging may occur using various types of barcodes or tags. Examples of barcodes or tags include, but are not limited to, a radioactive barcode or tag, a fluorescent barcode or tag, an enzyme, a chemiluminescent barcode or tag, and a colorimetric barcode or tag. In some instances, the barcode or tag is a fluorescent barcode or tag. In some instances, the fluorescent barcode or tag comprises a fluorophore. In some instances, the fluorophore is an aromatic or heteroaromatic compound. In some instances, the fluorophore is a pyrene, anthracene, naphthalene, acridine, stilbene, benzoxaazole, indole, benzindole, oxazole, thiazole, benzothiazole, canine, carbocyanine, salicylate, anthranilate, xanthene dye, coumarin. Examples of xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N; N'-tetramethyl-6-carboxyrhodamine (TAMRA), 6-carboxy-X-rhodamine (ROX). In some instances, the fluorescent barcode or tag also includes the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl) aminonaphthalene-1-sulfonic acid (EDANS). Examples of coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxypentyl)-3'-ethyl-5,5'-dimethyloxacarbocyanine (CyA); 1H, 5H, 11H, 15H-Xantheno[2,3, 4-ij: 5,6, 7-i'j']diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3, 6,7, 12,13, 16,17-octahydro-inner salt (TR or Texas Red); or BODIPY™ dyes.

In some instances, a different barcode or tag is supplied a sample comprising nucleic acids. Examples of barcode lengths include barcode sequences comprising, without limitation, about 1, 2, 3, 4, 5, 6, 7, 8, 9, 10, 15, 20, 25 or more bases in length. Examples of barcode lengths include barcode sequences comprising, without limitation, from 1-5, 1-10, 5-20, or 1-25 bases in length. Barcode systems may be in base 1, 2, 3, 4, 5, 6, 7, 8, 9, or 10 or a similar coding scheme. In some instances, a number of barcodes is at least or about 1, 2, 3, 4, 5, 6, 7, 8, 9, 10, 11, 12, 13, 14, 15, 16, 17, 18, 19, 20, 25, 50, 100, 200, 300, 400, 500, 600, 700, 800, 900, 1000, 2000, 4000, 6000, 8000, 10000, 12000, 14000, 16000, 18000, 20000, 25000, 30000, 40000, 50000, 100000, 500000, 1000000, or more than 1000000 barcodes. In some instances, a number of barcodes is in a range of 1-1000000 barcodes. In some instances, the number of barcodes is in a range of about 1-10 1-50 1-100 1-500 1-1000 1-5,000 1-10000 1-50000 1-100000 1-500000 1-1000000 10-50 10-100 10-500 10-1000 10-5,000 10-10000 10-50000 10-100000 10-500000 10-1000000 50-100 50-500 50-1000 50-5,000 50-10000 50-50000 50-100000 50-500000 50-1000000 100-500 100-1000 100-5,000 100-10000 100-50000 100-100000 100-500000 100-1000000 500-1000 500-5,000 500-10000 500-50000 500-100000 500-500000 500-1000000 1000-5,000 1000-10000 1000-50000 1000-100000 1000-500000 1000-1000000 5,000-10000 5,000-50000 5,000-100000 5,000-500000 5,000-1000000 10000-50000 10000-100000 10000-500000 10000-1000000 50000-100000 50000-500000 50000-1000000 100000-500000 100000-1000000 or 500000-1000000 barcodes.

Cellular Status Determination

Figure 2:
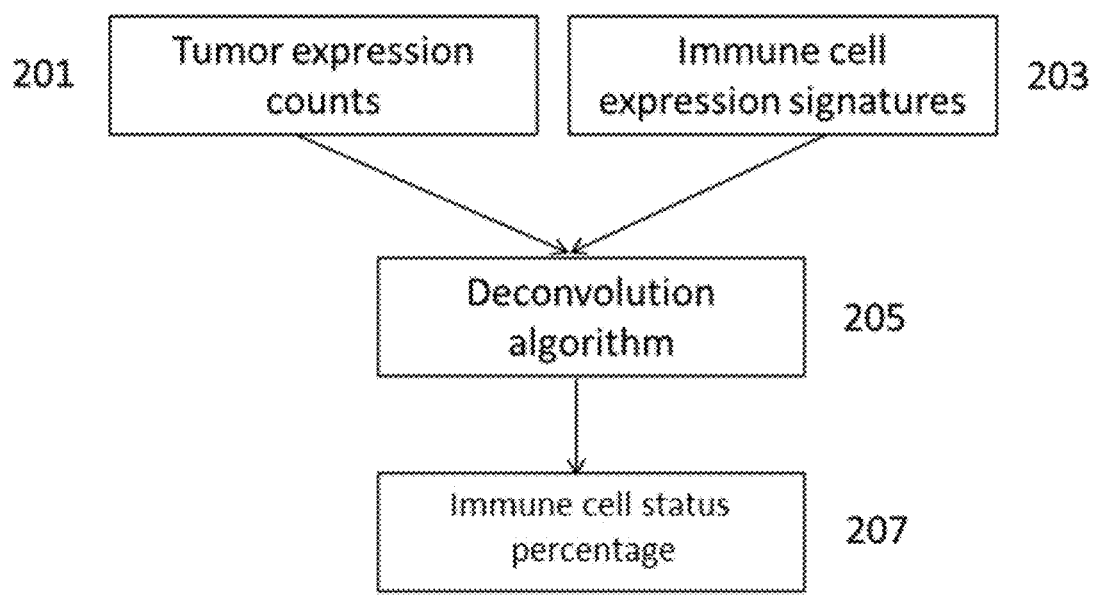
FIG. 2 depicts an example workflow for cell status deconvolution.

Following sequencing of a sample, sequencing data as described herein can be used for determining cellular status of immune cells in the sample. An example of a workflow is seen in FIG. 2, which depicts a situation wherein the sample comprises tumor cells as well as other immune cell types. Referring to FIG. 2, sequencing data is used to determine tumor expression counts 201 and immune cell expression counts 203. The tumor expression counts 201 and immune cell expression counts 203 are then subjected to a deconvolution algorithm 205 to calculate immune cell status percentage 207.

Sequencing data as provided herein are used to determine gene expression. In some instances, the sequencing data is obtained from sequencing RNA from a sample. In some instances, the gene expression is of cell status signature genes. Cell status signature genes are genes that correlate with a cell having a particular status. Examples of cellular statuses are terminally exhausted status, progenitor exhausted status, naïve status, activated status, stimulation recovered status, effector memory status, central memory status, or stem cell memory status. Examples of genes that correlate with a cell having a status include, but are not limited to, the genes listed in Table 1 below. In some instances, the genes listed in Table 1 are used to differentiate or assign the status of a T-cell. The status assigned to the T-cell may be terminally exhausted status, progenitor exhausted status, naïve status, activated status, stimulation recovered status, effector memory status, central memory status, or stem cell memory status. In some instances, terminal exhaustion status signature genes comprise one or more genes selected from Table 1. In some instances, progenitor exhaustion status signature genes comprise one or more genes selected from Table 1. In instances, naïve status signature genes comprise one or more genes selected from Table 1. In instances, activation status signature genes comprise one or more genes selected from Table 1. In some instances, stimulation recovered status signature genes comprise one or more genes selected from Table 1. In instances, effector memory status signature genes comprise one or more genes selected from Table 1. In instances, central memory status signature genes comprise one or more genes selected from Table 1.

TABLE 1

| Gene ID | Gene Name |
| --- | --- |
| ENSG00000000971 | CFH |
| ENSG00000007516 | 8AIAP3 |
| ENSG00000008516 | MMP25 |
| ENSG00000009694 | TENM1 |
| ENSG00000021300 | PLEKHB1 |
| ENSG00000065328 | MCM10 |
| ENSG00000068831 | RASGRP2 |
| ENSG00000070159 | PTPN3 |
| ENSG00000071575 | TRIB2 |
| ENSG00000072110 | ACTN1 |
| ENSG00000075340 | ADD2 |
| ENSG00000077984 | CST7 |
| ENSG00000078900 | TP73 |
| ENSG00000089685 | BIRC5 |
| ENSG00000091409 | ITGA6 |
| ENSG00000099139 | PCSK5 |
| ENSG00000100346 | CACNA1I |
| ENSG00000100368 | CSF2RB |
| ENSG00000100628 | ASB2 |
| ENSG00000101134 | DOK5 |
| ENSG00000101842 | VSIG1 |
| ENSG00000102003 | SYP |
| ENSG00000103811 | CTSH |
| ENSG00000104689 | TNFRSF10A |
| ENSG00000105246 | EBI3 |
| ENSG00000105369 | CD79A |
| ENSG00000106624 | AEBP1 |
| ENSG00000107796 | ACTA2 |
| ENSG00000109471 | IL2 |
| ENSG00000110944 | IL23A |
| ENSG00000111537 | IFNG |
| ENSG00000111961 | SASH1 |
| ENSG00000112379 | ARFGEF3 |
| ENSG00000112394 | SLC16A10 |
| ENSG00000112984 | KSF20A |
| ENSG00000113739 | STC2 |
| ENSG00000114812 | VIPR1 |
| ENSG00000115457 | IGFBP2 |

TABLE 1-continued

| Gene ID | Gene Name |
| --- | --- |
| ENSG00000116106 | EPHA4 |
| ENSG00000118200 | CAMSAP2 |
| ENSG00000118257 | NRP2 |
| ENSG00000120129 | DUSP1 |
| ENSG00000122224 | LY9 |
| ENSG00000125144 | MT1G |
| ENSG00000127564 | PKMYT1 |
| ENSG00000128342 | LIF |
| ENSG00000132359 | RAP1GAP2 |
| ENSG00000132694 | ARHGEF11 |
| ENSG00000134508 | CABLES1 |
| ENSG00000134539 | KLRD1 |
| ENSG00000135362 | PRR5L |
| ENSG00000137501 | SYTL2 |
| ENSG00000138061 | CYP1B1 |
| ENSG00000138119 | MYOF |
| ENSG00000138180 | CEP55 |
| ENSG00000138768 | USO1 |
| ENSG00000139679 | LPAR6 |
| ENSG00000142347 | MYO1F |
| ENSG00000143776 | CDC42BPA |
| ENSG00000146904 | EPHA1 |
| ENSG00000147457 | CHMP7 |
| ENSG00000148053 | NTRK2 |
| ENSG00000150938 | CRIM1 |
| ENSG00000151623 | NR3C2 |
| ENSG00000152969 | JAKMIP1 |
| ENSG00000153234 | NR4A2 |
| ENSG00000154027 | AK5 |
| ENSG00000154165 | GPR15 |
| ENSG00000156475 | PPP2R2B |
| ENSG00000157404 | KIT |
| ENSG00000157680 | DGKI |
| ENSG00000158321 | AUTS2 |
| ENSG00000158470 | BAGALT5 |
| ENSG00000159640 | ACE |
| ENSG00000160791 | CCR5 |
| ENSG00000161381 | PLXDC1 |
| ENSG00000162078 | ZG16B |
| ENSG00000162433 | AK4 |
| ENSG00000162599 | NFIA |
| ENSG00000162772 | ATF3 |
| ENSG00000163492 | CCDC141 |
| ENSG00000164045 | CDC25A |
| ENSG00000164171 | ITGA2 |
| ENSG00000164400 | CSF2 |
| ENSG00000164484 | TMEM200A |
| ENSG00000165272 | AQP3 |
| ENSG00000165304 | MELK |
| ENSG00000166592 | RRAD |
| ENSG00000166920 | C15orf48 |
| ENSG00000167094 | TTC16 |
| ENSG00000167618 | LAIR2 |
| ENSG00000167772 | ANGPTL4 |
| ENSG00000168685 | IL7R |
| ENSG00000168824 | NSG1 |
| ENSG00000169398 | PTK2 |
| ENSG00000169896 | ITGAM |
| ENSG00000170485 | NPAS2 |
| ENSG00000170955 | CAVIN3 |
| ENSG00000171860 | C3AR1 |
| ENSG00000172005 | MAL |
| ENSG00000172794 | RAB37 |
| ENSG00000172915 | NBEA |
| ENSG00000174807 | CD248 |
| ENSG00000175048 | ZDHHC14 |
| ENSG00000177494 | ZBED2 |
| ENSG00000178S73 | MAF |
| ENSG00000180549 | FUT7 |
| ENSG00000181036 | FCRL6 |
| ENSG00000181754 | AMIGO1 |
| ENSG00000182718 | ANXA2 |
| ENSG00000184014 | DENND5A |
| ENSG00000184545 | DUSP8 |
| ENSG00000185697 | MYBL1 |
| ENSG00000186185 | KIF18B |
| ENSG00000188761 | BCL2L15 |
| ENSG00000189233 | NUGGC |

TABLE 1-continued

| Gene ID | Gene Name |
| --- | --- |
| ENSG00000196576 | PLXNB2 |
| ENSG00000196782 | MAML3 |
| ENSG00000198915 | RASGEF1A |
| ENSG00000203710 | CR1 |
| ENSG00000204219 | TCEA3 |
| ENSG00000232388 | SMIM26 |
| ENSG00000270276 | HIST2H4B |
| ENSG00000271503 | CCL5 |
| ENSG00000275410 | HNF1B |

Further examples of genes that correlate with a cell having a status include, but are not limited to, the genes listed in Table 1B below. In some instances, the genes listed in Table 1B are used to differentiate or assign the status of a T-cell. The status assigned to the T-cell may be terminally exhausted status, progenitor exhausted status, naïve status, activated status, stimulation recovered status, effector memory status, central memory status, or stem cell memory status. In some instances, terminal exhaustion status signature genes comprise one or more genes selected from Table 1B. In some instances, progenitor exhaustion status signature genes comprise one or more genes selected from Table 1B. In instances, naive status signature genes comprise one or more genes selected from Table 1B. In instances, activation status signature genes comprise one or more genes selected from Table 13. In some instances, stimulation recovered status signature genes comprise one or more genes selected from Table 1B. In instances, effector memory status signature genes comprise one or more genes selected from Table 1B. In instances, central memory status signature genes comprise one or more genes selected from Table 1B.

TABLE 1B

| Deconvolution Genes for T-Cell Status | | | | |
| --- | --- | --- | --- | --- |
| MMP25 | EBI3 | LEF1 | CCDC141 | GP5 |
| ZBTB32 | CD79A | CCDC65 | CSF2 | DUSP8 |
| RASGRP2 | IL2 | LPAR6 | TTC16 | NUGGC |
| TBX21 | IL23A | NR3C2 | C3AR1 | C1orf228 |
| LAG3 | SLC16A10 | NR4A2 | MAL | C17orf107 |
| CSF2RB | CCR2 | GPR15 | CD248 | AMY2B |
| ASB2 | LY9 | PPP2R2B | ZDHHC14 | |
| DOK5 | MT1G | CCR5 | GCNT4 | |
| VSIG1 | CFP | PLXDC1 | ZBED2 | |
| ATP8B4 | KLRD1 | ZG16B | MAF | |

T-cells in an exhausted state are characterized by cells that have been overstimulated. In some instances, exhausted T-cells have been overstimulated and have reduced cytotoxic function. In some instances, exhausted T-cells can be characterized by their gene expression profiles. In some instances, terminal exhausted T-cells can be characterized by their inability to transition to other statuses. In some instances, progenitor exhausted T-cells can be characterized by their ability to transition to other statuses. In some instances, the genes of interest in identifying T-cell exhaustion comprise one or more genes selected from Table 1. In some instances, the genes of interest in identifying T-cell exhaustion comprise one or more genes selected from Table 1B. In some instances, the exhausted T-cells are terminally exhausted T-cells. In some instances, the exhausted T-cells are progenitor exhausted T-cells.

T-cells in a naïve state are cells that have yet to encounter an antigen. As such, they have not differentiated and may not possess any cytotoxic activity. In some instances, naïve T-cells can be characterized by their gene expression profiles. In some instances, the genes of interest in identifying naive T-cells comprise one or more genes selected from Table 1. In some instances, the genes of interest in identifying naive T-cells comprise one or more genes selected from Table 1B T-cells in an activated state are cells that have been subject to engagement of cognate antigen and co-stimulation. In the context of an immunotherapy, an active T-cell may be able to deliver cytotoxic performance to the diseased tissue. Thus, a high population of active T-cells may be indicative of an immunotherapy being efficacious. In some instances, stimulation recovered status can be characterized by a T cell that was previously in an activated state. In some instances, activated T-cells can be characterized by their gene expression profiles. In some instances, the genes of interest in identifying activated T-cells comprise one or more genes selected from Table 1. In some instances, the genes of interest in identifying activated T-cells comprise one or more genes selected from Table 1B. In some instances, activation recovered T-cells can be characterized by their gene expression profiles. In some instances, the genes of interest in identifying activation recovered T-cells comprise one or more genes selected from Table 1. In some instances, the genes of interest in identifying activation recovered T-cells comprise one or more genes selected from Table 1B.

T-cells in a central memory state are important to the adaptive immune process. In some instances, central memory T-cells can be characterized by their gene expression profiles. In some instances, the genes of interest in identifying central memory T-cells comprise one or more genes selected from Table 1. In some instances, the genes of interest in identifying central memory T-cells comprise one or more genes selected from Table 1B.

T-cells in an effector memory state are important to the adaptive immune process. In some instances, effector memory T-cells can be characterized by their gene expression profiles. In some instances, the genes of interest in identifying effector memory T-cells comprise one or more genes selected from Table 1. In some instances, the genes of interest in identifying effector memory T-cells comprise one or more genes selected from Table 1B.

T-cells in a stem cell memory state are important to the adaptive immune process. In some instances, stem cell memory T-cells can be characterized by their gene expression profiles. In some instances, the genes of interest in identifying stem cell memory T-cells comprise one or more genes selected from Table 1. In some instances, the genes of interest in identifying stem cell memory T-cells comprise one or more genes selected from Table 1B.

In some instances, the sequencing data is used to determine immune cell expression. In some instances, determining immune cell expression allows a determination of the status of the immune cells. Examples of immune cells whose status is able to be detected by methods described herein include, but are not limited to, CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the sequencing data is used to determine expression of non-immune cells including, but not limited to, stromal cells, stem cells, or tumor cells.

Figure 3:
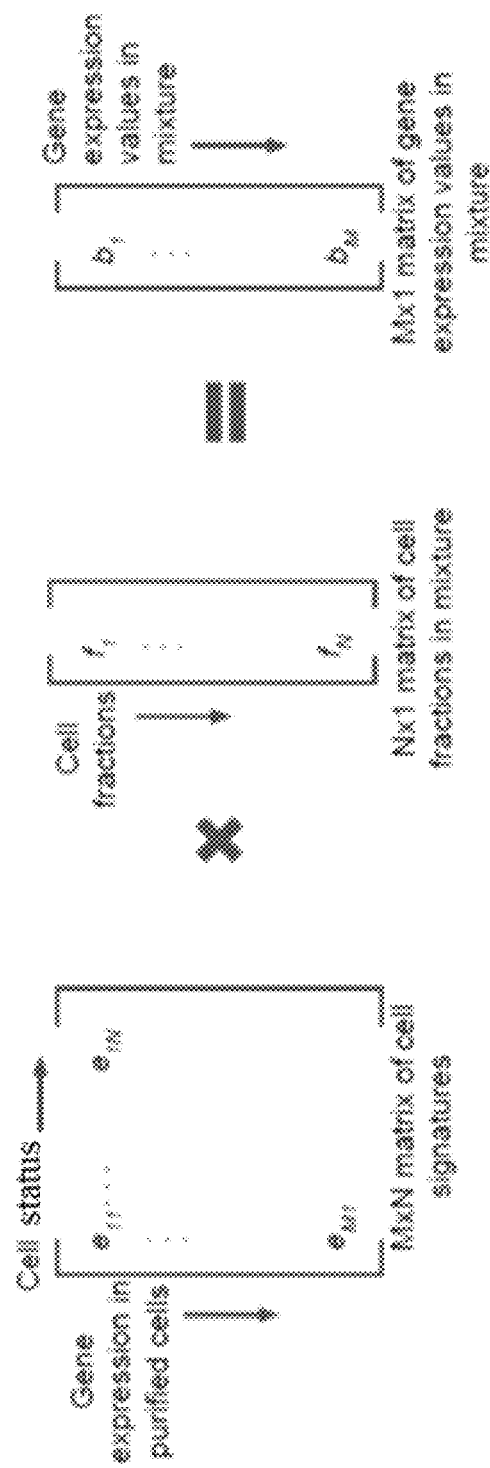
FIG. 3 depicts a schematic for normalization.

Methods and systems for determining cell status may comprise determining gene expression. In some instances, determining cell status may further comprise methods relating to deconvolution. In some instances, a deconvolution matrix is used. The deconvolution matrix typically comprises gene expression for one or more cell statuses. In some instances, the matrix is used for a complex data set of RNA sequencing gene expression data to allow for identification of cell statuses in the data and the relative proportions of each cell status. See FIG. 3. In some instances, individual cell states or statuses and the relative proportion of these individual cell states or statuses are determined from sequencing data using a deconvolution algorithm. The deconvolution algorithm can comprise a deconvolution matrix or a machine learning model. In some cases, the relative proportion, quantification, or percentage of at least 1 cell status, at least 2 cell statuses, at least 3 cell statuses, at least 4 cell statuses, at least 5 cell statuses, at least 6 cell statuses, at least 7 cell statuses, at least 8 cell statuses, at least 9 cell statuses, at least 10 cell statuses, at least 11 cell statuses, at least 12 cell statuses, at least 13 cell statuses, at least 14 cell statuses, at least 15 cell statuses, at least 16 cell statuses, at least 17 cell statuses, at least 18 cell statuses, at least 19 cell statuses, at least 20 cell statuses, at least 21 cell statuses, at least 22 cell statuses, at least 23 cell statuses, or at least 24 cell statuses are determined from sequencing data using a deconvolution matrix. A matrix equation illustrates the mathematical relationship between a matrix comprising expression signatures of individual cell statuses, the percentage of each cell status, and the bulk expression counts. In some instances, the matrix equation is $Ax=b$, where A is the T cell status expression fingerprints (i.e., deconvolution matrix), x is the cell percentages, and b is the bulk expression counts. In some instances, the matrix equation is solved by methods such as matrix algebra, regression analysis, and/or machine learning. Alternately or in combination, deconvolution methods comprise linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression (SVR). In some instances, deconvolution comprises a normalization step. Referring to FIG. 3, normalization may occur across a row or down a column. For example, normalization occurs across a row, wherein the row includes distinct cell statuses or down a column, wherein the column includes gene expression of a specific cell status. In some instances, normalization occurs across a row. In some instances, cell fractions are considered in determining gene expression (FIG. 3). In some instances, a deconvolution matrix is generated for each type of sample analyzed. For example, certain cell statuses have a different gene expression signature depending on the local tissue environment. As a result, a one-size-fits-all deconvolution matrix is sometimes less accurate than a deconvolution matrix "tailored" to a specific sample type. In some instances, the deconvolution algorithm maintains a database comprising a plurality of deconvolution matrices. In some instances, the deconvolution algorithm selects a deconvolution matrix for analyzing the gene expression data of a sample based on the sample type. The use of a tailored deconvolution matrix enables the use of a narrower set of genes for deconvolution of the sample. The narrower set of genes can increase speed of analysis and the number of samples that are processed at one time. In some instances, a smaller capture or bait set is used to enrich for the narrower set of genes for downstream analysis (e.g., RNA-Seq).

Methods and systems for determining cell status comprising methods relating to deconvolution may further comprise normalizing RNA content. In some instances, the RNA content is normalized or corrected based on cell type. In some instances, the RNA content is normalized or corrected based on cell status. For example, RNA content is normalized based on the amount of RNA in an individual cell type, or a cell having a particular status. In some instances, normalizing RNA content comprises determining a number of cells used to generate the RNA. In some instances, the number of cells is determined by flow cytometry, manual cell counting, automated cell counting, microscopy, or spectrophotometry. In some instances, the number of cells is at least or about 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, or more than 4 million cells.

Following determination of RNA content for an individual cell type or status, a correction value may be determined. In some instances, the cell is an immune cell. Examples of immune cells include, but are not limited to, a CD4+ T cell, a CD8+ T cell, a monocyte, a B-cell, a natural killer cell (NK), a M1 macrophage, or a M2 macrophage. In some instances, the immune cell is a CD4+ T cell. In some instances, the immune cell is a CD8+ T cell. In some instances, a correction value for each individual cell type is determined. In some instances, a correction value for each individual cell status is determined. In some instances, a correction value for each individual cell status of an individual cell type is determined.

The correction value may be used to identify percentages of individual cell statuses. In some instances, the correction value is used in combination with deconvolution methods to determine percentages of individual cell statuses. In some instances, the correction value is applied prior to deconvolution methods. For example, the correction value is applied prior to support vector regression of RNA sequence data. In some instances, the correction value is applied following support vector regression and the cell statuses have been deconvoluted.

Methods and systems for determining cell status comprising methods relating to deconvolution and normalizing RNA content may result in an accurate determination of immune cell status percentages in a sample. In some instances, the accuracy is at least or about 20%, 25%, 30%, 35%, 40%, 45%, 50%, 60%, 70%, 80%, 90%, 95%, or more than 95% improved using methods and systems as described herein as compared to methods and systems where RNA content is not normalized.

A final determination of the identity and quantity of cell statuses in a sample can be accomplished using deconvolution of expression data for a plurality of genes. Certain genes exhibit differential expression between two or more cell types that are evaluated using deconvolution. In some cases, the genes exhibit differential expression between cell states or statuses such as active, terminally exhausted, progenitor exhausted, naïve, central memory, effector memory, and stem cell memory cell states for T cells, between different types of immune cells, between immune cells of the same type and different state, between cancer cells of different states, between cancer cells of the same type and different state, or any combination thereof. Examples of genes for inclusion in a deconvolution matrix include those listed in Table 1 or Table 1B. In some instances, a deconvolution matrix comprises at least 10, 20, 30, 40, 50, 75, 100, or 125 genes or more. In some instances, a deconvolution matrix comprises no more than 10, 20, 30, 40, 50, 75, 100, or 125 genes. In some instances, a deconvolution matrix comprises at least 10, 20, 30, 40, 50, 60, 70, 80, 90, 100, 110, or 120 genes from Table 1. In some instances, a deconvolution matrix comprises no more than 10, 20, 30, 40, 50, 60, 70, 80, 90, 100, 110, or 120 genes from Table 1. In some embodiments, a deconvolution algorithm is used to identify cell status from RNA sequencing data. In some embodiments, the deconvolution algorithm comprises a panel of at least 1, 2, 3, 4, 5, 6, 7, 8, 9, 10, 15, 20, 25, 30, 40, 50, 60, 70, 80, 90, 100, or more genes selected from Table 1. In some embodiments, the deconvolution algorithm comprises a panel of at most 1, 2, 3, 4, 5, 6, 7, 8, 9, 10, 15, 20, 25, 30, 40, 50, 60, 70, 80, 90, 100, or more genes selected from Table 1. In some embodiments, the deconvolution algorithm comprises a panel of 1 gene to 100 genes, wherein the genes are selected from Table 1. In some instances, a deconvolution matrix comprises at least 5, 10, 15, 20, 25, 30, 35, or 40 genes from Table 1B. In some instances, a deconvolution matrix comprises no more than 5, 10, 15, 20, 25, 30, 35, or 40 genes from Table 1B. In some embodiments, a deconvolution algorithm is used to identify cell status from RNA sequencing data. In some embodiments, the deconvolution algorithm comprises a panel of at least 1, 2, 3, 4, 5, 6, 7, 8, 9, 10, 15, 20, 25, 30, or 40 or more genes selected from Table 1B. In some embodiments, the deconvolution algorithm comprises a panel of at most 1, 2, 3, 4, 5, 6, 7, 8, 9, 10, 15, 20, 25, 30, or 40, or more genes selected from Table 1B. In some embodiments, the deconvolution algorithm comprises a panel of 1 gene to 45 genes, wherein the genes are selected from Table 1B.

In some embodiments, the deconvolution algorithm comprises a panel of 1 gene to 2 genes, 1 gene to 3 genes, 1 gene to 4 genes, gene to 5 genes, 1 gene to 10 genes, 1 gene to 20 genes, 1 gene to 50 genes, 1 gene to 75 genes, 1 gene to 100 genes, 2 genes to 3 genes, 2 genes to 4 genes, 2 genes to 5 genes, 2 genes to 10 genes, 2 genes to 20 genes, 2 genes to 50 genes, 2 genes to 75 genes, 2 genes to 100 genes, 3 genes to 4 genes, 3 genes to 5 genes, 3 genes to 10 genes, 3 genes to 20 genes, 3 genes to 50 genes, 3 genes to 75 genes, 3 genes to 100 genes, 4 genes to 5 genes, 4 genes to 10 genes, 4 genes to 20 genes, 4 genes to 50 genes, 4 genes to 75 genes, 4 genes to 100 genes, 5 genes to 10 genes, 5 genes to 20 genes, 5 genes to 50 genes, 5 genes to 75 genes, 5 genes to 100 genes, 10 genes to 20 genes, 10 genes to 50 genes, 10 genes to 75 genes, 10 genes to 100 genes, 20 genes to 50 genes, 20 genes to 75 genes, 20 genes to 100 genes, 50 genes to 75 genes, 50 genes to 100 genes, or 75 genes to 100 genes, wherein the genes are selected from Table 1. In some embodiments, the deconvolution algorithm comprises a panel of 1 gene, 2 genes, 3 genes, 4 genes, 5 genes, 10 genes, 20 genes, 50 genes, 75 genes, or 100 genes. In some embodiments, the deconvolution algorithm comprises a panel of at least 1 gene, 2 genes, 3 genes, 4 genes, 5 genes, 10 genes, 20 genes, 50 genes, or 75 genes, wherein the genes are selected from Table 1. In some embodiments, the deconvolution algorithm comprises a panel of at most 2 genes, 3 genes, 4 genes, 5 genes, 10 genes, 20 genes, 50 genes, 75 genes, or 100 genes, wherein the genes are selected from Table 1.

In some embodiments, the deconvolution algorithm comprises a panel of 1 gene to 2 genes, 1 gene to 3 genes, 1 gene to 4 genes, 1 gene to 5 genes, 1 gene to 10 genes, 1 gene to 15 genes, 1 gene to 20 genes, gene to 30 genes, gene to 40 genes, 2 genes to 3 genes, 2 genes to 4 genes, 2 genes to 5 genes, 2 genes to 10 genes, 2 genes to 15 genes, 2 genes to 20 genes, 2 genes to 30 genes, 2 genes to 40 genes, 3 genes to 4 genes, 3 genes to 5 genes, 3 genes to 10 genes, 3 genes to 15 genes, 3 genes to 20 genes, 3 genes to 30 genes, 3 genes to 40 genes, 4 genes to 5 genes, 4 genes to 10 genes, 4 genes to 15 genes, 4 genes to 20 genes, 4 genes to 30 genes, 4 genes to 40 genes, 5 genes to 10 genes, 5 genes to 15 genes, 5 genes to 20 genes, 5 genes to 30 genes, 5 genes to 40 genes, 10 genes to 15 genes, 10 genes to 20 genes, 10 genes to 30 genes, 10 genes to 40 genes, 20 genes to 25 genes, 20 genes to 30 genes, 20 genes to 40 genes, 25 genes to 30 genes, 25 genes to 40 genes, or 25 genes to 40 genes, wherein the genes are selected from Table 1B. In some embodiments, the deconvolution algorithm comprises a panel of 1 gene, 2 genes, 3 genes, 4 genes, 5 genes, 10 genes, 15 genes, 20 genes, 30 genes, or 40 genes, wherein the genes are selected from Table 1B. In some embodiments, the deconvolution algorithm comprises a panel of at least 1 gene, 2 genes, 3 genes, 4 genes, 5 genes, 10 genes, 15 genes, 20 genes, or 30 genes, wherein the genes are selected from Table 1B. In some embodiments, the deconvolution algorithm comprises a panel of at most 2 genes, 3 genes, 4 genes, 5 genes, 10 genes, 15 genes, 20 genes, 30 genes, or 40 genes, wherein the genes are selected from Table 1B.

Provided herein are systems and methods for determining cell status using deconvolution methods, wherein following deconvolution, percentages of cells having a particular status may be determined. In some instances, a percentage output may describe how prevalent cell status is in an individual cell. For example, an individual cell may be 40% activated and 60% exhausted. In some instances, cells having a particular status may be further grouped based on shared lineage and percentages of cells based on lineage is determined. For example, immune cells are divided into T cells, CD4+ subtypes, myeloid cells, and natural killer cells. In some instances, cell statuses are dividing among different cell types, such CD4+ cells in an active state, CD4+ cells in a terminally exhausted state, CD4+ cells in a progenitor exhausted state, CD4+ cells in a naïve state, CD8+ cells in an active state, CD8+ cells in a terminally exhausted state, CD8+ cells in a progenitor exhausted state, and CD8+ cells in a naïve state. In some instances, percentages of non-immune cells are determined. In some instances, percentages of immune cells and percentages of non-immune cells are determined. Sometimes, determination of cellular status comprises determining a percentage of immune cells and non-immune cells such as tumor cells and/or stromal cells.

Following deconvolution, a number of cell statuses may be determined. In some instances, deconvolution identifies at least or about 2, 3, 4, 5, 6, 7, 8, 9, 10, 11, 12, 13, 14, 15, 16, 17, 18, 19, 20, or more than 20 cell statuses. In some instances, deconvolution identifies a range of about 5 to about 20 immune cell types. In some instances, deconvolution identifies at least or about 5 to 10, 5 to 15, 5 to 20, 10 to 15, 10 to 20, or 15 to 20 cell statuses. In some instances, deconvolution identifies at least or about 2, 3, 4, or 5 cell statuses.

Following deconvolution, a number of cell statuses of various immune and non-immune cell types may be determined. In some instances, deconvolution identifies at least or about 2, 3, 4, 5, 6, 7, 8, 9, 10, 11, 12, 13, 14, 15, 16, 17, 18, 19, 20, or more than 20 immune cell statuses. In some instances, deconvolution identifies a range of about 5 to about 20 immune cell statuses. In some instances, deconvolution identifies at least or about 5 to 10, 5 to 15, 5 to 20, 10 to 15, 10 to 20, or 15 to 20 immune cell statuses. In some instances, deconvolution identifies at least or about 1 to 5 immune cell statuses. Deconvolution may be used to identify non-immune cell statuses. In some instances, deconvolution identifies at least or about 2, 3, 4, 5, 6, 7, 8, 9, 10, 11, 12, 13, 14, 15, 16, 17, 18, 19, 20, or more than 20 non-immune cell status. In some instances, deconvolution identifies a range of about 5 to about 20 non-immune cell statuses. In some instances, deconvolution identifies at least or about 5 to 10, 5 to 15, 5 to 20, 10 to 15, 10 to 20, or 15 to 20 non-immune cell statuses. In some instances, deconvolution identifies at least or about 1 to 5 non-immune cell statuses.

In some cases, deconvolution results are evaluated by comparing to the Gold Standard. Sometimes, the Gold Standard is generated by sorting the samples evaluated by deconvolution. For example, a sample is split into two portions with one portion evaluated by nucleic acid sequencing and deconvolution and the other portion evaluated by sorting (e.g., flow cytometry or FACS) to obtain the Gold Standard. In some cases, the Gold Standard is supernatant cytokine measurement. In some cases, this cytokine measurement is done via enzyme-linked immunosorbent assay (ELISA.) The results of the deconvolution are then compared to the Gold Standard to evaluate for accuracy, specificity, sensitivity, correlation to the Gold Standard, or any combination thereof.

In some instances, deconvolved cell statuses and proportions (of the statuses) in a sample are calculated at an accuracy of at least 50%, 60%, 70%, 80%, 90%, 95%, 99% or more. In some instances, deconvolution is calculated at an accuracy of at least 50%, 60%, 70%, 80%, 90%, 95%, 99% or more for at least 100, 200, 300, 400, or 500 or more independent samples. In some instances, deconvolved cell statuses and proportions (of the statuses) in a sample are calculated at a sensitivity of at least 50%, 60%, 70%, 80%, 90%, 95%, 99% or more. In some instances, deconvolution is calculated at a sensitivity of at least 50%, 60%, 70%, 80%, 90%, 95%, 99% or more for at least 100, 200, 300, 400, or 500 or more independent samples. In some instances, deconvolved cell states/statuses and proportions (of the statuses) in a sample are calculated at a specificity of at least 50%, 60%, 70%, 80%, 90%[4], 95%, 99% or more. In some instances, deconvolution is calculated at a specificity of at least 50%, 60%, 70%, 80%, 90%, 95%, 99% or more for at least 100, 200, 300, 400, or 500 or more independent samples. In some instances, deconvolution has a correlation with the Gold Standard of at least 0.5, 0.6, 0.7, 0.8, 0.9, 0.95, 0.99 or more. In some instances, deconvolution has a correlation with the Gold Standard of at least 0.5, 0.6, 0.7, 0.8, 0.9, 0.95, 0.99 or more for at least 10, 200, 300, 400, or 500 or more independent samples Immune Modulatory Molecule Expression Determination Sequencing data as provided herein are used to determine gene expression. In some instances, the sequencing data is obtained from sequencing RNA from a sample. In some instances, the gene expression is of an immune modulatory molecule such as an immune checkpoint molecule or immune inhibitory molecule. Examples of immune modulatory molecules include, but are not limited to, one or more of 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD160, CD2, CD200R, CD226, CD26, CD27, CD28, CD30, CD39, CD40, CD48, CD70, CD73, CD80 (B7.1), CD86 (B7.2), CEACAM1, CGEN-15049, CTLA-4, DR3, GAL9, GITR, GITRL, HVEM, ICOS, ICOSL (B7H2), IDO1, IDO2, ILT-2 (LILRB1), ILT-4 (LILRB2), KIR, KLRG1, LAG3, LAIR1 (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA.

In some instances, the gene expression of a sample is compared to a reference sample. Sometimes, the systems and methods disclosed herein generate an immune-oncology profile comprising a visual representation of immune modulatory molecule gene expression. In some cases, the visual representation presents the gene expression of one or more immune modulatory molecules relative to a reference expression level. In some instances, the reference expression level is obtained from a reference sample. Sometimes, the reference sample comprises the same cell or tissue type as the sample being evaluated for gene expression. Sometimes, the gene expression of a sample is compared to an averaged or plurality of reference samples. As an example, a cancer sample being evaluated for gene expression is compared to average gene expression for reference samples of the same cancer type as the cancer sample in a reference database (e.g., TCGA database).

Cell Type and Ratio Determination

Provided herein are systems and methods for determining cell type and ratio in a sample using sequencing data. The sample often comprises a heterogeneous composition of different cell types and/or subtypes. Sometimes, the sample is a tumor sample. The cell types and/or subtypes that make up the sample includes one or more of cancer cells, non-cancer cells, and/or immune cells. Examples of non-immune cells include salivary gland cells, mammary gland cells, lacrimal gland cells, ceruminous gland cells, eccrine sweat gland cells, apocrine sweat gland cells, sebaceous gland cells, Bowman's gland cells. Brunner's gland cells, prostate gland cells, seminal vesicle cells, bulbourethral gland cells, keratinizing epithelial cells, hair shaft cells, epithelial cells, exocrine secretory epithelial cells, uterus endometrium cells, isolated goblet cells of respiratory and digestive tracts, stomach lining mucous cells, hormone secreting cells, pituitary cells, gut and respiratory tract cells, thyroid gland cells, adrenal gland cells, chromaffin cells, Leydig cells, theca interna cells, macula densa cells of kidney, peripolar cells of kidney, mesangial cells of kidney, hepatocytes, white fat cells, brown fat cells, liver lipocytes, kidney cells, kidney glomerulus parietal cells, kidney glomerulus podocytes, kidney proximal tubule brush border cells, loop of Henle thin segment cells, kidney distal tubule cells, endothelial fenestrated cells, vascular endothelial continuous cells, synovial cells, serosal cells, squamous cells, columnar cells of endolymphatic sac with microvilli, columnar cells of endolymphatic sac without microvilli, vestibular membrane cells, stria vascularis basal cells, stria vascularis marginal cells, choroid plexus cells, respiratory tract ciliated cells, oviduct ciliated cells, uterine endometrial ciliated cells, rete testis ciliated cells, ductulus efferens ciliated cells, ciliated ependymal cells of central nervous system, organ of Corti interdental epithelial cells, loose connective tissue fibroblasts, corneal fibroblasts, tendon fibroblasts, bone marrow reticular tissue fibroblasts, other nonepithelial fibroblasts, pericytes, skeletal muscle cells, red skeletal muscle cells, white skeletal muscle cells, intermediate skeletal muscle cells, nuclear bag cells of muscle spindle, nuclear chain cells of muscle spindle, satellite cells, cardiac muscle cells, ordinary cardiac muscle cells, nodal cardiac muscle cells, purkinje fiber cells, smooth muscle cells, myoepithelial cells of iris, myoepithelial cells of exocrine glands, erythrocytes, megakaryocytes, monocytes, epidermal Langerhans cells, osteoclasts, sensory neurons, olfactory receptor neurons, pain-sensitive primary sensory neurons, photoreceptor cells of retina in eye, photoreceptor rod cells, proprioceptive primary sensory neurons (various types), touch-sensitive primary sensory neurons, taste bud cells, autonomic neuron cells, Schwann cells, satellite cells, glial cells, astrocytes, oligodendrocytes, melanocytes, germ cells, nurse cells, interstitial cells, and pancreatic duct cells. Various cell types may be determined for the sample using methods as described herein including, but not limited to, lymphoid cells, stromal cells, stem cells, and myeloid cells. In some instances, the cells are stromal cells, for example, mesenchymal stem cells, adipocytes, preadipocytes, stromal cells, fibroblasts, pericytes, endothelial cells, microvascular endothelial cells, lymphatic endothelial cells, smooth muscle cells, chondrocytes, osteoblasts, skeletal muscle cells, myocytes. Examples of stem cells include, but are not limited to, hematopoietic stem cells, common lymphoid progenitor cells, common myeloid progenitor cells, granulocyte-macrophage progenitor cells, megakaryocyte-erythroid progenitor cells, multipotent progenitor cells, megakaryocytes, erythrocytes, and platelets. Examples of myeloid cells include, but are not limited to, monocytes, macrophages, macrophages M1, macrophages M2, dendritic cells, conventional dendritic cells, plasmacytoid dendritic cells, immature dendritic cells, neutrophils, eosinophils, mast cells, and basophils. Other cell types may be determined using methods as described herein, for example, epithelial cells, sebocytes, keratinocytes, mesangial cells, hepatocytes, melanocytes, keratocytes, astrocytes, and neurons.

In some instances, the sequencing data is used to determine immune cell expression. Examples of immune cells to be detected by methods described herein include, but are not limited to, CD4+ memory T-cells. CD4+ naive T-cells, CD4+ T-cells, central memory T (Tcm) cells, effector memory T (Tem) cells, CD4+ Tcm, CD4+ Tem CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the sequencing data is used to determine expression of non-immune cells including, but not limited to, stromal cells, stem cells, or tumor cells.

Methods and systems for determining cell type and ratio may comprise determining gene expression. In some instances, determining cell type and ratio may further comprise methods relating to deconvolution. In some instances, a deconvolution matrix is used. The deconvolution matrix typically comprises gene expression for one or more cell types. In some instances, the matrix is used for a complex data set of RNA sequencing gene expression data to allow for identification of cell types in the data and the relative proportions of each cell type. Se FIG. 3. In some instances, individual cell types/subtypes and the relative proportion of these individual cell types/subtypes are determined from sequencing data using a deconvolution matrix. In some cases, the relative proportion of at least 2 cell types/subtypes, at least 3 cell types/subtypes, at least 4 cell types/subtypes, at least 5 cell types/subtypes, at least 6 cell types/subtypes, at least 7 cell types/subtypes, at least 8 cell types/subtypes, at least 9 cell types/subtypes, at least 10 cell types/subtypes, at least 11 cell types/subtypes, at least 12 cell types/subtypes, at least 13 cell types/subtypes, at least 14 cell types/subtypes, at least 15 cell types/subtypes, at least 16 cell types/subtypes, at least 17 cell types/subtypes, at least 18 cell types/subtypes, at least 19 cell types/subtypes, at least 20 cell types/subtypes, at least 21 cell types/subtypes, at least 22 cell types/subtypes, at least 23 cell types/subtypes, or at least 24 cell types are determined from sequencing data using a deconvolution matrix. A matrix equation illustrates the mathematical relationship between a matrix comprising expression signatures of individual cell types, the percentage of each cell type, and the bulk expression counts. In some instances, the matrix equation is Ax=b, where A is the cell expression fingerprints (i.e., deconvolution matrix), x is the cell percentages, and b is the bulk expression counts. In some instances, the matrix equation is solved by methods such as matrix algebra, regression analysis, and/or machine learning. Alternately or in combination, deconvolution methods comprise linear least-squares regression (LLSR), quadratic programming (QP), perturbation model for gene expression deconvolution (PERT), robust linear regression (RLR), microarray microdissection with analysis of differences (MMAD), digital sorting algorithm (DSA), or support vector regression (SVR). In some instances, deconvolution comprises a normalization step. Referring to FIG. 3, normalization may occur across a row or down a column. For example, normalization occurs across a row, wherein the row includes distinct cell statuses or down a column, wherein the column includes gene expression of cells for a specific cell status. In some instances, normalization occurs across a row. In some instances, cell fractions are considered in determining gene expression (FIG. 3). In some instances, a deconvolution matrix is generated for each type of sample analyzed. For example, certain cell statuses have a different gene expression signature depending on the local tissue environment. As a result, a one-size-fits-all deconvolution matrix is sometimes less accurate than a deconvolution matrix "tailored" to a specific sample type. In some instances, the deconvolution algorithm maintains a database comprising a plurality of deconvolution matrices. In some instances, the deconvolution algorithm selects a deconvolution matrix for analyzing the gene expression data of a sample based on the sample type. The use of a tailored deconvolution matrix enables the use of a narrower set of genes for deconvolution of the sample. The narrower set of genes can increase speed of analysis and the number of samples that are processed at one time. In some instances, a smaller capture or bait set is used to enrich for the narrower set of genes for downstream analysis (e.g., RNA-Seq).

Methods and systems for determining cell type and ratio comprising methods relating to deconvolution may further comprise normalizing RNA content. In some instances, the RNA content is normalized or corrected based on cell type. For example, RNA content is normalized based on the amount of RNA in an individual cell type. In some instances, normalizing RNA content comprises determining a number of cells used to generate the RNA. In some instances, the number of cells is determined by flow cytometry, manual cell counting, automated cell counting, microscopy, or spectrophotometry. In some instances, the number of cells is at least or about 30,000 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, or more than 4 million cells.

Following determination of RNA content for an individual cell type, a correction value may be determined. In some instances, the cell is an immune cell. Examples of immune cells include, but are not limited to, a CD4+ T cell, a CD8+ T cell, a monocyte, a B-cell, a natural killer cell (NK), a M1 macrophage, or a M2 macrophage. In some instances, the immune cell is a CD4+ T cell. In some instances, a correction value for each individual cell type is determined. For example, the cell correction value for CD4+ T cell is about 1.0). Sometimes, the cell correction value for CD4+ T cell is from 0.9 to 1.1. In some instances, the cell correction value for CD8+ T cell is about 1.03. Sometimes, the cell correction value for CD8+ T cell is from 0.93 to 1.13. In some instances, the cell correction value for a monocyte is about 1.35. Sometimes, the cell correction value for a monocyte is from 1.25 to 1.45. In some instances, the cell correction value for a B-cell is about 0.53. Sometimes, the cell correction value for a B-cell is from 0.43 to 0.63. In some instances, the cell correction value for a natural killer cell (NK) is about 0.47. Sometimes, the cell correction value for a NK cell is from 0.37 to 0.57. In some instances, the cell correction value for a M1 macrophage is about 7.59. Sometimes, the cell correction value for a M1 macrophage is from 6.59 to 8.59. In some instances, the cell correction value for a M2 macrophage is about 12.26. Sometimes, the cell correction value for a M2 macrophage is from 11.26 to 13.26.

The correction value may be used to identify cell percentages of individual cell types. In some instances, the correction value is used in combination with deconvolution methods to determine cell percentages of individual cell types. In some instances, the correction value is applied prior to deconvolution methods. For example, the correction value is applied prior to support vector regression of RNA sequence data. In some instances, the correction value is applied following support vector regression and the cell types have been deconvoluted.

Methods and systems for determining cell type and ratio comprising methods relating to deconvolution and normalizing RNA content may result in an accurate determination of immune cell type percentages in a sample. In some instances, the accuracy is at least or about 20%, 25%, 30%, 35%, 40%, 45%, 50%, 60%, 70%, 80%, 90%, 95%, or more than 95% improved using methods and systems as described herein as compared to methods and systems where RNA content is not normalized.

An immune-oncology profile may comprise the cell types/subtypes and ratios present in a sample using deconvolution of expression data for a plurality of genes. The genes typically exhibit differential expression in at least two cell types/subtypes that are evaluated using deconvolution. In some cases, the genes exhibit differential expression between cancer and non-cancer cells, between different types of cancer cells, between immune and non-immune cells, between different types of immune cells, between different types of non-cancer cells, between different subtypes of any of the foregoing, or any combination thereof. Examples of genes for inclusion in a deconvolution matrix include those listed in Tables 2A-2E. In some instances, a deconvolution matrix comprises at least about 10, 20, 30, 40, 50, or 100 genes. In some instances, a deconvolution matrix comprises no more than about 10, 20, 30, 40, 50, or 100 genes. In some instances, a deconvolution matrix comprises at least about 10, 20, 30, 40, 50, 60, 70, 80, 90, 100, 110, or about 120 genes from one or more of Tables 2A-2E. In some instances, a deconvolution matrix comprises no more than about 10, 20, 30, 40, 50, 60, 70, 80, 90, 100, 110, or about 120 genes from Tables 2A-2E.

TABLE 2A

Deconvolution Genes for CD4+ T-cells

| | | | |
|---|---|---|---|
| ALS2CL | ANKRD55 | ZNF483 | TRAV13-1 |
| ST6GALNAC1 | SEMA3A | TRBV5-4 | DNAH8 |
| IL2RA | TRBV11-2 | TRAV8-2 | KRT72 |
| EPPK1 | FAM153B | TRAV12-2 | TRAV8-6 |
| TRBV6-5 | TRAV10 | IGKV5-2 | IGLV6-57 |

TABLE 2A-continued

Deconvolution Genes for CD4+ T-cells

| | | | |
|---|---|---|---|
| TRAV12-1 | CTLA4 | TSHZ2 | FOXP3 |
| IGHV4-28 | TRAV2 | SORCS3 | TRAV5 |
| MDS2 | NTN4 | IGLV10-54 | DACT1 |
| TRBV5-5 | THEM5 | HPCAL4 | CD4 |

TABLE 2B

Deconvolution Genes for CD8+ T-cells

| | | | |
|---|---|---|---|
| FLT4 | TRBV4-2 | TRBV6-4 | SPRY2 |
| S100B | TNIP3 | CD248 | ROBO1 |
| CD8B | TRBV2 | CYP4F22 | PZP |
| LAG3 | KLRC4-KLRK1 | CRTAM | SHANK1 |
| ANAPC1P1 | NRCAM | JAKMIP1 | KLRC2 |
| KLRC3 | CD8A | TRAV4 | FBLN2 |

TABLE 2C

Deconvolution Genes for Monocytes

| | | | |
|---|---|---|---|
| DES | HLX | FPR3 | FCGR1B |
| LOXHD1 | EPHB2 | LPL | LIPN |
| AQP9 | MILR1 | RETN | GPNMB |
| CYP2S1 | PDK4 | ULRA6 | SEPT10 |
| PLA2G4A | FOLR2 | FOLR3 | C1QB |
| SLC6A12 | SLC22A16 | DOCK1 | NRG1 |
| RXFP2 | RIN2 | ARHGEF10L | |
| LPAR1 | CES1 | FPR2 | |

TABLE 2D

Deconvolution Genes for NIC cells

| | | | |
|---|---|---|---|
| IGFBP7 | LDB2 | GUCY1A3 | KLRF1 |
| DTHD1 | AKR1C3 | FASLG | KLRC1 |
| XCL1 | DAB2 | FAT4 | CD160 |
| BNC2 | CXCR1 | SIGLEC17P | SH2D1B |
| DGKK | ZMAT4 | LGALS9B | NMUR1 |
| LGALS9C | MLC1 | LIM2 | |
| NCR1 | CCNJL | PCDH1 | |

TABLE 2E

Deconvolution Genes for B-cells

| | | | |
|---|---|---|---|
| UGT8 | IGKV1OR2-108 | IGHE | SCN3A |
| IGLV2-8 | IGKV1D-16 | MYO5B | ENAM |
| RP11-148O21.2 | IGLC7 | IGHV1-2 | IGKJ5 |
| SOX5 | TNFRSF13B | IGKV2D-29 | IGKV1-17 |
| IGLV2-18 | IGHV2-70 | CHL1 | |
| IGKV3D-20 | IGLV8-61 | IGKV6-21 | |

There are potentially around 19,700 possible gene identifiers that can be used from the transcriptome for generating a basis or deconvolution matrix. In some instances, genes are selected for deconvolution if the genes are differentially expressed in pairwise cell type differential expression analysis. In some instances, genes are selected for deconvolution if the genes are expressed at a consistent level within a cell type across samples. The present disclosure has identified a small subset of the transcriptome as being useful for carrying out deconvolution of immune cell types. Table 3 shows a list of 293 total genes and corresponding Ensembl gene identifiers in a 15 differentially expressed gene list. The genes in Table 3 are generated by performing pairwise comparisons for each cell type and tallying up the top 15 differentially expressed genes in each comparison.

TABLE 3

Top Differentially Expressed Genes

| gene_id | gene_name |
|---|---|
| ENSG00000128203.6 | ASPHD2 |
| ENSG00000171777.14 | RASGRP4 |
| ENSG00000186469.7 | GNG2 |
| ENSG00000186806.5 | VSIG10L |
| ENSG00000198894.5 | CIPC |
| ENSG00000156475.17 | PPP2R2B |
| ENSG00000178199.12 | ZC3H12D |
| ENSG00000206190.10 | ATP10A |
| ENSG00000117090.13 | SLAMF1 |
| ENSG00000263528.6 | IKBKE |
| ENSG00000198851.8 | CD3E |
| ENSG00000100351.15 | GRAP2 |
| ENSG00000146285.12 | SCML4 |
| ENSG00000197208.5 | SLC22A4 |
| ENSG00000126217.19 | MCF2L |
| ENSG00000186827.9 | TNFRSF4 |
| ENSG00000111913.14 | FAM65B |
| ENSG00000182183.13 | FAM159A |
| ENSG00000175489.9 | LRRC25 |
| ENSG00000170962.11 | PDGFD |
| ENSG00000104974.9 | LILRA1 |
| ENSG00000185883.9 | ATP6V0C |
| ENSG00000151490.12 | PTPRO |
| ENSG00000157445.13 | CACNA2D3 |
| ENSG00000184060.9 | ADAP2 |
| ENSG00000172243.16 | CLEC7A |
| ENSG00000158869.9 | FCER1G |
| ENSG00000100427.14 | MLC1 |
| ENSG00000150045.10 | KLRF1 |
| ENSG00000018280.15 | SLC11A1 |
| ENSG00000122223.11 | CD244 |
| ENSG00000176928.5 | GCNT4 |
| ENSG00000162599.14 | NFIA |
| ENSG00000131042.12 | LILRB2 |
| ENSG00000164398.11 | ACSL6 |
| ENSG00000160683.4 | CXCR5 |
| ENSG00000102445.17 | KIAA0226L |
| ENSG00000160883.9 | HK3 |
| ENSG00000198816.5 | ZNF358 |
| ENSG00000179041.3 | RRS1 |
| ENSG00000053524.10 | MCF2L2 |
| ENSG00000102245.6 | CD40LG |
| ENSG00000124203.5 | ZNF831 |
| ENSG00000137441.7 | FGFBP2 |
| ENSG00000109944.9 | C11orf63 |
| ENSG00000183813.6 | CCR4 |
| ENSG00000198879.10 | SFMBT2 |
| ENSG00000173208.3 | ABCD2 |
| ENSG00000144843.10 | ADPRH |
| ENSG00000183621.14 | ZNF438 |
| ENSG00000174946.6 | GPR171 |
| ENSG00000066056.12 | TIE1 |
| ENSG00000176438.11 | SYNE3 |
| ENSG00000153283.11 | CD96 |
| ENSG00000167286.8 | CD3D |
| ENSG00000179934.6 | CCR8 |
| ENSG00000127507.16 | EMR2 |
| ENSG00000167850.3 | CD300C |
| ENSG00000197629.5 | MPEG1 |
| ENSG00000100385.12 | IL2RB |
| ENSG00000133561.14 | GIMAP6 |
| ENSG00000179921.13 | GPBAR1 |
| ENSG00000263264.1 | CTB-133G6.1 |
| ENSG00000152213.3 | ARL11 |
| EN5G00000077420.14 | APBB1IP |
| ENSG00000145416.12 | 1-Mar |
| ENSG00000095585.15 | BLNK |
| ENSG00000158714.9 | SLAMF8 |
| ENSG00000188822.7 | CNR2 |
| ENSG00000030419.15 | IKZF2 |
| ENSG00000151366.11 | NDUFC2 |
| ENSG00000121964.13 | GTDC1 |

TABLE 3-continued

Top Differentially Expressed Genes

| gene_id | gene_name |
| --- | --- |
| ENSG00000126264.8 | HCST |
| ENSG00000010030.12 | ETV7 |
| ENSG00000186265.8 | BTLA |
| ENSG00000187796.12 | CARD9 |
| ENSG00000182866.15 | LCK |
| ENSG00000100450.11 | GZMH |
| ENSG00000158473.6 | CD1D |
| ENSG00000149970.13 | CNKSR2 |
| ENSG00000104490.16 | NCALD |
| ENSG00000107954.9 | NEURL1 |
| ENSG00000155846.15 | PPARGC1B |
| ENSG00000003400.13 | CASP10 |
| ENSG00000115956.9 | PLEK |
| ENSG00000175556.15 | LONRF3 |
| ENSG00000187116.12 | LILRA5 |
| ENSG00000165591.6 | FAAH2 |
| ENSG00000140090.16 | SLC24A4 |
| ENSG00000010319.5 | SEMA3G |
| ENSG00000136573.11 | BLK |
| ENSG00000155629.13 | PIK3AP1 |
| ENSG00000177455.10 | CD19 |
| ENSG00000152495.9 | CAMK4 |
| ENSG00000117091.8 | CD48 |
| ENSG00000170819.4 | BFSP2 |
| ENSG00000198821.9 | CD247 |
| ENSG00000173762.6 | CD7 |
| ENSG00000120278.13 | PLEKHG1 |
| ENSG00000119866.19 | BCL11A |
| ENSG00000120594.15 | PLXDC2 |
| ENSG00000145649.7 | GZMA |
| ENSG00000158517.12 | NCF1 |
| ENSG00000180061.8 | TMEM150B |
| ENSG00000127152.16 | BCL11B |
| ENSG00000116824.4 | CD2 |
| ENSG00000170458.12 | CD14 |
| ENSG00000090376.7 | IRAK3 |
| ENSG00000000938.11 | FGR |
| ENSG00000143184.4 | XCL1 |
| ENSG00000180739.13 | S1PR5 |
| ENSG00000012124.13 | CD22 |
| ENSG00000177272.8 | KCNA3 |
| ENSG00000172673.9 | THEMIS |
| ENSG00000273749.3 | CYFIP1 |
| ENSG00000278540.3 | ACACA |
| ENSG00000136404.14 | TM6SF1 |
| ENSG00000086730.15 | LAT2 |
| ENSG00000255587.6 | RAB44 |
| ENSG00000163519.12 | TRAT1 |
| ENSG00000198734.9 | F5 |
| ENSG00000117322.15 | CR2 |
| ENSG00000065675.13 | PRKCQ |
| ENSG00000198574.5 | SH2D1B |
| ENSG00000187912.10 | CLEC17A |
| ENSG00000267534.2 | S1PR2 |
| ENSG00000119535.16 | CSF3R |
| ENSG00000166523.6 | CLEC4E |
| ENSG00000164330.15 | EBF1 |
| ENSG00000163563.7 | MNDA |
| ENSG00000179088.13 | C12orf42 |
| ENSG00000145687.14 | SSBP2 |
| ENSG00000205544.3 | TMEM256 |
| ENSG00000172543.6 | CTSW |
| ENSG00000124406.15 | ATP8A1 |
| ENSG00000136867.9 | SLC31A2 |
| ENSG00000113263.11 | ITK |
| ENSG00000172578.10 | KLHL6 |
| ENSG00000119457.7 | SLC46A2 |
| ENSG00000153485.5 | TMEM251 |
| ENSG00000203710.9 | CR1 |
| ENSG00000175294.5 | CATSPER1 |
| ENSG00000111452.11 | GPR133 |
| ENSG00000160654.8 | CD3G |
| ENSG00000189430.11 | NCR1 |
| ENSG00000197705.8 | KLHL14 |
| ENSG00000089012.13 | SIRPG |
| ENSG00000181409.10 | AATK |
| EN5G00000112394.15 | SLC16A10 |
| EN5G00000105369.8 | CD79A |
| ENSG00000146373.15 | RNF217 |
| ENSG00000152969.15 | JAKMIP1 |
| ENSG00000146776.13 | ATXN7L1 |
| ENSG00000068831.17 | RASGRP2 |
| ENSG00000186891.12 | TNFRSF18 |
| ENSG00000155307.16 | SAMSN1 |
| ENSG00000183023.17 | SLC8A1 |
| ENSG00000240891.5 | PLCXD2 |
| ENSG00000175857.7 | GAPT |
| ENSG00000103313.10 | MEFV |
| ENSG00000100365.13 | NCF4 |
| ENSG00000164483.15 | SAMD3 |
| ENSG00000125810.9 | CD93 |
| ENSG00000178562.16 | CD28 |
| ENSG00000151948.10 | GLT1D1 |
| ENSG00000153563.14 | CD8A |
| ENSG00000134460.14 | IL2RA |
| ENSG00000132185.15 | FCRLA |
| ENSG00000152582.15 | SPEF2 |
| ENSG00000101842.12 | VSIG1 |
| ENSG00000168229.3 | PTGDR |
| ENSG00000203747.8 | FCGR3A |
| ENSG00000011600.10 | TYROBP |
| ENSG00000085514.14 | PILRA |
| ENSG00000104972.13 | LILRB1 |
| ENSG00000065413.15 | ANKRD44 |
| ENSG00000196220.14 | SRGAP3 |
| ENSG00000162415.6 | ZSWIM5 |
| ENSG00000167984.15 | NLRC3 |
| ENSG00000178573.6 | MAF |
| ENSG00000173258.11 | ZNF483 |
| ENSG00000187554.10 | TLR5 |
| ENSG00000069020.17 | MAST4 |
| ENSG00000181036.12 | FCRL6 |
| ENSG00000172456.15 | FGGY |
| ENSG00000010671.14 | BTK |
| ENSG00000114013.14 | CD86 |
| ENSG00000144218.17 | AFF3 |
| ENSG00000104043.13 | ATP8B4 |
| ENSG00000129450.7 | SIGLEC9 |
| ENSG00000082074.14 | FYB |
| ENSG00000153064.10 | BANK1 |
| ENSG00000164867.9 | NOS3 |
| ENSG00000143226.12 | FCGR2A |
| ENSG00000011590.12 | ZBTB32 |
| ENSG00000160185.12 | UBASH3A |
| ENSG00000163393.11 | SLC22A15 |
| ENSG00000133574.8 | GIMAP4 |
| ENSG00000196218.10 | RYR1 |
| ENSG00000128218.7 | VPREB3 |
| ENSG00000181847.10 | TIGIT |
| ENSG00000155849.14 | ELMO1 |
| ENSG00000182621.15 | PLCB1 |
| ENSG00000148655.13 | C10orf11 |
| ENSG00000128815.16 | WDFY4 |
| ENSG00000188404.7 | SELL |
| ENSG00000100368.12 | CSF2RB |
| ENSG00000141293.14 | SKAP1 |
| ENSG00000213047.10 | DENND1B |
| ENSG00000196418.11 | ZNF124 |
| ENSG00000113319.10 | RASGRF2 |
| ENSG00000140968.9 | IRF8 |
| ENSG00000066294.13 | CD84 |
| ENSG00000188848.14 | BEND4 |
| ENSG00000183208.13 | SH2D1A |
| ENSG00000236609.3 | ZNF853 |
| ENSG00000165521.14 | EML5 |
| ENSG00000013725.13 | CD6 |
| ENSG00000110002.14 | VWA5A |
| ENSG00000134539.15 | KLRD1 |
| ENSG00000170006.10 | TMEM154 |
| ENSG00000042980.11 | ADAM28 |
| ENSG00000142303.12 | ADAMTS10 |
| ENSG00000162881.6 | OXER1 |

TABLE 3-continued

Top Differentially Expressed Genes

| gene_id | gene_name |
|---|---|
| ENSG00000150681.8 | RGS18 |
| ENSG00000103569.8 | AQP9 |
| ENSG00000186074.17 | CD300LF |
| ENSG00000172116.20 | CD8B |
| ENSG00000100055.19 | CYTH4 |
| ENSG00000170909.12 | OSCAR |
| ENSG00000035720.6 | STAP1 |
| ENSG00000139193.3 | CD27 |
| ENSG00000066336.10 | SPI1 |
| ENSG00000110448.9 | CD5 |
| ENSG00000184221.11 | OLIG1 |
| ENSG00000005471.14 | ABCB4 |
| ENSG00000105227.13 | PRX |
| ENSG00000145990.9 | GFOD1 |
| ENSG00000159339.12 | PADI4 |
| ENSG00000105374.8 | NKG7 |
| ENSG00000235568.5 | NFAM1 |
| ENSG00000110777.10 | POU2AF1 |
| ENSG00000154655.13 | L3MBTL4 |
| ENSG00000158481.11 | CD1C |
| ENSG00000140678.15 | ITGAX |
| ENSG00000146094.12 | DOK3 |
| ENSG00000117009.10 | KMO |
| ENSG00000164124.9 | TMEM144 |
| ENSG00000247077.5 | PGAM5 |
| ENSG00000132704.14 | FCRL2 |
| ENSG00000107242.16 | PIP5K1B |
| ENSG00000142235.7 | LMTK3 |
| ENSG00000186854.9 | TRABD2A |
| ENSG00000196159.10 | FAT4 |
| ENSG00000106034.16 | CPED1 |
| ENSG00000154451.13 | GBP5 |
| ENSG00000167995.14 | BEST1 |
| ENSG00000151623.13 | NR3C2 |
| ENSG00000112182.13 | BACH2 |
| ENSG00000124772.10 | CPNES |
| ENSG00000221926.10 | TRIM16 |
| ENSG00000130810.18 | PPAN |
| ENSG00000049768.13 | FOXP3 |
| ENSG00000198223.13 | CSF2RA |
| ENSG00000271383.5 | NBPF19 |
| ENSG00000079263.17 | SP140 |
| ENSG00000073861.2 | TBX21 |
| ENSG00000105383.13 | CD33 |
| ENSG00000111052.6 | LIN7A |
| ENSG00000196092.11 | PAX5 |
| ENSG00000171051.7 | FPR1 |
| ENSG00000162654.8 | GBP4 |
| ENSG00000159958.4 | TNFRSF13C |
| ENSG00000010610.8 | CD4 |
| ENSG00000126759.11 | CFP |
| ENSG00000104921.13 | FCER2 |
| ENSG00000160856.19 | FCRL3 |
| ENSG00000080493.12 | SLC4A4 |
| ENSG00000186462.8 | NAP1L2 |
| ENSG00000261371.4 | PECAM1 |
| ENSG00000085265.9 | FCN1 |
| ENSG00000205730.6 | ITPRIPL2 |
| ENSG00000266412.4 | NCOA4 |
| ENSG00000087903.11 | RFX2 |
| ENSG00000161405.15 | IKZF3 |
| ENSG00000144152.11 | FBLN7 |
| ENSG00000165071.13 | TMEM71 |
| ENSG00000265808.3 | SEC22B |
| ENSG00000162804.12 | SNED1 |
| ENSG00000105967.14 | TFEC |
| ENSG00000197540.6 | GZMM |
| ENSG00000090612.19 | ZNF268 |
| ENSG00000171596.6 | NMUR1 |

Provided herein are systems and methods for determining an immune-oncology profile comprising determining cell type and ratio using deconvolution methods, wherein following deconvolution, percentages of immune cells may be determined. In some instances, immune cells may be further grouped based on shared lineage and percentages of immune cells based on lineage is determined. For example, immune cells are divided into T cells, CD4+ subtypes, myeloid cells, and natural killer cells. In some instances, percentages of non-immune cells are determined. In some instances, percentages of immune cells and percentages of non-immune cells are determined. Sometimes, an immune-oncology profile comprises determining a percentage of immune cells and non-immune cells such as tumor cells and/or stromal cells.

Following deconvolution, a number of cell types of various immune and non-immune cell types may be determined. In some instances, deconvolution identifies at least or about 2, 3, 4, 5, 6, 7, 8, 9, 10, 11, 12, 13, 14, 15, 16, 17, 18, 19, 20, or more than 20 immune cell types. In some instances, deconvolution identifies a range of about 5 to about 20 immune cell types. In some instances, deconvolution identifies at least or about 5 to 10, 5 to 15, 5 to 20, 10 to 15, 10 to 20, or 15 to 20 immune cell types. Deconvolution may be used to identify non-immune cell types. In some instances, deconvolution identifies at least or about 2, 3, 4, 5, 6, 7, 8, 9, 10, 11, 12, 13, 14, 15, 16, 17, 18, 19, 20, or more than 20 non-immune cell types. In some instances, deconvolution identifies a range of about 5 to about 20 non-immune cell types. In some instances, deconvolution identifies at least or about 5 to 10, 5 to 15, 5 to 20, 10 to 15, 10 to 20, or 15 to 20 non-immune cell types. In some cases, deconvolution results are evaluated by comparing to the Gold Standard. Sometimes, the Gold Standard is generated by sorting the samples evaluated by deconvolution. For example, a sample is split into two portions with one portion evaluated by nucleic acid sequencing and deconvolution and the other portion evaluated by sorting (e.g., flow cytometry or FACS) to obtain the Gold Standard. The results of the deconvolution are then compared to the Gold Standard to evaluate for accuracy, specificity, sensitivity, correlation to the Gold Standard, or any combination thereof.

In some instances, deconvolved cell identities and proportions (of the identities) in a sample are calculated at an accuracy of at least 50%, 60%, 70%, 80%, 90%, 95%, 99% or more. In some instances, deconvolution is calculated at an accuracy of at least 50%, 60%, 70%, 80%, 90%, 95%, 99% or more for at least 100, 200, 300, 400, or 500 or more independent samples. In some instances, deconvolved cell identities and proportions (of the identities) in a sample are calculated at a sensitivity of at least 50%, 60%, 70%, 80%, 90%, 95%, 99% or more. In some instances, deconvolution is calculated at a sensitivity of at least 50%, 60%, 70%, 80%, 90%, 95%, 99% or more for at least 100, 200, 300, 400, or 500 or more independent samples. In some instances, deconvolved cell identities and proportions (of the identities) in a sample are calculated at a specificity of at least 50%, 60%, 70%, 80%, 90%, 95%, 99% or more. In some instances, deconvolution is calculated at a specificity of at least 50%, 60%, 70%, 80%, 90%, 95%, 99% or more for at least 100, 200, 300, 400, or 500 or more independent samples. In some instances, deconvolution has a correlation with the Gold Standard of at least 0.5, 0.6, 0.7, 0.8, 0.9, 0.95, 0.99 or more. In some instances, deconvolution has a correlation with the Gold Standard of at least 0.5, 0.6, 0.7, 0.8, 0.9, 0.95, 0.99 or more for at least 100, 200, 300, 400, or 500 or more independent samples. Therapeutic Applications Provided herein are methods and systems of optimizing an immunotherapy regimen. In some instances, the method utilizes RNA sequencing data from a sample obtained from a subject. In some instances, the subject is being treated with an immunotherapy regimen. In some instances, a deconvolution algorithm is applied to at least a subset of the RNA sequencing data. In some instances, an amount or percentage of exhausted T-cells in the sample is identified and quantified. In some instances, this is accomplished by analyzing the expression levels of one or more exhaustion status signature genes. In some instances, if the sample displays an elevated level of exhausted T-cells, then an alternative therapy is recommended. In some instances, if the sample does not display an elevated level of exhausted T-cells, continuing with the immunotherapy regimen is recommended.

The immunotherapy regimen may be any type of immunotherapy. An immunotherapy utilizes some portion of the immune system to treat an ailment in a subject. In some instances, the immunotherapy utilizes a subject's immune system to treat a disease. In some instances, the immunotherapy regiment comprises an immune cell therapy, a cancer vaccine, a cytokine therapy, an antibody therapy, or any combination thereof. In some instances, the immunotherapy is administered to a subject in need thereof.

In some instances, the immunotherapy comprises an immune cell therapy. In some instances, the immune cell therapy is a chimeric antigen receptor T-Cell (CAR-T) therapy, tumor-infiltrating lymphocyte (TIL) therapy, engineered T-cell receptor (TCR) therapy, or natural killer (NK) cell therapy. In some instances, the immune cell therapy is CAR-macrophage therapy or CAR-natural killer therapy. In some instances, the immune cell therapy is CAR-T therapy. In some instances, the CAR-T therapy is axicabtagene ciloleucel or tisagenlecleucel. In some instances, the immune cell therapy is a CD19-targeting therapy.

In some instances, the immunotherapy is a cancer vaccine. In some embodiments, the cancer vaccine comprises an oncolytic virus.

In some instances, the immunotherapy is a cytokine therapy. In some embodiments, the cytokine therapy comprises a chemokine, an interferon, an interleukin, a lymphokine, a tumor necrosis factor, or any combination thereof.

In some instances, the immunotherapy is an antibody therapy. In some instances, the antibody therapy comprises tumor targeting monoclonal antibodies, immune cell activating antibodies, or a combination thereof. In some cases, the antibody therapy comprises one or more antibodies that target tumor cell antigens.

In some instances, the immunotherapy utilizes immune checkpoint inhibitors. In some instances, the immune therapy comprises administration of a modulatory agent for an immune checkpoint. Examples of immune checkpoint targets include, but are not limited to, 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD160, CD2, CD200R, CD226, CD26, CD27, CD28, CD30, CD39, CD40, CD48, CD70, CD73, CD80 (B7.1). CD86 (B7.2), CEACAM1, CGEN-15049, CTLA-4, DR3, GAL9, GITR, GITRL, HVEM, ICOS, ICOSL (B7H2), IDO1, IDO2, ILT-2 (LILRB1), ILT-4 (LILRB2), KIR, KLRG1, LAG3, LAIR1 (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA. An immune checkpoint modulatory agent in some cases is at least one of a small molecule, an antibody, a nucleic acid encoding an antibody, an antigen binding fragment, a RNA interfering agent, a peptide, a peptidomimetic, a synthetic ligand, and an aptamer. In some instances, an immune checkpoint inhibitor is administered. In some cases, the immune checkpoint inhibitor is an antibody or antigen binding fragment that binds the immune checkpoint target, such as an anti-PD-1 antibody or and anti-PD-L1 antibody. Examples of immune checkpoint inhibitors are Enoblituzumab (e.g., MGA271), Ipilimumab (e.g., BMS-734016, MDX-010), Tremelimumab (e.g., CP-675, CP-675,206), Lirilumab (e.g., BMS-986015, IPH2102), BMS986016, Pembrolizumab (e.g., MK-3475, SCH 900475), Nivolumab (e.g., BMS-936558, MDX-1106, ONO-4538), Pidilizumab (e.g., CT-011, MDV9300), Atezolizumab (e.g., MPDL3280A. RG7446, RO5541267), BMS-936559 (e.g., MDX-1105), Durvalumab, Avelumab, and Bavituximab. In some instances, the immune therapy is CAR T cell or T cell receptor therapy.

In some embodiments, the immunotherapy is an immunotherapy regimen. In some instances, the regimen comprises a single dose of the immunotherapy. In some instances, the regimen comprises multiple doses of the immune therapy. In some instances, the regimen comprises at least 1, 2, 3, 4, 5, 6, 7, 8, 9, 10, 15, 20, 25, 30, 40, 50, or more doses of the immunotherapy. The immunotherapy regimen can be administered for any length of time. In some instances, the immunotherapy regimen is administered over a course of 1, 2, 3, 5, 10, 15, 20, 30, or more days. In some instances, the immunotherapy regimen is administered over the course of 1, 2, 3, 4, 5, or more weeks. In some instances, the immunotherapy regimen is administered over the course of 1, 2, 3, 4, 5, or more months. In some instances, the immunotherapy regimen comprises a plurality of different immunotherapeutic agents.

In some instances, the immunotherapy regimen comprises an active immunotherapy, a passive immunotherapy, or a combination thereof. In some instances, the immunotherapy regimen is an active immunotherapy. In some instances, the immunotherapy regimen is a passive immunotherapy.

In some instances, the level T-cell exhaustion of the subject is measured according to the methods provided herein. In some instances, the sample is sent out for analysis of cell status. An elevated level of exhausted T-cells may indicate that the immunotherapy is not working as intended. In some instances, an elevated level of exhausted T-cells indicates the subject will not respond to the immunotherapy regimen. In some instances, the elevated level of exhausted T-cells indicates the subject is not responding to the immunotherapy regimen. In some instances, the elevated level of exhausted T-cells indicates the immunotherapy regimen is ineffective. In some instances, the elevated level of exhausted T-cells indicates the immunotherapy regimen has lost efficacy. In some instances, an additional therapy is administered if the sample has an elevated level of exhausted T-cells. In some instances, a recommendation to administer an additional therapy is given if the sample has an elevated level of exhausted T-cells. In some instances, the exhausted T-cells are terminally exhausted T-cells. In some instances, the exhausted T-cells are progenitor exhausted T-cells.

In some instances, the elevated level of exhausted T-cells in the sample is at least 30%, 40%, 50%, 60%, 70%, 80%, or 90% of the T-cells of the sample. In some instances, the elevated level of exhausted T-cells in the sample is at least 70% of the T-cells of the sample. In some instances, the elevated level of exhausted T-cells in the sample is at least 80% of the T-cells of the sample. In some instances, the elevated level of exhausted T-cells in the sample is at least 90% of the T-cells of the sample. In some instances, the elevated level of exhausted T-cells in the sample is at least 30%, 40%, 50%, 60%, 70%, 80%, or 90% of one subtype of T-cell of the sample. In some instances, the exhausted T-cells are terminally exhausted T-cells. In some instances, the exhausted T-cells are progenitor exhausted T-cells.

Applying the deconvolution algorithm may further identify or quantify an amount or percentage of activated T-cells in the sample. A low level of activated T-cells may indicate that the immunotherapy is not working as intended. In some instances, a low level of activated T-cells indicates the subject will not respond to the immunotherapy regimen. In some instances, a low level of activated T-cells indicates the subject is not responding to the immunotherapy regimen. In some instances, a low level of activated T-cells indicates the immunotherapy regimen is ineffective. In some instances, a low level of activated T-cells indicates the immunotherapy regimen has lost efficacy. In some instances, an additional therapy is administered if the sample has a low level of activated T-cells. In some instances, a recommendation to administer an additional therapy is given if the sample has a low level of activated T-cells.

In some instances, a low level of activated T-cells in the sample is at most 10%, 20%, 30%, 40%, 50%, 60%, 70%, 80%, or 90% of the T-cells of the sample. In some instances, a low level of activated T-cells in the sample is at most 30% of the T-cells of the sample. In some instances, a low level of activated T-cells in the sample is at least 20% of the T-cells of the sample. In some instances, the elevated level of exhausted T-cells in the sample is at least 10% of the T-cells of the sample. In some instances, a low level of activated T-cells in the sample is at most 10%, 20%, 30%, 40%, 50%, 60%, 70%, 80%, or 90% of one subtype of T-cell of the sample.

In some instances, the deconvolution algorithm identifies a plurality of different T-cell statuses in a sample. In some instances, the deconvolution algorithm identifies at least 1, at least 2, at least 3, at least 4, or at least 5 T-cell statuses. In some instances, the plurality of different T-cell statuses are naïve status, activated status, central memory status, effector memory status, and/or exhausted status. In some instances, the amount or ratio of cells having one or more of the plurality of cell statuses is indicative or predictive of whether or not a given treatment will be effective.

The alternative therapy may be any type of therapy which will alleviate the underlying disease or condition of the patient. In some instances, the alternative therapy comprises chemotherapy, radiation therapy, surgery, or any combination thereof. In some instances, the alternative therapy comprises chemotherapy. In some instances, the alternative therapy comprises radiation therapy. In some instances, the alternative therapy comprises surgery.

In some instances, the alternative therapy is an additional immunotherapy. In some instances, the additional immunotherapy is a different immunotherapy from the first immunotherapy. In some instances, the additional immunotherapy is a different type of immunotherapy from the first immunotherapy. In some instances, the additional immunotherapy comprises an immune cell therapy, a cancer vaccine, a cytokine therapy, an antibody therapy, or any combination thereof. In some instances, the alternative therapy is a non-immunotherapy.

Further provided herein is a method of treating a subject. In some instances, the method comprises administering an immunotherapy regimen to a subject in need thereof. In some instances, the method comprises obtaining a sample from the subject. In some instances, the method comprises sending the sample for analysis of cell status. In some embodiments, the analysis of cell status comprises generating RNA sequencing data from the sample and applying a deconvolution algorithm to at least a subset of the RNA sequencing data to identify and quantify an amount or percentage of cells in the sample having one or more cell statuses based on expression levels of one or more cell status signature genes. In some instances, the method comprises determining if the immunotherapy regimen is effective based on the identity and quantity of the one or more cell statuses.

In some instances, analysis of cell status measures the status of at least one immune cell type. In some instances, the at least one immune cell type is selected from T-cells, natural killer (NK) cells, B-cells, macrophages, and plasma cells. In some instances, the at least one immune cell type is selected from the group consisting of CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. In some instances, the at least one immune cell type is selected from the group consisting of M macrophages, M2 macrophages, CD9+ B cells, CD14+ monocytes, CD56+ NK cells, CD8+ T cells, Treg cells, and CD4+ T cells. In some instances, the at least one immune cell type comprises T-cells. In some instances, the T-cells comprise CD8+ cells, CD4+ cells, or a combination thereof In some instances, the one or more cell statuses comprises naïve status, activated status, activation recovered status, terminally exhausted status, progenitor exhausted status, central memory status, effector memory status, stem cell memory status, or any combination thereof. In some instances, the one or more cell statuses comprise naïve status, activated status, exhausted status, central memory status, and effector memory status. In some instances, the one or more cell statuses comprise naïve status, activated status, and exhausted status. In some instances, the one or more cell statuses comprise activated status and exhausted status. In some instances, the one or more cell statuses comprises activated status. In some instances, the one or more cell statuses comprises exhausted status.

In some instances, determining if the immunotherapy regimen is effective based on the identity and quantity of the one or more cell statuses comprises comparing the quantity of cells having a particular cell status to a predetermined threshold for the particular cell status. In some instances, the predetermined threshold is at 10%, 20%, 30%, 40%, 50%, 60%, 70%, 80%, or 90%.

In some instances, determination of cellular status occurs prior to a treatment, during a treatment, or after a treatment. In some instances, determination cellular status occurs one or more time points prior to a treatment, during a treatment, or after a treatment. Time points for the monitoring and response-to-treatment methods provided herein, include any interval of time. In some instances, the time points are 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years or longer apart. In some instances, samples are obtained at any number of time points, including 2, 3, 4, 5, 6, 7, 8, 9, 10, 11, 12, or more time points In some cases, the methods and systems disclosed herein for predicting a response of a subject having a disease or medical condition to a therapy. In some cases, the therapy is an immunotherapy regimen. The immunotherapy regimen can be any of the immunotherapy regimens provided herein, including without limitation checkpoint inhibitor therapies (e.g. anti-PD-1 or anti-PD-L1 antibodies), cell therapies (e.g. CAR-T or CAR-NK therapies), or other immunotherapies (e.g. cancer vaccine immunotherapies or tumor infiltrating lymphocyte therapies). In some cases, the disease or medical condition is cancer (e.g. head and neck squamous cell carcinoma, non-small cell lung cancer, or melanoma). The cancer can be recurrent or metastatic.

In some cases, the methods and systems described herein are used for diagnosing or treating a disease or disorder, wherein the disease or disorder is cancer. In some instances, the cancer is a solid cancer or a hematopoietic cancer. Sometimes, a cancer targeted herein is a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, breast cancer such as a ductal carcinoma, medullary carcinomas, colloid carcinomas, tubular carcinomas, and inflammatory breast cancer; ovarian cancer, including epithelial ovarian tumors and adenocarcinoma in the ovary; uterine cancer; cervical cancer such as adenocarcinoma in the cervix epithelial, squamous cell carcinoma and adenocarcinomas; prostate cancer, including adenocarcinoma; pancreatic cancer, including epitheloid carcinoma in the pancreatic duct tissue and adenocarcinoma in the pancreatic duct; bladder cancer, including transitional cell carcinoma, urothelial carcinomas, tumors in the urothelial cells, squamous cell carcinomas, adenocarcinomas, and small cell cancers: leukemia, including acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer: lung cancer, including non-small cell lung cancer (NSCLC) such as squamous cell carcinomas, adenocarcinomas, and large cell undifferentiated carcinomas, and small cell lung cancer; skin cancer, including basal cell carcinoma, melanoma, and squamous cell carcinoma; eye retinoblastoma; cutaneous or intraocular melanoma, primary liver cancer: kidney cancer: autoimmune deficiency syndrome related lymphoma, including diffuse large B-cell lymphoma, B-cell immunoblastic lymphoma and small non-cleaved cell lymphoma: Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma, and human papilloma virus (HPV) and cervical cancer; central nervous system (CNS) cancers, including primary brain tumors such as astrocytoma, anaplastic astrocytoma, or glioblastoma multiforme, oligodendrogliomas, ependymomas, meningiomas, lymphomas, schwannomas, and medulloblastomas; peripheral nervous system (PNS) cancers, including acoustic neuromas and malignant peripheral nerve sheath tumors (MPNST) such as neurofibromas and schwannomas, malignant fibrous cytomas, malignant fibrous histiocytomas, malignant meningiomas, malignant mesotheliomas, and malignant mixed Müllerian tumors; oral cavity and oropharyngeal cancer such as hypopharyngeal cancer, laryngeal cancer, nasopharyngeal cancer, and oropharyngeal cancer; stomach cancer, including lymphomas, gastric stromal tumors, and carcinoid tumors: testicular cancer such as germ cell tumors (GCTs), which include seminomas and nonseminomas, and gonadal stromal tumors, which include Leydig cell tumors and Sertoli cell tumors; thymus cancer, including thymomas, thymic carcinomas, Hodgkin disease, non-Hodgkin lymphomas carcinoids or carcinoid tumors; rectal cancer; and colon cancer.

Generation of Immune Cell Therapies

Provided herein is a method of preparing an immune cell therapy. In some instances, the method comprises obtaining immune cells derived from a subject. In some instances, the subject is in need immune cell therapy. In some instances, the method comprises assessing the status of the immune cells. In some instances, the immune cells are assessed by generating RNA sequencing data from a subset of the immune cells; and applying a deconvolution algorithm to at least a subset of the RNA sequencing data to identify and quantify an amount or percentage of immune cells in the sample having at least one particular status based on expression levels of one or more cell status signature gene. In some instances, the method further comprises activating the immune cells. In some instances, the immune cells are activated to target cancerous tissue in the subject.

By determining the status of the immune cells in this process, a determination of which states correlate with the best outcomes of immune cell therapies can be ascertained. Additionally, the optimal time to dose the immune cell therapy can also be ascertained by measuring one or more status of the immune cells prior to dosing. For example, the immune cell therapy can be dosed at the peak point of cell activation, before exhaustion begins to set in, or at any other time point. Further, determination of immune cell status at the point of harvesting immune cells from the subject in order to create the immune cell therapy can be used to predict if a patient will be responsive to immune cell therapy or another immunotherapy.

Assessing the status of the immune cells can be performed any number of times. In some instances, assessing the status of the immune cells is performed multiple times. In some instances, assessing the status of the immune cells is performed at a plurality of time points in the process. In some instances, assessing the status of the immune cells is performed at least prior to activating the immune cells. In some instances, assessing the status of the immune cells is performed at least once after activating the immune cells. In some instances, assessing the status of the immune cells is performed multiple times after activating the immune cells. In some instances, assessing the status of the immune cells is performed at least 1, 2, 3, 4, 5, 6, 7, 8, 9, 10 or more times. In some instances, assessing the status of the immune cells is performed daily throughout the process.

In some instances, the at least one particular status comprises naïve status, activated status, activation recovered status, terminally exhausted status, progenitor exhausted status, central memory status, effector memory status, stem cell memory, or any combination thereof. In some instances, the at least one particular status comprises naïve status, activated status, exhausted status, central memory status, and effector memory status. In some instances, the at least one particular status comprises naïve status, activated status, and exhausted status. In some instances, the at least one particular status comprises activated status and exhausted status. In some instances, the at least one particular status comprises activated status. In some instances, the at least one particular status comprises exhausted status.

In some instances, the method further comprises predicting the efficacy of the immune cell therapy based on the identity and quantity of immune cells having at least one particular status. In some instances, the efficacy is predicted based on the quantity of exhausted cells. In some instances, the immune cell therapy is predicted to be efficacious if the number of exhausted cells is below a threshold percentage of the total cells such as, for example, 30%, 20%, 10%, or 5% of the total number of cells. In some instances, the efficacy is predicted based on the quantity of activated cells. In some instances, the immune cell therapy is predicted to be efficacious if the number of activated cells is at least a threshold percentage of total cells such as, for example, 70%, 80%, 90%, or 95% of the total number of cells. In some instances, the efficacy is predicted based on the quantity of naïve cells. In some instances, the immune cell therapy is predicted to be efficacious if the number of naïve cells is at least a threshold percentage of total cells such as, for example, 70%, 80%, 90%, or 95% of the total number of cells. In some instances, the efficacy is predicted based on the quantity of naïve cells when the immune cells are obtained from the patient.

In some instances, the efficacy of the immune cell therapy comprises comparing the identity and quantity of immune cells having at least one particular status to a reference. In some embodiments, the reference is a prior immune cell therapy delivered to a patient that was efficacious. In some instances, the at least one particular status compared to the reference comprises an exhaustion status. In some instances, the at least one particular status compared to the reference comprises an activated status. In some instances, the at least one particular status compared to the reference comprises a naïve status.

In some instances, the efficacy is predicted based on the identity and quantity of immune cells having a particular status prior to activating the cells. In some instances, the efficacy is predicted based on the identity and quantity of immune cells having a particular status after activating the cells.

The immune cell therapy can be of any type. In some instances, the immune cell therapy is chimeric antigen receptor T-cell (CAR-T) therapy, tumor-infiltrating lymphocyte (TIL) therapy, engineered T-cell receptor (TCR) therapy, or natural killer (NK) cell therapy. In some instances, the immune cell therapy is TIL therapy. In some instances, the immune cell therapy is TCR therapy. In some instances, the immune cell therapy is NK therapy. In some instances, the immune cell therapy is CAR-T therapy. In some instances, the CAR-T therapy is axicabtagene ciloleucel or tisagenlecleucel.

In some instances, the immune cell therapy comprises a CD19-targeting, CD22-targeting, or CD123-targeting cell therapy. In some instances, the immune cell therapy comprises a CD19-targeting cell therapy. In some instances, the immune cell therapy comprises a CD22-targeting cell therapy. In some instances, the immune cell therapy comprises a CD123-targeting cell therapy.

In some instances, activating the immune cells comprises inserting a chimeric antigen receptor gene into the immune cells. In some instances, activating the immune cells comprises inserting an engineered T-cell receptor gene into the immune cells. In some instances, activating the immune cells comprises incubating the immune cells with a tumor cell antigen.

In some instances, the method further comprises proliferating the immune cells. In some instances, the immune cells are proliferated after activation. In some instances, the immune cells are proliferated prior to activation.

Immune Oncology Methods

Provided herein are methods and systems for determining an immune-oncology profile using sequencing data, wherein the profile may be used for therapeutic applications. In some instances, the profile comprises immune modulatory molecule expression, cell type and ratio, and mutational burden. In some instances, the profile comprises immune modulatory molecule expression, cell type and ratio, and mutational burden In some instances, the profile is determined for diagnosis of a disease or disorder. In some instances, the profile is determined for treatment purposes. For example, the profile is used to determine efficacy of a treatment regimen. In some instances, the profile is used to recommend a therapeutic intervention.

In some instances, determination of the immune-oncology profile occurs prior to a treatment, during a treatment, or after a treatment. In some instances, determination of the immune-oncology profile occurs one or more time points prior to a treatment, during a treatment, or after a treatment. Time points for the monitoring and response-to-treatment methods provided herein, include any interval of time. In some instances, the time points are 1 day, 2 days, 3 days, 4 days, 5 days 6 days, week, 2 weeks, 3, weeks, 4 weeks, 1 month, 2 months, 3 months, 4 months, 5 months, 6 months, 7 months, 8 months, 9 months, 10 months, 11 months, 1 year, 2 years or longer apart. In some instances, samples are obtained at any number of time points, including 2, 3, 4, 5, 6, 7, 8, 9, 10, I1, 12, or more time points.

In some instances, the immune-oncology profile is used to determine a specific treatment for a disease or disorder subject. In some instances, a sample is a first sample obtained from a subject at a first time point. In some instances, the method further comprises determining the immune-oncology profile by determining the immune modulatory molecule expression, cell type and ratio, and mutational burden from a second sample obtained from the subject having the related disease or disorder at a second time point; and comparing the immune-oncology profile from the first time point to the second time point. In some instances, the method further comprises determining the immune-oncology profile by determining the immune modulatory molecule expression, cell type and ratio, and cell status from a second sample obtained from the subject having the related disease or disorder at a second time point; and comparing the immune-oncology profile from the first time point to the second time point. Sometimes, immune-oncology profiles are generated for a subject at multiple time points, wherein the profiles are compared to evaluate the progression of a disease or disorder and/or a response to treatment.

In some cases, the methods and systems described herein are used for diagnosing or treating a disease or disorder, wherein the disease or disorder is cancer. In some instances, the cancer is a solid cancer or a hematopoietic cancer. Sometimes, a cancer targeted herein is a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, breast cancer such as a ductal carcinoma, medullary carcinomas, colloid carcinomas, tubular carcinomas, and inflammatory breast cancer; ovarian cancer, including epithelial ovarian tumors and adenocarcinoma in the ovary; uterine cancer; cervical cancer such as adenocarcinoma in the cervix epithelial, squamous cell carcinoma and adenocarcinomas; prostate cancer, including adenocarcinoma; pancreatic cancer, including epitheloid carcinoma in the pancreatic duct tissue and adenocarcinoma in the pancreatic duct: bladder cancer, including transitional cell carcinoma, urothelial carcinomas, tumors in the urothelial cells, squamous cell carcinomas, adenocarcinomas, and small cell cancers; leukemia, including acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer: lung cancer, including non-small cell lung cancer (NSCLC) such as squamous cell carcinomas, adenocarcinomas, and large cell undifferentiated carcinomas, and small cell lung cancer; skin cancer, including basal cell carcinoma, melanoma, and squamous cell carcinoma; eye retinoblastoma: cutaneous or intraocular melanoma; primary liver cancer; kidney cancer: autoimmune deficiency syndrome related lymphoma, including diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system (CNS) cancers, including primary brain tumors such as astrocytoma, anaplastic astrocytoma, or glioblastoma multiforme, oligodendrogliomas, ependymomas, meningiomas, lymphomas, schwannomas, and medulloblastomas; peripheral nervous system (PNS) cancers, including acoustic neuromas and malignant peripheral nerve sheath tumors (MPNST) such as neurofibromas and schwannomas, malignant fibrous cytomas, malignant fibrous histiocytomas, malignant meningiomas, malignant mesotheliomas, and malignant mixed Müllerian tumors; oral cavity and oropharyngeal cancer such as hypopharyngeal cancer, laryngeal cancer, nasopharyngeal cancer, and oropharyngeal cancer: stomach cancer, including lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer, including thymomas, thymic carcinomas, Hodgkin disease, non-Hodgkin lymphomas carcinoids or carcinoid tumors, rectal cancer; and colon cancer.

In some cases, the methods and systems disclosed herein for determining immune modulatory molecule expression, cell type and ratio, and mutational burden are used for treating cancer. In some cases, the methods and systems disclosed herein for determining immune modulatory molecule expression, cell type and ratio, and cell status are used for treating cancer. For example, at least one of immune modulatory molecule expression, cell type and ratio, and mutational burden is determined prior to cancer treatment. In some cases, at least one of immune modulatory molecule expression, cell type and ratio, cell status, and mutational burden is measured in a sample. In some instances, the sample is obtained from tumor tissues. In some cases, the sample is obtained from non-tumor tissues. In some cases, the sample is obtained from a subject who has cancer or has been diagnosed with cancer. In some cases, the sample is obtained from subjects who have not been diagnosed with cancer. In some cases, the sample is obtained from subjects who are in remission. Following determination of an immune-oncology profile based on at least one of immune modulatory molecule expression, cell type and ratio, cell status, and mutational burden, a cancer treatment may be applied. Examples of treatments for cancer include, but are not limited to, chemotherapy, radiation, surgery, or immunotherapy.

In some instances, determination of the immune-oncology profile occurs in conjunction with surgery. For example, determination of the immune-oncology profile occurs prior to tumor surgery and/or following tumor surgery. In some instances, the immune-oncology profile is indicative of the efficacy of the surgery. The immune-oncology profile may be determined any time following surgery. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following surgery. In some instances, the immune-oncology profile is determined at any number of time points, including 2, 3, 4, 5, 6, 7, 8, 9, 10, 11, 12, or more time points.

In some instances, determination of the immune-oncology profile (e.g., T-cell state or status alone or in combination with other information such as immune inhibitory or checkpoint molecules or other immune cell quantities or percentages) occurs in conjunction with chemotherapy. In some cases, the methods disclosed herein comprise selecting a patient to receive treatment or who is undergoing treatment (e.g., an immunotherapy), obtaining an evaluation of the patient based on a tissue sample (e.g., tumor biopsy) that includes an immune-oncology profile (e.g., a report including T-cell state or status and/or other immune information), and providing treatment, continuing treatment, or discontinuing treatment based at least on the immune-oncology profile. For example, determination of the immune-oncology profile occurs prior to chemotherapy and following chemotherapy. In some instances, determination of the immune-oncology profile indicates the efficacy of the chemotherapy. Examples of chemotherapy includes, but are not limited to, cyclophosphamide, paclitaxel, 5-fluorouracil, 5-aza-2'-deoxycitidine, mitomycin, doxorubicin, and mitoxantrone. The immune-oncology profile may be determined any time following chemotherapy. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following chemotherapy. In some instances, the immune-oncology profile is determined at any number of time points, including 2, 3, 4, 5, 6, 7, 8, 9, 10, 11, 12, or more time points.

In some instances, determination of the immune-oncology profile occurs in conjunction with radiation treatment. For example, determination of the immune-oncology profile occurs prior to radiation treatment and/or following radiation treatment. In some instances, the immune-oncology profile indicates the efficacy of the radiation treatment. The immune-oncology profile may be determined any time following radiation treatment. In some instances, the immune-oncology profile is determined 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years, or more than 2 years following radiation treatment. In some instances, the immune-oncology profile is determined at any number of time points, including 2, 3, 4, 5, 6, 7, 8, 9, 10, 11, 12, or more time points.

Alternately or in combination with surgery, chemotherapy, or radiation, determination of the immune-oncology profile occurs in conjunction with immune therapy. In some instances, the immune therapy comprises administration of a modulatory agent for an immune checkpoint. Examples of immune checkpoint targets include, but are not limited to, 2B4 (CD244), A2aR, B7H3 (CD276), B7H4 (VTCN1), B7H6, B7RP1, BTLA (CD272), butyrophilins, CD103, CD122, CD137 (4-1BB), CD137L, CD16A, CD2, CD200R, CD226, CD26, CD27, CD28, CD30, CD39, CD40, CD48, CD70, CD73, CD80 (B7.1), CD86 (B7.2), CEACAM1, CGEN-15049. CTLA-4, DR3, GAL9, GITR. GITRL, HVEM, ICOS, ICOSL (B7H2), IDO1, IDO2, ILT-2 (LILRB1), ILT-4 (LILRB2), KIR, KLRG1, LAG3, LAIR (CD305), LIGHT (TNFSF14), MARCO, NKG2A, NKG2D, OX-40, OX-40L, PD-1, PDL-1 (B7-H1, CD 274), PDL-2 (B7-DC, CD 273), PS, SIRPalpha (CD47), SLAM, TGFR, TIGIT, TIM1, TIM3 (HAVCR2), TIM4, or VISTA. An immune checkpoint modulatory agent in some cases is at least one of a small molecule, an antibody, a nucleic acid encoding an antibody, an antigen binding fragment, a RNA interfering agent, a peptide, a peptidomimetic, a synthetic ligand, and an aptamer. In some instances, an immune checkpoint inhibitor is administered. Examples of immune checkpoint inhibitors are Enoblituzumab (e.g., MGA271), Ipilimumab (e.g., BMS-734016, MDX-010), Tremelimumab (e.g., CP-675, CP-675,206), Lirilumab (e.g., BMS-986015, IPH2102), BMS986016, Pembrolizumab (e.g., MK-3475, SCH 900475). Nivolumab (e.g., BMS-936558, MDX-1106, ONO-4538), Pidilizumab (e.g., CT-011, MDV9300), Atezolizumab (e.g., MPDL3280A, RG7446, RO5541267), BMS-936559 (e.g., MDX-1105), Durvalumab, Avelumab, and Bavituximab. In some instances, the immune therapy is CAR T cell or T cell receptor therapy.

Methods and systems provided herein for determination of an immune-oncology profile may be used for prediction of a clinical outcome in response to a therapy. In some instances, the therapy is surgery, radiation, chemotherapy, or immune therapy. In some instances, the immune-oncology profile is used to predict a level of resistance to one or more chemotherapeutic agents. In some instances, the prediction of a clinical outcome based on the immune-oncology profile has an accuracy, specificity, sensitivity, positive predictive value (PPV), a negative predictive value (NPV), or a combination thereof for a type of response. In some instances, the type of response is a positive response. In some instances, a positive response is partial remission (e.g., cancer/tumor has gotten smaller) or complete remission (e.g., all signs of cancer are gone) of the tumor. In some instances, a positive response is the cancer has stopped growing or expanding. In some instances, a positive response is a statistically higher survival rate for a treated subject population compared to an untreated subject population. In some instances, the survival rate is a 1 year, 2 year, 3 year, 4 year, 5 year, 6 year, 7 year, 8 year, 9 year, or 10 year survival rate. In some instances, the type of response is a negative response. In some instances, a negative response is the absence of a positive response. In some instances, a negative response is continued cancer progression or growth. In some instances, a negative response is the continued presence of the cancer. In some instances, a positive response is continued cancer progression or growth at the predicted rate for an untreated subject population. In some instances, a prediction of a clinical outcome (e.g., a positive or negative response) has a positive predictive value for a set of independent samples. In some instances, the PPV for a response to a therapy is at least or about 90% for at least 100 independent samples. A positive predictive value may be accurately determined in at least about 50%, 60%, 70%, 80%, 90%, 95%, or 99% of at least 100, 200, 300, 400, 500, 600, 700, 800, 900, 1000, 2000, 3000, 4000, 5000, 6000, 7000, 8000, 9000, or 10000 independent samples.

In some instances, a prediction is generated using a classifier. In some instances, the proportions of cell types/subtypes determined by deconvolution, mutational burden, immune modulatory molecule expression, or any combination thereof are associated with an outcome such as, for example, a clinical outcome, a diagnosis of disease, and/or a response to therapy. In some instances, the classifier is trained using data comprising one or more of cell type/subtype proportions, cell status, mutational burden, and immune modulatory molecule expression along with associated outcomes. In some instances, the classifier comprises a panel of cell type/subtype proportions that are predictive of an outcome. In some instances, the classifier comprises a panel of immune modulatory molecules predictive of an outcome. In some instances, the classifier comprises a panel of mutational burden predictive of an outcome. In some instances, the classifier comprises a panel of cell statuses predictive of an outcome.

Disclosed herein, in some instances, are systems and methods for generating and/or using a classifier to make a prediction of an outcome. The classifier can be a machine learning algorithm or model trained using data from the immune-oncology profile. The data utilized from the immune-oncology profile can include the cell type/subtype proportions or percentages (e.g., immune cell types and percentages in a tumor sample). Examples of the cell types or subtypes include M1 macrophages, M2 macrophages, CD19+ B cells, CD14+ monocytes, CD56+ NK cells, CD8+ T cells, Treg cells, CD4+ T cells, or any combination thereof. Additional examples of cell types or subtypes are found throughout the present disclosure. In some cases, the data includes expression of immune-inhibitory genes or immune escape genes which can include, for example, CTLA4, OX40, PD-1, IDO1, CD47, PD-L1, TIM-3, BTLA, ICOS, ARG1, or any combination thereof. The data can also, in certain cases, include mutational burden information relating to the sample.

The classifier or trained algorithm of the present disclosure may be used make a prediction. The prediction can be based on information from an immune-oncology profile of a sample such as at least one of percentage(s) of cell type(s)/subtype(s), level(s) of immune inhibitory or escape gene(s), or mutational burden. The prediction can comprise identifying and quantifying a sample into two or more categories such as different cell statuses for a given cell type. The prediction can relate to diagnosis and/or prognosis. The prediction can also be based on monitoring the success of treatment of disease. Predictions can also be based on quality of life or symptomatic response. As an example, the prediction for a tumor sample obtained from a subject includes a positive identification of the sample as pancreatic ductal adenocarcinoma (PDA). The prediction optionally also includes a corresponding prediction classifying the sample as having poor survival based on immune-oncology profile data including high PD-L1 expression level and high Treg cell percentage infiltrating the tumor sample. The categories or groups can correspond to various predicted outcomes such as predicted treatment outcome or responsiveness to treatment.

The classifier used to generate predictions includes one or more selected feature spaces such as cell type/subtype proportion/percentage, immune inhibitory gene expression level, and mutational burden. The values for these features obtained from a sample can be fed into the classifier or trained algorithm to generate one or more predictions. In some cases, the methods disclosed herein select for the variables that are of predictive value, for example, by culling the features to generate a feature subset used for generating predictions in the final classifier or model. Methods that reduce the number of variables or features can be selected from a non-limiting group of algorithms including principal component analysis (PCA), partial least squares (PLS) regression, and independent component analysis (ICA). In some cases, the methods disclosed herein analyze numerous variables directly and are selected from a non-limiting group of algorithms including methods based on machine learning processes. Machine learning processes can include random forest algorithms, bagging techniques, boosting methods, or any combination thereof. Methods may be statistical methods. Statistical methods can include penalized logistic regression, prediction analysis of microarrays, methods based on shrunken centroids, support vector machine analysis, or regularized linear discriminant analysis.

The classifier or trained algorithm of the present disclosure as described herein can comprise one feature space. The classifier or trained algorithm of the present disclosure as described herein can comprise two or more feature spaces. The two or more feature spaces may be distinct from one another. Each feature space can comprise types of information about a sample, such as cell type/subtype percentage, expression of immune inhibitory molecules or genes, or mutational burden. The accuracy of the classification may be improved by combining two or more feature spaces in a classifier rather than using a single feature space. In some cases, combining both cell type/subtype percentage and immune inhibitory gene expression results in superior accuracy than using those features individually. Sometimes, accuracy is further improved by incorporating mutational burden. Individual feature spaces may have different dynamic ranges. The difference in the dynamic ranges between feature spaces may be at least 1, 2, 3, 4, or 5 orders of magnitude. As a non-limiting example, the cell subtype percentage feature space may have a dynamic range between 0 and 100, and the immune inhibitory gene expression feature space may have a dynamic range between 0 and about 20.

A feature space can comprise a panel of cell types/subtypes and their percentage or proportion within a sample. A feature space can comprise a panel of immune inhibitory genes and their expression level. A feature space can comprise one or more representations of mutational burden. A panel of an individual feature space may be associated with an outcome such as, for example, responsiveness to treatment. For example, a positive response to an immunotherapy may be associated with certain immune cell types exceeding a threshold percentage within a tumor sample. As another example, a negative response to an immunotherapy may be associated with an immune-inhibitory gene such as PD-L1 exceeding a threshold expression level within a tumor sample. In some cases, the classifier or trained algorithm comprises a panel of cell type/subtype percentages comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 20 cell types/subtypes. The classifier can comprise a panel of immune-inhibitory genes comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or at least 24 genes.

The classifier of the present disclosure may be trained with a set of samples obtained from subjects. A set of samples can comprise samples from at least 5, 10, 15, 20, 25, 30, 35, 40, 45, 50, 60, 70, 80, 90, 100, 150, 200, 250, 300, 350, 400, 450, 500, 600, 700, 800, 9, 1000, 2000, 3000, 4000, 5000, or more subjects. In some cases, the classifier is trained on a limited sample set with no more than 5, 10, 15, 20, 25, 30, 35, 40, 45, 50, 55, 60, 65, 70, 75, 80, 85, 90, 95, or 100 samples. The classifier may be trained on a limited sample set with no more than 15-20 samples or no more than 20-30 samples. The accuracy of the classifier takes on even greater importance when the sample size is small. A significant factor in the accuracy of the classifier is the quality of the data parameters input into the classifier to generate the prediction or classification. Likewise, the quality of the data input used to train the classifier is important to its predictive ability. For example, a classifier trained on a training data set having cell subtype percentages that were inaccurately determined will incorporate this inaccuracy during the training, which compromises its predictive ability with regards to new samples. When the sample size is large, a few poor data points will not have a significant impact on the resulting classifier. However, in the case when sample size is small such as around 15-25 samples, a few poor data points can negatively impact the classifier's predictive ability to a significant degree. Accordingly, the methods disclosed herein utilizing RNA normalization techniques that account for quantitative differences in RNA content amongst different cell types help generate highly accurate cell type/subtype percentages, which in turn allow for the generation of classifiers that effectively generate predictions despite being trained on small data sets such as, for example, no more than 15, 20, 25, 30, 35, 40, 45, 50, or 60 samples. This capability is critical for small-scale studies such as, for example, Phase 1/clinical trials which often entail small sample sizes. Indeed, larger Phase 11 trials may have 60 subjects, but the experimental group may still be only 15-20 when accounting for controls (e.g., 20 negative placebo controls, 20 receiving traditional treatment, and 20 receiving experimental treatment).

Moreover, in certain instances, the methods disclosed herein utilize end-to-end sample processing and analysis for quality control. As an example, FFPE curls obtained from tumor tissues are obtained, processed, and sequenced via next generation sequencing in a continuous workflow. In this example, the features utilized by the classifier are all mined from the sequencing data. For instance, RNA expression data (RNASeq) is fed into a deconvolution algorithm to determine cell type/subtype percentages. Likewise, the expression levels of immune inhibitory genes are also obtained from the sequencing data. Mutational burden can also be determined from the sequencing data.

A classifier may generate a different prediction each time it is given new sample data. Using different samples on the same classifier can generate a different or unique output each time the classifier is run. Using the same samples on the same classifier can generate a different or unique output each time the classifier is run. The classifier may analyze a sample by comparing it against the panel of features predictive of an outcome or response. In some cases, the classifier carries out the comparing, statistical analysis, downstream analyses, or any combination thereof.

In some cases, the features (e.g., cell type percentages, and optionally immune escape gene expression, cell statuses and/or mutational burden) are analyzed using feature selection techniques. Feature selection techniques can include filters for evaluating feature relevance by examining the data properties, wrappers that embed the model hypothesis within a feature subset search, or embedded protocols that build the search for an optimal feature set is built into a classifier algorithm. In some cases, the methods described herein comprise a feature selection step in which relevant features are selected for inclusion in the final classifier and/or irrelevant or low relevance features are culled or removed from the final classifier.

Examples of filters that can be beneficial for use in the methods of the present disclosure include parametric methods such as two sample t-tests, analysis of variance (ANOVA) analyses, Gamma distribution models, or Bayesian models. Filters can include model free methods such as Wilcoxon rank sum tests, rank products methods, random permutation methods, between-within class sum of squares tests, or threshold number of misclassification. In some cases, filters include multivariate methods such as bivariate analysis, correlation based feature selection methods, minimum redundancy maximum relevance, Markov blanket filter, and uncorrelated shrunken centroid methods.

Wrappers that may be beneficial for use in the methods of the present disclosure can include sequential search methods, estimation of distribution algorithms, or genetic algorithms. Embedded protocols that may be beneficial for use in the methods of the present disclosure can include random forest algorithms, weights of logistic regression algorithms, or weight vector of support vector machine algorithms.

The statistical results obtained from the methods described herein can provide the likelihood the prediction is accurate. In some cases, the prediction is presented as a diagnosis along with a likelihood of accuracy such as, for example, a prediction of a positive response to a therapeutic cancer treatment with at least a 70%, 75%, 80%, 85%, 90%, or 95% estimated accuracy. The predictions may be analyzed using statistical tools including students T test, two sided T test, Pearson rank sum analysis, hidden Markov model analysis, analysis of q-q plots, principal component analysis, one way analysis of variance (ANOVA), two way ANOVA, and other statistical methods.

Computer Systems

Figure 4:
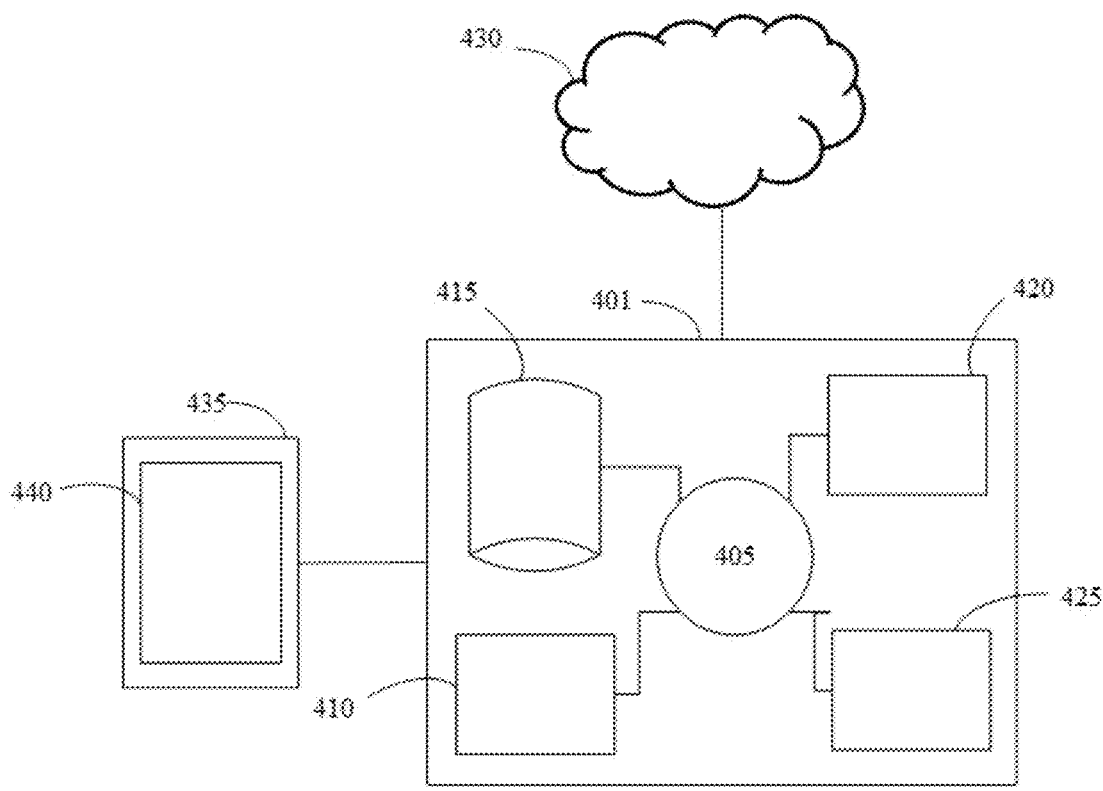
FIG. 4 schematically illustrates a computer system that is programmed or otherwise configured to implement methods provided herein.

The present disclosure provides computer systems that are programmed to implement methods of the disclosure. FIG. 4 shows a computer system 401 that is programmed or otherwise configured to carry out executable instructions. The computer system may be programmed to process nucleic acid sequencing information (e.g., next generation RNA sequencing data) to generate a classifier comprising a panel of cell statuses or categories for predicting response to treatment or outcome. The computer system may be programmed with a classifier for analyzing gene expression data to generate a prediction of an outcome for a particular therapy such as immunotherapy. The computer system 401 can regulate various aspects of the methods of the present disclosure, such as, for example, training the algorithm with the nucleic acid sequencing information of a set of samples to generate a trained algorithm or classifier. The computer system 401 may determine the positive predictive value of a classifier by analyzing a set of independent samples with the classifier and comparing the actual treatment outcome to the predicted outcome. The computer system 401 can be an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data. e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., a laptop or a smart phone). Examples of remote computer systems include personal computers (e.g., portable PC), slate or tablet PC's (e.g., Apple® iPad, Samsung® Galaxy Tab), telephones. Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases or other components shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, reports or results of immune cell status determination based on nucleic acid sequencing information of a sample. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, analyze the nucleic acid sequencing information obtained from a sample to identify and/or quantify one or more cell statuses (e.g., T-cell exhaustion status).

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

Terminology

The terminology used herein is for the purpose of describing particular embodiments only and is not intended to be limiting of any embodiment. As used herein, the singular forms "a." "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

The term "ribonucleic acid" or "RNA," as used herein refers to a molecule comprising at least one ribonucleotide residue. RNA may include transcripts. By "ribonucleotide" is meant a nucleotide with a hydroxyl group at the 2' position of a beta-D-ribo-furanose moiety. The term RNA includes, but not limited to, mRNA, ribosomal RNA, tRNA, non-protein-coding RNA (npcRNA), non-messenger RNA, functional RNA (fRNA), long non-coding RNA (lncRNA), pre-mRNAs, and primary miRNAs (pri-miRNAs). The term RNA includes, for example, double-stranded (ds) RNAs; single-stranded RNAs; and isolated RNAs such as partially purified RNA, essentially pure RNA, synthetic RNA, recombinant RNA, as well as altered RNA that differ from naturally-occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules described herein can also comprise non-standard nucleotides, such as non-naturally occurring nucleotides or chemically synthesized nucleotides or deoxynucleotides. These altered RNAs can be referred to as analogs or analogs of naturally-occurring RNA.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The term "sample," as used herein, generally refers to a biological sample of a subject. The biological sample may be a tissue or fluid of the subject, such as blood (e.g., whole blood), plasma, serum, urine, saliva, mucosal excretions, sputum, stool and tears. The biological sample may be derived from a tissue or fluid of the subject. The biological sample may be a tumor sample or heterogeneous tissue sample. The biological sample may have or be suspected of having disease tissue. The tissue may be processed to obtain the biological sample. The biological sample may be a cellular sample. The biological sample may be a cell-free (or cell free) sample, such as cell-free DNA or RNA. The biological sample may comprise cancer cells, non-cancer cells, immune cells, non-immune cells, or any combination thereof. The biological sample may be a tissue sample. The biological sample may be a liquid sample. The liquid sample can be a cancer or non-cancer sample. Non-limiting examples of liquid biological samples include synovial fluid, whole blood, blood plasma, lymph, bone marrow, cerebrospinal fluid, serum, seminal fluid, urine, and amniotic fluid.

The term "variant," as used herein, generally refers to a genetic variant, such as an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "subject," as used herein, generally refers to an animal, such as a mammalian species (e.g., human) or avian (e.g., bird) species, or other organism, such as a plant. More specifically, the subject can be a vertebrate, a mammal, a mouse, a primate, a simian or a human. Animals include, but are not limited to, farm animals, sport animals, and pets. The subject can be a healthy individual, an individual that has or is suspected of having a disease or a pre-disposition to the disease, or an individual that is in need of therapy or suspected of needing therapy. The subject can be a patient. The subject may have or be suspected of having a disease.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following examples are given for the purpose of illustrating various embodiments of the disclosure and are not meant to limit the present disclosure in any fashion. The present examples, along with the methods described herein are presently representative of certain embodiments, and are not intended as limitations on the scope of the disclosure. Changes therein and other uses which are encompassed within the spirit of the disclosure as defined by the scope of the claims will occur to those skilled in the art.

Example 1: Assessment of T-Cell Status in CD8+ T-Cells During Repeated Activation Human naïve CD8+ T-cells were repeatedly activated with anti-CD3, anti-CD28, and anti-CD2 tetramers over a period of two weeks. At time points every two days (unstimulated Day 0, 2, 4, 6, 8, 10, 12, and 14), cells were harvested. At each time point, RNA was extracted from a subset of the harvested cells using the RNeasy kit (Qiagen) according to manufacturer's instructions. Following RNA extraction of the subset, a sequencing library for next generation sequencing was generated according to manufacturer's instructions (Illumina). Coding regions were captures using Illumina Access kits. The enriched genes were sequenced on an Illumina NextSeq sequencing machine to generate sequencing data and expression data used to analyze the cellular status of the sample.

Additionally, cells at each time point were stained for cell surface marker expression of inhibitory receptors Programmed cell death protein 1 (PD1), lymphocyte-activation gene 3 (LAG3), and T-cell immunoglobulin and mucin domain containing-3 (TIM3). These cells were analyzed by flow cytometry to determine the percentage of cells in the sample triple-positive for the three markers. Finally, the concentration of cytokines interferon gamma (IFNγ) and interleukin-2 (IL-2) were measured in the cell supernatant at each time point.

Figure 5:
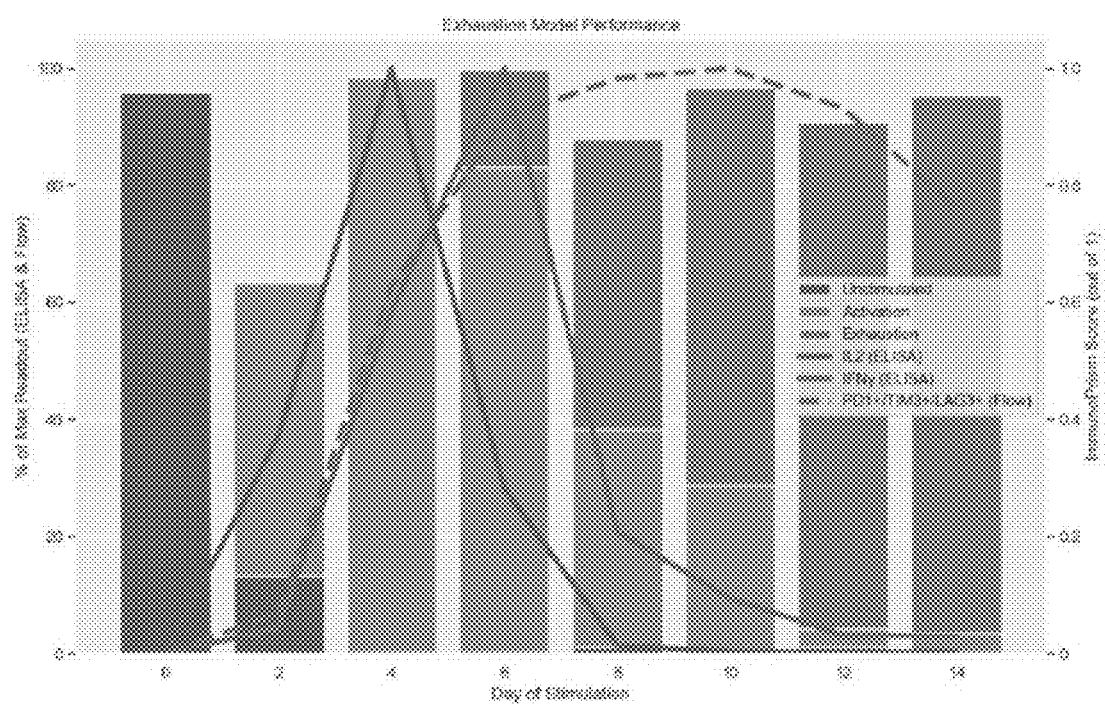
FIG. 5 shows a graph of percentage CD8+ cells having a particular status measured by the methods provided herein in a culture along with measurements of key biomarkers.

A hallmark of T-cell exhaustion is the progressive increase in the expression of inhibitory receptors such as PD1, TIM3, and LAG3, coupled with progressive loss of proliferative and cytotoxic potential and a later stabilization or decrease in inhibitory receptor expression once exhaustion is established. The results of this experiment mirrored these observations, with the percentage of cells co-expressing these three inhibitory receptors increasing from day 0 (unstimulated) through day 10, followed by a decrease as the cells become almost completely exhausted. See FIG. 5, which shows that at day 0 nearly all cells are unstimulated, and then nearly all cells are activated by day 4. From day 6 onward, the proportion of exhausted cells begins to rise through day 12/14, at which point nearly all cells were exhausted (top portion of each bar from day 6 to day 14).

Additionally, upon activation. CD8+ T-cells begin to secrete IFNγ and IL-2. However, with overstimulation, the cells begin to become exhausted. Typically, IL-2 production is lost early in the development of exhaustion, followed by decreased IFNγ production. This same trend was observed in this experiment, where IL-2 levels were greatest at day 4, where nearly all cells are activated, and decreased greatly at day 6 as cells become exhausted. See FIG. 5. The production of IL-2 was nearly absent on day 8, when a majority of cells reached an exhausted state. In parallel, IFNγ production followed IL-2, with peak production seen at day 6, which decreased rapidly by day 8.

While measurements of surface biomarkers and excreted cytokines in combination may provide useful information regarding cellular exhaustion status, none of the measurements alone provides an accurate picture of cell status. This sort of multi-faceted approach is laborious. Additionally, these method are not feasible in formalin-fixed paraffin embedded (FFPE) samples. To address these challenges, a model of measuring cellular exhaustion using RNA sequencing provides a direct, accurate, and precise measurement of exhaustion that can be rapidly determined.

The sequencing data for each time point was analyzed for cellular status using the methods and algorithms provided herein. Cellular status deconvolution was carried out using a deconvolution matrix comprising a set of cell status expression signatures or "fingerprints." The cell status expression signatures or "fingerprints" were generated using sequencing data obtained from samples substantially composed of specific cell status (e.g., a CD8+ exhausted cell fingerprint obtained from a purified population of CD8+ exhausted cells). The cell-status-specific fingerprints were then placed into the deconvolution matrix. This matrix was then applied to the complex data set of RNA sequencing and gene expression data to allow for identification of cellular status in the data and the relative proportions of each cell status. Included in the cell status expression signatures or fingerprints were genes that were significantly differentially expressed in pairwise cell status differential expression analysis as well as those genes that were expressed at a consistent level within cell states across biological replicates.

Ratio deconvolution was also performed. The process of determining individual components from bulk sequencing and expression profiles was accomplished by solving the matrix equation: $Ax=b$ where A was the cell expression fingerprints, x was the cell percentages, and b was the bulk expression counts. A vector regression method with data normalization was performed. See FIG. 3. Briefly, to deconvolve a mixture with N cellular states using M genes, the problem is set up according to FIG. 3. Cell fractions were determined and normalization across rows was performed. The expression counts of each gene were normalized to be in the range of 0 to 1 across each cell state and the sample in question such as a mixture of cells. All genes were weighted equally regardless of their absolute expression value.

Applying this deconvolution algorithm to the samples taken in this experiment, the expected state changes from unstimulated to activated to exhausted was observed. See FIG. 5, which shows the results of the above experiments including data for T-cell states (Unstimulated. Activation, and Exhaustion), percent max readout of cytokine concentration and flow of inhibitory receptors. The bar chart shows that at day 0 (unstimulated) all of the cells are identified as "Unstimulated," however as CD8+ T-cells are successively stimulated, starting at day 2, there is a concomitant increase in the percentage of cells identified as "Activation" through day 4. Even at day 6, the majority of cells are identified as "Activation." In contrast, day 6 begins to show an increase in the "Exhaustion" state model and the proportion of this cell state model increases all the way through to the final time point at day 14. The results of this experiment show that our T-cell state models are more robust than cytokine level or inhibitory receptor expression alone, and can be used to assess the contribution of each cell model in a pure mixture of in vitro CD8+ T-cells.

Example 2: Determination of Levels of Cell States in Purified PBMC Cells

Figure 6:
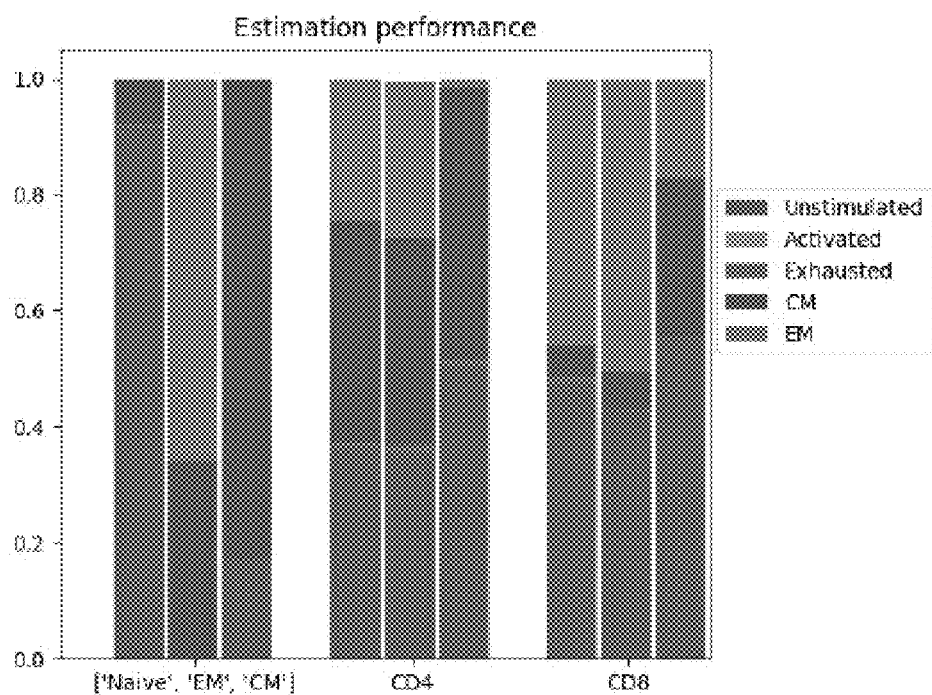
FIG. 6 shows a graph depicting the cellular status of various cell types in PBMC cells derived from healthy subjects as determined by the methods provided herein.

In order to assess the model on in vivo samples, blood was drawn from multiple donors and cell types were isolated using flow cytometry. CD8+ Naïve (Naïve; n=5), CD8+ Effector Memory (EM: n=5) and CD8+ Central Memory (CM: n=3) populations were isolated and sequenced to test the effectiveness of the model provided herein in identifying these CD8+ T-cell subtypes. FIG. 6 shows that our cell differentiation models were able to identify pure CD8+ subtypes with high accuracy (first three bars: naïve (left bar)=~90% of cells identified as unstimulated (bottom of bar), EM (middle bar)=~70% of cells identified as EM (top of bar), and CM (right bar)=~80% identified as CM (top of bar)) in representative samples.

The models were also applied to purified CD8+ cells derived from healthy donor peripheral blood mononuclear cells (PBMCs) (n=3) in order to determine the percentages of CD8+ cell subtypes. FIG. 6 (bars 7-9, right of image) shows the percentage of each cell status, with the top section of the bar indicating proportion of cells determined to be EM cells, the middle section indication proportion of cells determined to be CM cells, and the bottom section indicating the proportion of cells determined to be unstimulated. The approximate percentages of CD8+ cell states in healthy donors have been report as Naïve=60%+/−15%. EM=30+/−15%, CM=10%+/−5%, Activated=0% and Exhausted=0%. The percentages found using the models provided herein agree with these findings, with naïve cells accounting for approximately 50%, EM between 20-45%, and CM between 10-25%.

A similar experiment was performed using CD4+ cells derived from PBMCs of healthy donors (n=3). The approximate percentages of CD4+ cell subtypes in healthy donors have been reported as Naïve=50+/−12%, EM=20+/−10%, CM=30+/−5%, Activated=0%, and exhausted=0%. FIG. 6 (bars 4-6) show that the model provided herein can distinguish cell states in CD4+ T-cells from healthy patients, with naïve cells accounting for approximately 35-50% (bottom section of each bar), EM between 0-15% (top section of each bar), and CM 25-30% (middle section of each bar). These results exhibit the validity of using cell state motels to estimate T-cell state abundance.

Example 3: T-Cell Exhaustion Estimation from Mixed Control Exhaustion Samples In order to assess the use of the models provided herein in increasingly complex samples, sequencing data from the positive control exhaustion samples from Day 14 in Example 1 was mixed with non-exhausted negative control sample in increasing proportions (0%, 25%, 50%, and 100%). Negative samples included the CD45− (non-immune) component of dissociated tumor cell samples (DTCs) from lung (Lung), Melanoma (Mel), and Ovarian (OV) and an immune cell mix from healthy PBMC donors (Healthy PBMCs). The CD45− component from cancer samples and immune cells from PMBCs have no exhaustion component and thus serve as a negative exhaustion data set in the context of complex samples. The addition of these components thus creates a more complex sample with which to test the models provided herein.

Figure 7:
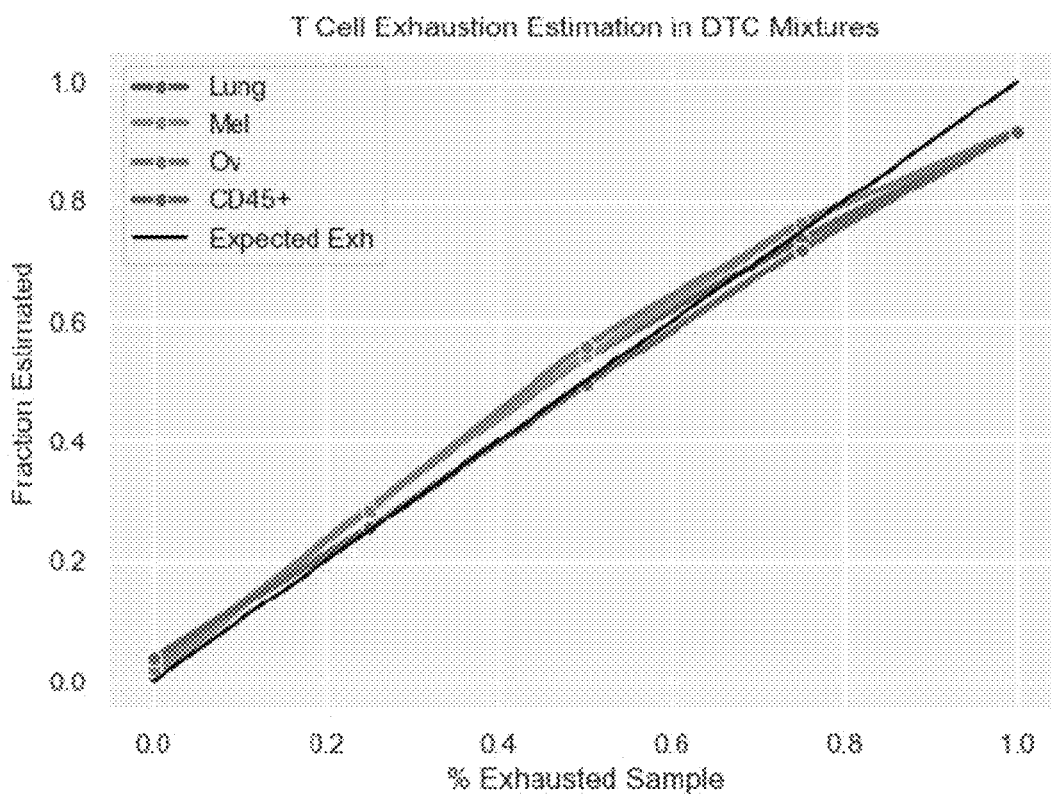
FIG. 7 shows a graph depicting predicted and measured T-cell exhaustion levels in a sample of exhausted T-cells mixed with unexhausted cells derived from various cancer tissues.

The resulting assessment of percentage of exhausted T-cells in the resulting mixtures with the cell status models provided herein matched closely the expected readouts. See FIG. 7, which shows model estimations of % Exhausted T-cells in sample (x-axis) compared to the expected fraction of exhausted T-cells (y-axis). Model estimations closely matched the expected readouts. From this data, the Exhaustion model is shown to be unaffected by noise from non-exhausted data (CD45− and PBMC immune cell mixes) and is able to estimate, with high accuracy and dynamic range, the fraction of exhaustion that exists in complex cancer samples from multiple indications.

Figure 8:
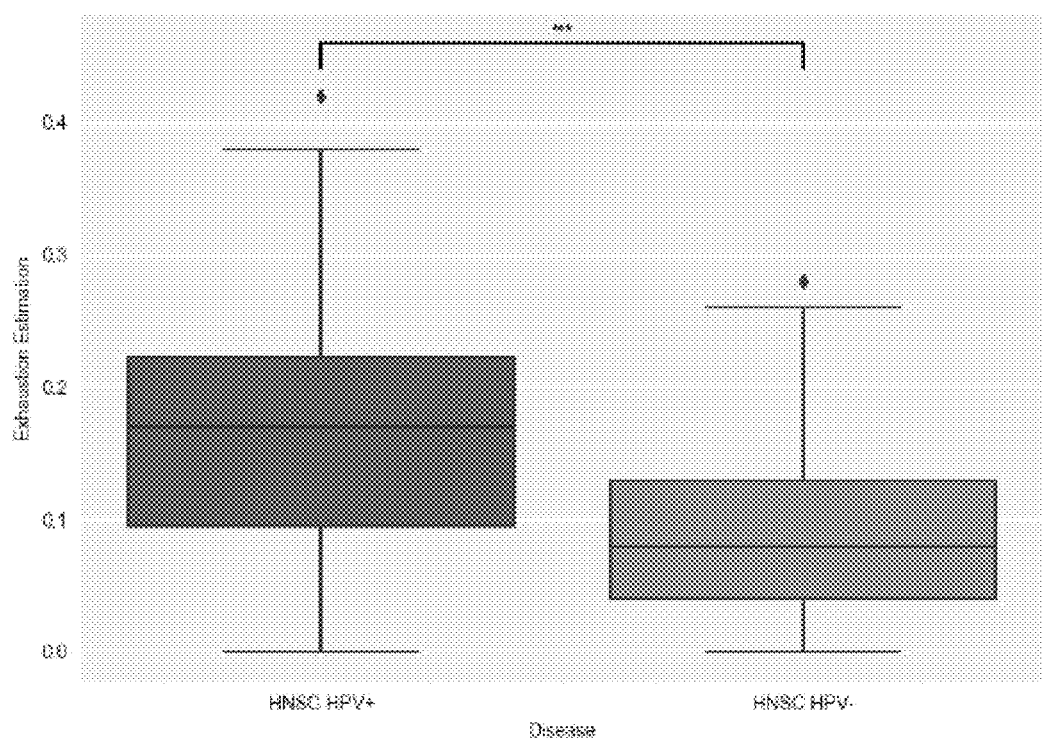
FIG. 8 shows a graph measuring exhaustion levels of cells derived from head and neck squamous cell carcinoma samples of HPV+ and HPV− patients using the methods provided herein.

Example 4: Exhaustion Estimation Using Head and Neck Squamous Cell Carcinomas The Exhaustion model was then evaluated in cancer samples expected to have differing levels of T-cell exhaustion. Head and Neck Squamous Cell Carcinoma (HNSC) biopsies display a higher level of exhaustion in Human papillomavirus-positive (HPV+) patients than HPV-negative (HPV−) patients. Using data from The Cancer Genome Atlas (TCGA), samples were grouped by HNSC HPV+(n=36) and HNSC HPV− (n=241) status. Transcriptome expression count data and models for Exhausted T-cells, Naïve T-cells, Activated T-cells. Effector Memory T-cells, and Central Memory T-cells were used to estimate the level of exhaustion for each sample. See FIG. 8, which shows estimated fraction of exhausted T-cells (y-axis) for HPV+ HNSC samples (left) and HPV− HNSC samples (right). The models estimated statistically more exhaustion (Student's t-test: p-value<0.001) in HNSC samples with HPV+ status (median=17%) versus those with HPV− status (median=8%). These results demonstrate the Exhaustion model provided herein corroborate primary research findings in "real world" data.

Example 5: RNA Model Discrimination of T-Cell States (TCS)

We created RNA models as a tool to estimate the prevalence of TCSs in newly sequenced FFPE samples or in public datasets. To do so, we isolated the cells that define each TCS (FIG. 9A), including naïve, effector memory (EM), and central memory (CM) CD8+ T cells, from healthy PBMC donors using flow cytometry. Activated and exhausted T cells were generated in vitro via continuous CD3/CD28/CD2 stimulation of isolated naïve CD8+ T cells. Cells of the Activated state corresponded to early stimulation which had maximal proliferative capacity according to IL2 and IFN-gamma expression. In contrast, cells of the Exhausted state corresponded to late chronic stimulation which had impaired cytokine production, limited to no proliferation, and high expression of PD-1, TIM3, and LAG3 inhibitory receptors, in line with observations in literature.

Figure 9A:
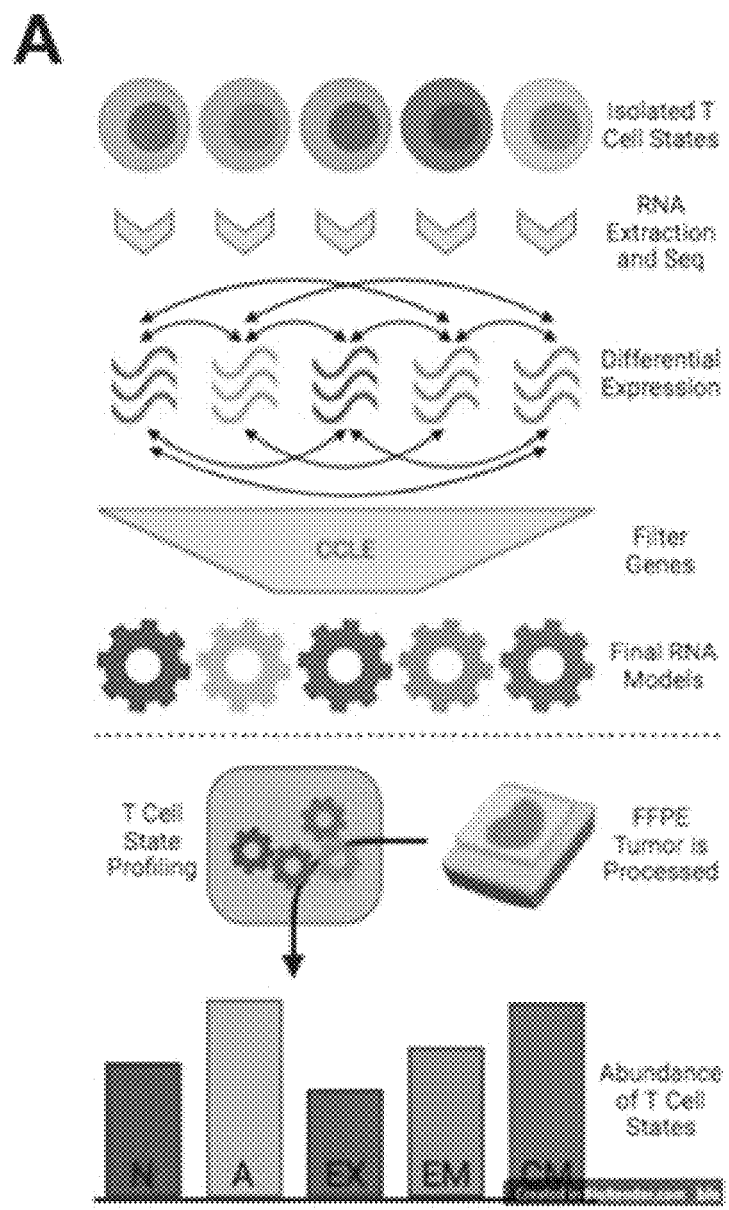
FIG. 9A shows a schematic of the approach to creating data driven T cell State models.

Total RNA isolated from these five types of cell isolates were respectively processed and sequenced. Differentially expressed genes were chosen to identify the five TCSs (FIG. 9A). Models for each of the five TCSs were created using the mean value for each of the genes for the five respective isolates. This data-driven approach has an advantage of being unbiased, which is especially important given the overlap between classical effector and exhaustion genes. These initial models adequately estimated TCS abundance in simple, PBMC based samples, but suffered from high false positive estimates in more heterogeneous tumor samples. To improve performance in complex samples, genes with relatively high expression in the cell lines of the Cancer Cell Line Encyclopedia (CCLE) were filtered out (FIG. 9A). The resulting five TCS RNA models were composed each of 46 genes (FIG. 9B).

These five models differentiate the five TCSs in heterogeneous FFPE tumor samples. Using these models and gene expression data from a sample, an unknown FFPE tumor sample can be characterized by solving a linear equation. The estimated abundances are a fractional number between 0 and 1 and represent what ratio of RNA in a whole sample is comprised of each TCS (FIG. 9A). With this in mind we report estimates multiplied by 100. We refer to the process of characterizing a sample in regard to TCSs as T cell state profiling (TCSP). TCSP characterizes the immune response in a tumor and, as shown later in this work, can predict patient response to anti-PD-1 therapy. Lending to the way the TCS models were created, TCSP can characterize public RNAseq data, providing the opportunity to characterize the infiltrating immune response in samples within and across many difference cancer types.

Figure 9B:
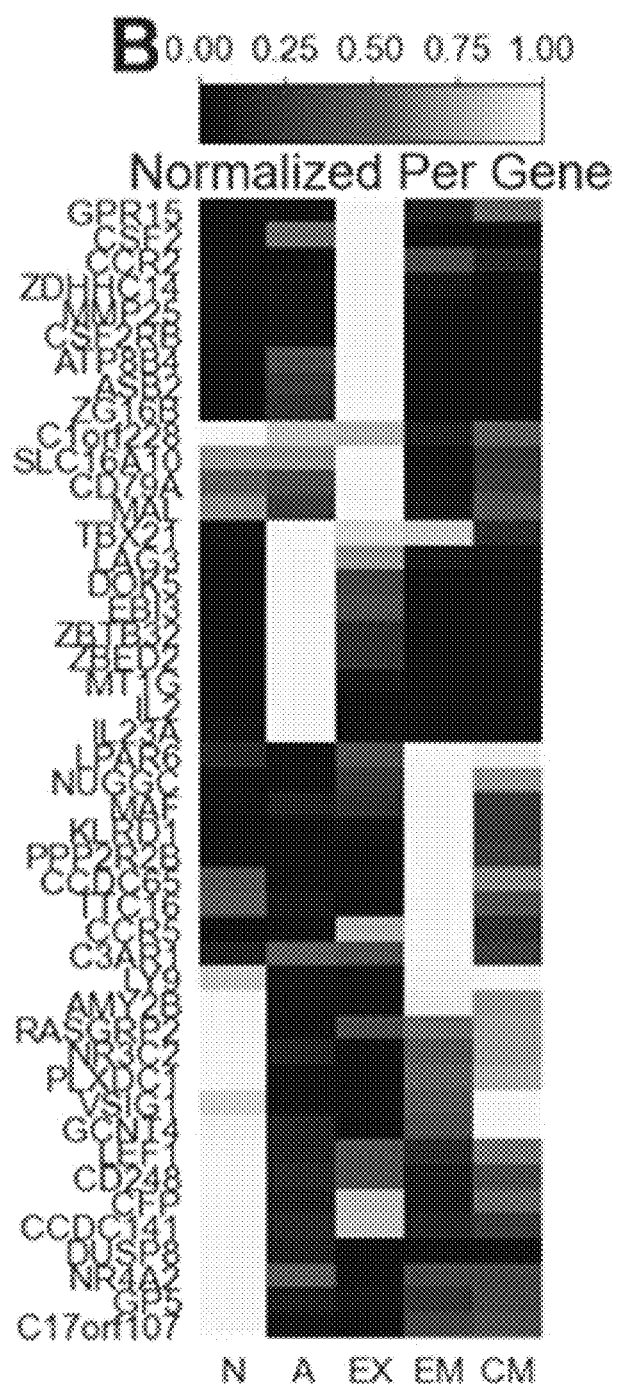
FIG. 9B shows a heatmap shows the gene-normalized expression of genes constituent of the 5 T Cell State models. N, Naïve model; A, Activated model; EX, Exhausted model; EM, Effector Memory model; CM, Central Memory model.
Figure 9C:
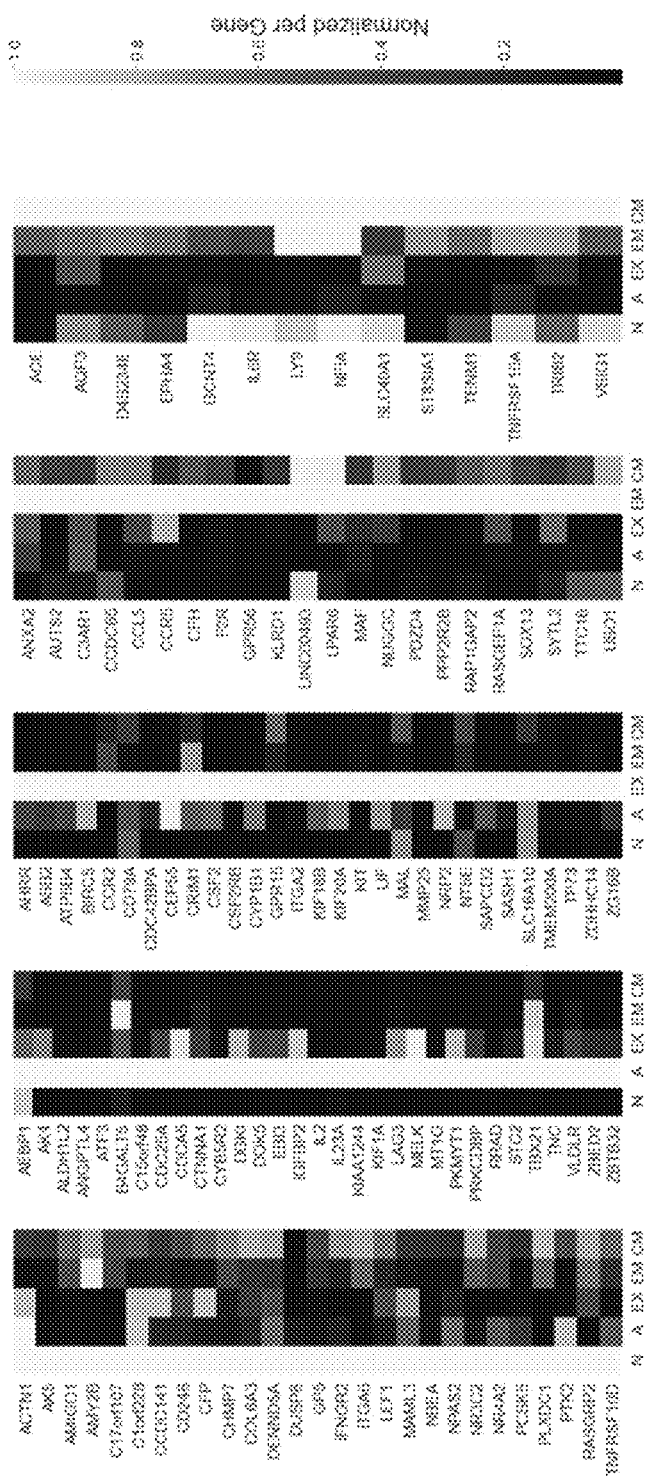
FIG. 9C shows a heatmaps showing gene-normalized expression of genes comprising the 5 T Cell State models before CCLE filtering.
Figure 9D:
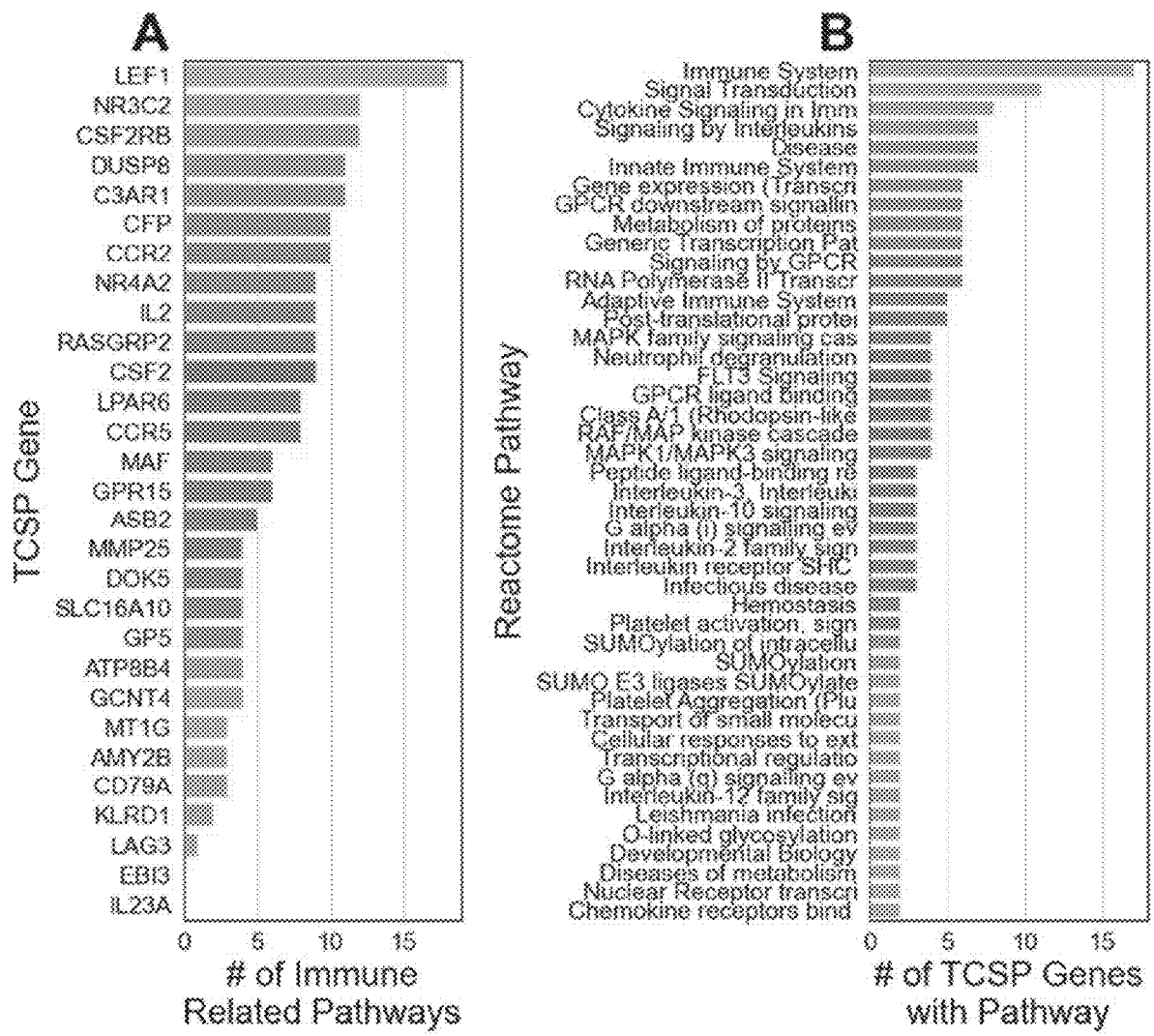
FIG. 9D shows reactome pathways associated with genes constituent of T-Cell State models. The A panel shows the number of immune related pathways counted for each gene. The B panel shows the frequency of individual pathways found across all T-Cell State genes.

We show the normalized expression of each gene across all five TCS models (FIG. 9B, FIG. 9C). Per the Reactome database, effectively all of these genes are involved in immunity related pathways (FIG. 9D). Each model has a few notable, constituent genes which characterize each TCS. The Naïve state model has high expression of LEF1, a gene involved in T cell development and peripheral T cell differentiation. A set of genes involved in homeostasis (NR4A2) and quiescence (CD248 and DUSP8) were also highly expressed in the Naïve model versus others. The Activated state model has high expression of cytokines related to inflammation and proliferation including EB13, IL2, and IL23A. The transcription factor TBX21 (T-Bet), which is involved in the regulation of development and CD4 differentiation, is highly expressed. The inhibitory receptor, LAG3 (HAVCR2), negatively regulates activation and was also a constituent gene of the activated state model. The Exhausted state model has high expression of CSF2, a gene associated with prolonged stimulation and cell aging. This state model also has the highest expression of genes that prohibit differentiation (ASB2), cell growth (CSF2RB), and inflammation (CCR2). The EM state model has high expression of KLRD1, which may regulate effector functions and cell survival of CD8 T cells. Additionally, MAF, a regulator of differentiation and function in a wide variety of T cells, and CCR5, a gene involved in chemokine-induced costimulation, were highly expressed. The CM state model has high expression of LY9, a gene that negatively regulates the development of memory CD8+ T cells. In addition, genes associated with trafficking (GCNT4) and adhesion (VSIG1) were also more highly expressed in the CM state.

Figure 10A:
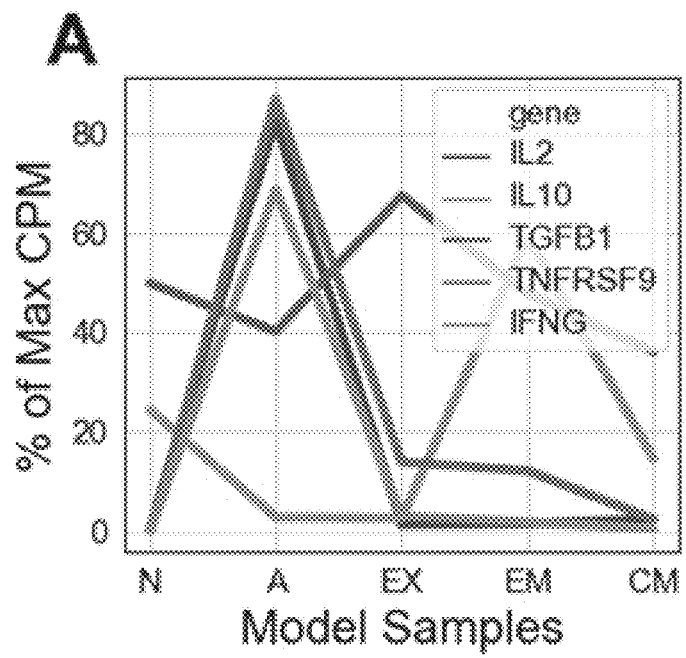
FIG. 10A shows average expression for activation associated cytokines across all donors for each T Cell State model, calculated as Counts per Million (CPM). Expression is normalized across T Cell State models for each gene. N, Naïve state model: A, Activated state model; EX, Exhausted state model: EM, Effector Memory state model; CM, Central Memory state model.
Figure 10B:
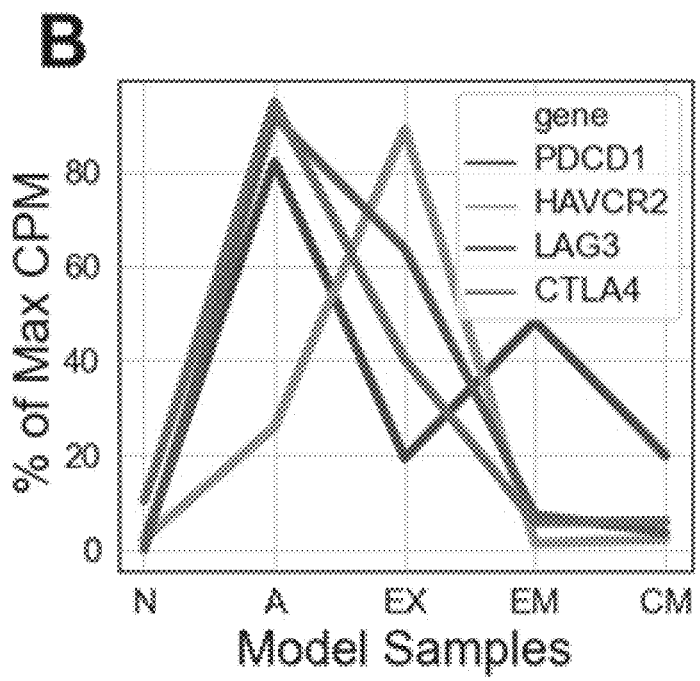
FIG. 10B shows average expression for exhaustion associated inhibitory receptors across all donors for each T Cell State model, calculated as Counts per Million (CPM). Expression is normalized across T Cell State models for each gene. N, Naïve state model: A, Activated state model; EX, Exhausted state model; EM, Effector Memory state model CM, Central Memory state model.
Figure 10C:
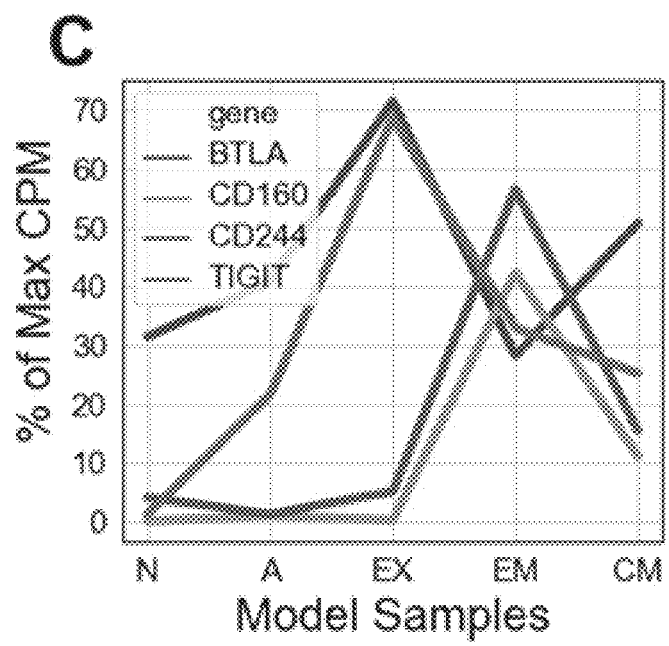
FIG. 10C shows average expression for various inhibitory receptors across all donors for each T Cell State model, calculated as Counts per Million (CPM). Expression is normalized across T Cell State models for each gene. N. Naïve state model; A, Activated state model: EX, Exhausted state model; EM, Effector Memory state model; CM, Central Memory state model.
Figure 10D:
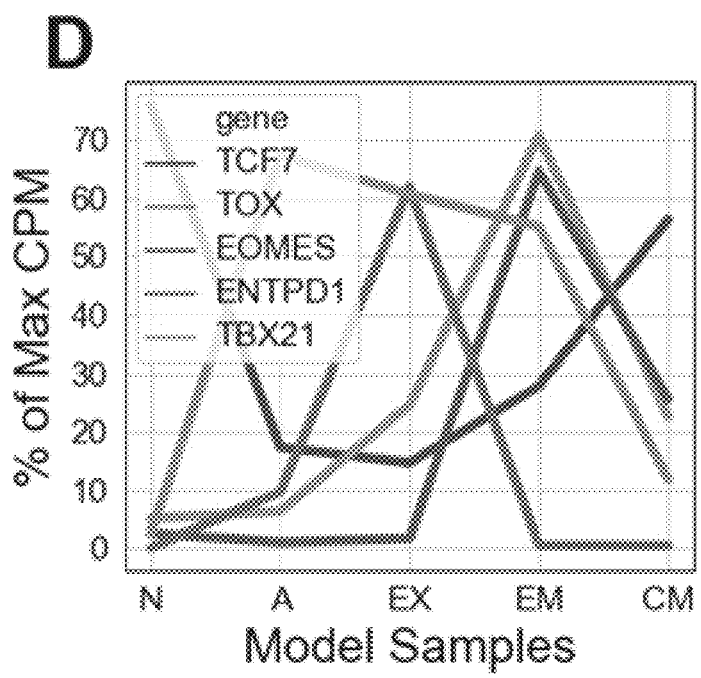
FIG. 10D shows average expression for exhaustion associated transcription factors across all donors for each T Cell State model, calculated as Counts per Million (CPM). Expression is normalized across T Cell State models for each gene. N, Naïve state model; A. Activated state model; EX, Exhausted state model: EM, Effector Memory state model: CM, Central Memory state model.
Figure 10E:
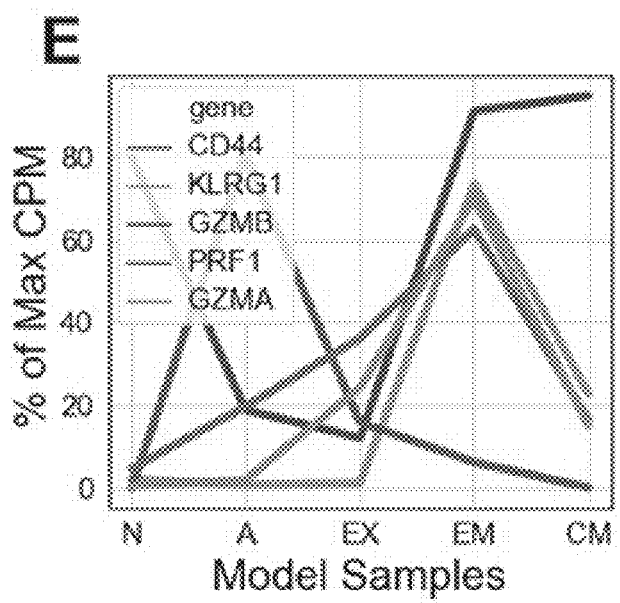
FIG. 10E shows average expression for effector associated genes across all donors for each T Cell State model, calculated as Counts per Million (CPM). Expression is normalized across T Cell State models for each gene. N, Naïve state model: A, Activated state model; EX, Exhausted state model; EM, Effector Memory state model; CM, Central Memory state model.

Interestingly, some canonical genes associated with the five TCSs in literature are missing from the models due to our data-driven approach. These genes are not differentially expressed between the 5 TCSs nor between the 5 TCSs and the tumor microenvironment (via the CCLE database) and therefore aren't useful for estimating abundances in the tumor microenvironment. For example, the Exhausted state model does not include other inhibitory receptors such as PD-1 (PDCD1) and TIM3 (HAVCR2) because these genes are also highly expressed in the activated state. Genes such as TCF7, TOX, EOMES, and CD39 (ENTPD1) were also not discriminative (FIG. 9C and FIGS. 10A-E). FIG. 10A, which shows activation associated cytokines, shows that IL-2, TNFRSF9, and IFNG were expressed at the highest levels in activated cells and nearly unexpressed in other states. Comparatively, TGFB1 was expressed at a nearly constant level of ~50-60%, whereas IL-10 showed low levels of expression, except in the EM state (60%). FIG. 10B, which shows exhaustion associated inhibitor receptors, shows that all four listed genes were largely unexpressed in the naïve state, with CTLA4, LAG3, and PCD1 reaching ~80% expression in the activated state. Conversely, HAVCR2 became most expressed in the exhausted state (~80%), but was only ~20% expressed in the activated state. PDCD1 remained at ~30% expression levels in the EX. EM, and CM states, whereas the other genes were largely not expressed in the EM and CM states. FIG. 10C shows other inhibitory receptors, including BTLA, CD160, CD244, and TIGIT. BTLA was expressed at ~30% levels in the activated state before reaching ~70% levels in the exhausted stated. Similarly, TIGIT also reach ~70% levels in the exhausted state, but was largely unexpressed in the naïve state. CD244 and CD160 showed largely the same expression profiles, being unexpressed in the N, A, and EX states before peaking at ~60% and ~40$ in the EM state respectively. FIG. 10D shows exhaustion associated transcription factors TCF7, TOX, EOMES, ENTPD1, and TBX21. TBX21 was largely unexpressed in the N state, ~70% expressed in the A state, before dropping across the graph to reach ~10% in the CM state. Conversely, TCF7 is expressed at ~80% in the N state and dropping dramatically in the A state, then rebounding in the CM state to ~60% ENTPD1 was largely unexpressed in all states except EX, where it was ~60%. EOMES and TOX followed largely similar patterns, both being expressed at ~70% levels in the EM state and largely unexpressed in other states, although TOX did reach ~25% in the EX state. FIG. 10E shows effector associated genes CD44, KLRG1, GZMB, PRF1, and GZMA. CD44 was expressed at ~80% or greater levels in the N, EM, and CM states and expressed at much lower levels in the A and EX states. GZMB was largely unexpressed in all states except the A state, where it reached ~80%. GZMA, KLRG1, and PRF1 all showed similar profiles, being expressed at low levels in all states except EM.

Example 6: T-Cell State Profiling is Analytically Robust in Accurately Determining T-Cell State The five TCS RNA models described in Example 5 were developed with the goal to characterize the immune response in heterogeneous specimens and predict response to anti-PD-1 therapy. Therefore, it is imperative that TCSP is accurate and analytically robust. This section focuses on the analytical experimentation done to validate the five TCSs and the TCSP technique.

Figure 12A:
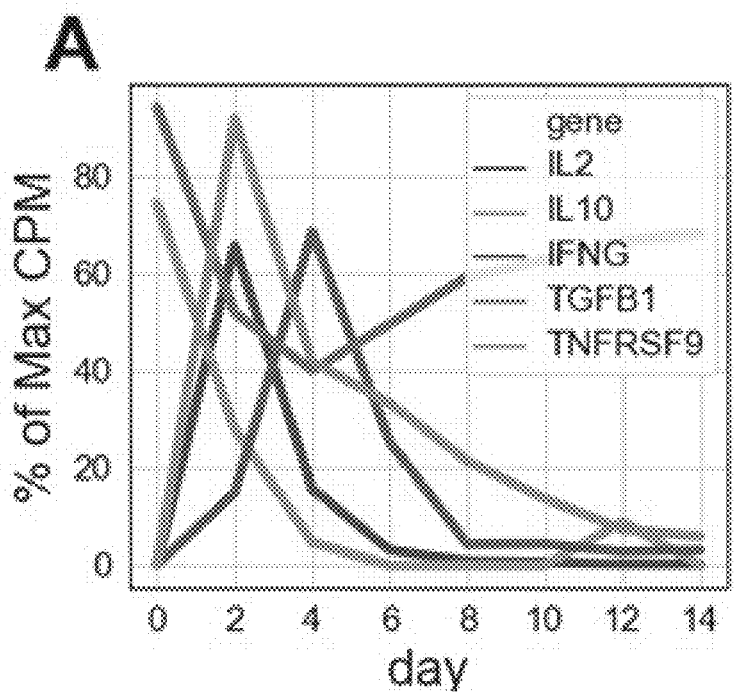
FIG. 12A shows gene expression for activation-associated cytokines of CD8 T cells during chronic stimulation In Vitro. Expression is normalized across time points for each gene.
Figure 12B:
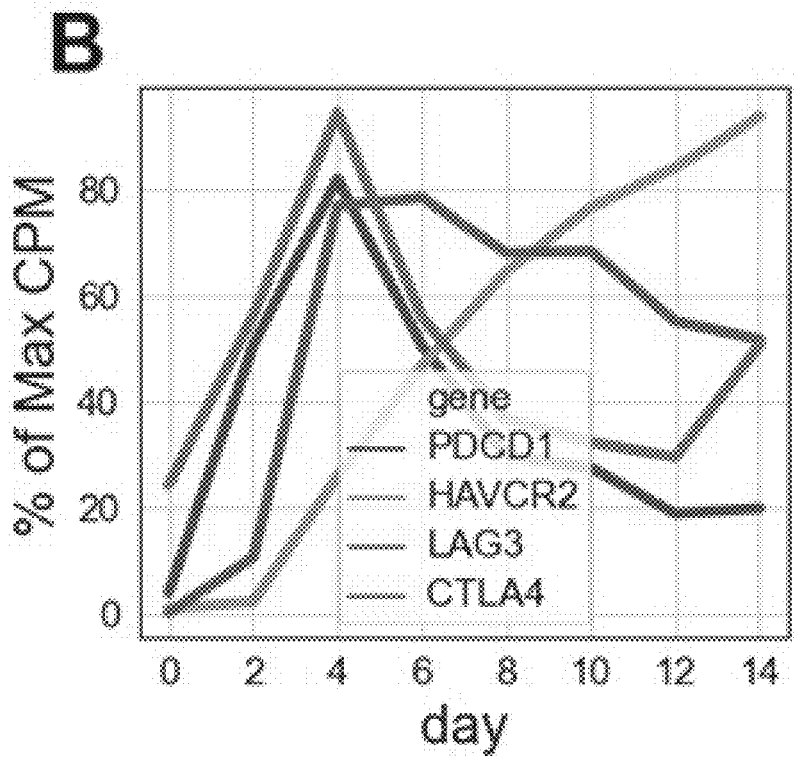
FIG. 12B shows gene expression for exhaustion-associated inhibitory receptors of CD8 T cells during chronic stimulation In Vitro. Expression is normalized across time points for each gene.
Figure 12C:
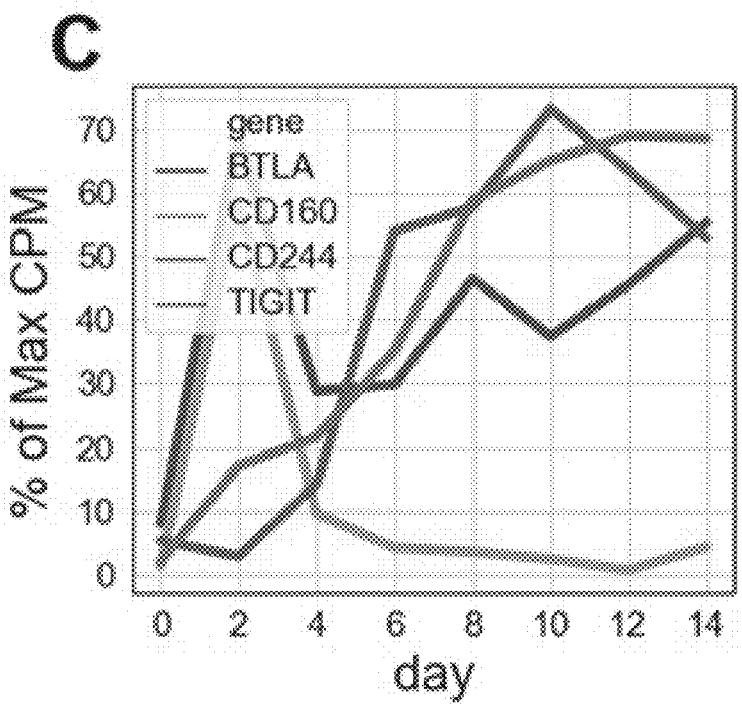
FIG. 12C shows gene expression for various inhibitory receptors of CD8 T cells during chronic stimulation In Vitro. Expression is normalized across time points for each gene.
Figure 12D:
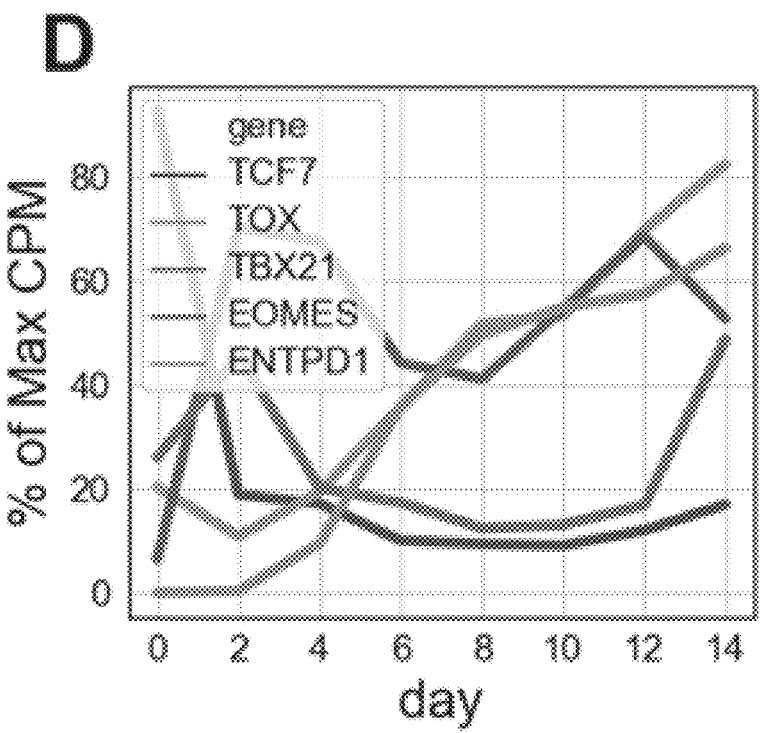
FIG. 12D shows gene expression for exhaustion-associated transcription factors of CD8 T cells during chronic stimulation In Vitro. Expression is normalized across time points for each gene.
Figure 12E:
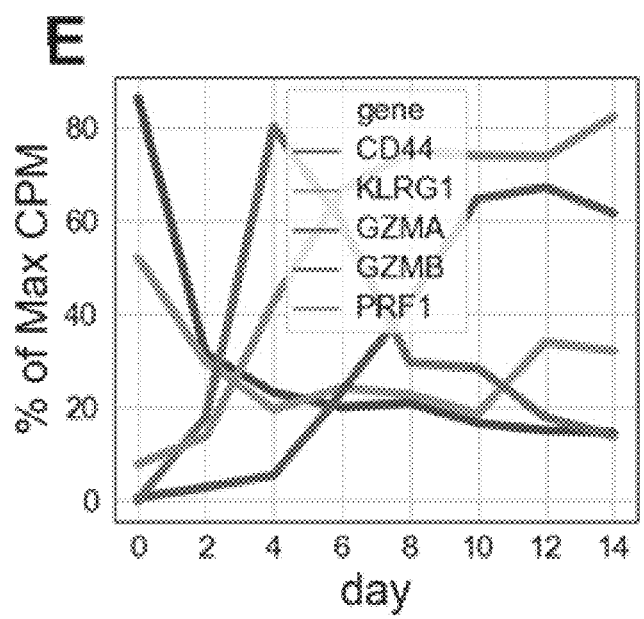
FIG. 12E shows gene expression for effector-associated genes of CD8 T cells during chronic stimulation In Vitro. Expression is normalized across time points for each gene.

First, we demonstrate the performance of the Naïve, Activated, and Exhausted state models. Naïve CD8 cells from a donor withheld from creating the models were chronically stimulated in vitro for 14 days. At days 4 and 6, there is a peak abundance of extracellular IL2 and IFN-gamma cytokines, respectively (FIG. 11A), which shows that at day 0 nearly all cells are unstimulated, and then nearly all cells are activated by day 4. From day 6 onward, the proportion of exhausted cells begins to rise through day 12/14, at which point nearly all cells were exhausted (top portion of each bar from day 6 to day 14). Meanwhile, the abundance of cells triple-positive for PD-1, TIM3, and LAG3 receptors grow through day 4 and peak at day 10, with sustained abundance into days 12 and 14 (FIG. 11A, FIG. 12B). FIG. 12A shows activation associated cytokines, with TGFB1 and IL10 showing expression at ~90% and ~70% levels at day 0, with TGFB1 dropping to ~50% as of day 4 and staying there and IL10 levels rapidly dropping to near 0%. Conversely, IL2, IFNG, and TNFRSF9 all start at ~0% on day 0 and reach peaks soon thereafter, with TNFSRF9 peaking at ~90% on day 2, IL2 peaking at ~60% on day 2, and IFNG peaking at ~70% on day 4, with all three of these dropping precipitously thereafter. FIG. 12B shows exhaustion associated inhibitory receptors, all of which start off with low expression at day 0. PCD1, LAG3, and CTLA4 all peak by day 4 at around 80-90%, with PCD1 and CTLA4 showing a quick drop off thereafter while LAG3 remains relatively steady over the next 6 days. Conversely, HAVCR2 does not peak until much later in the experiment, showing a slow rise in expression beginning on day 4. FIG. 12C shows other inhibitor receptors, with BTLA and CD160 showing peaks of 60-70% at day 2, with C160 dropping down near 0% by days 4 and 6 whereas BTLA hovers around 30-50% thereafter. CD244 and TIGIT show slowly increasing expression levels beginning on days 2-4, with a steady increase until peaks of ~60-70% are reached by day 7/8. FIG. 12D shows expression of exhaustion associated transcription factors. TCF7 begins at a high level of ~100% at day 0 before dropping to ~20% by day 2 and remaining there for the rest of the experiment. Conversely, the remaining exhaustion associated transcription factors start out a low concentration and increase throughout the rest of the experiment, with TBX21 reaching ~70% by day 2 and remaining between ~40-70% for the duration of the experiment. EOMES spiked to 40% at day 2, then hovered around 20% until day 14, at which point levels elevated to ~50%. TOX and ENTPD1 shows very similar expression curves to each other, the most notable difference being the day 0 expression levels of TOX being ~20% whereas ENTPD1 started near 0%. FIG. 12E shows effector associated gene expression levels. CD44 started at day 0 with near 100% expression levels which rapidly dropped to ~20% by day 4 and remained there for the rest of the experiment. KLRG1 showed a similar curve beginning at 50% levels and dropping to ~20% levels through day 10, at which point expression increased to ~30% for days 12 and 14. GZMB began at ~0% and reached peak expression on day 4 at 80% before rapidly dropping back to ~40% levels by day 8. PRF1 and GZMA showed similar trajectories, with both starting with little expression at day 0 (10% and 0% respectively) before ramping up to ~70% by the end of the experiment, although the expression curve of GZMA notably lagged behind PRF1 by about 2 days, with PRF1 peaking around day 8 and GZMA peaking around day 10. In accordance with previous studies, there is also: a progressive increase in expression of TIGIT, 2B4, CD39 (ENTPD1), and TOX, a progressive decrease in expression of LAG3 and GZMB after peak activation; and a peak of EOMES expression early and at the end of chronic stimulation (FIGS. 12A-E). This progressive increase in several inhibitory receptors, coupled with progressive loss of proliferative and cytotoxic and a later stabilization or decrease of inhibitory receptors is a hallmark of T cell exhaustion. These readouts suggest that in this chronic stimulation experiment the cells start out as naïve, became activated by day 4 and are exhausted by days 12 and 14. We compared these orthogonal measurements to TCS estimates. Our characterization matches this trend as day 0 is estimated to be in the Naïve state, day 4 is chiefly characterized as the Activated state, days 6 through 10 are characterized as a progressive transition from the Activated to Exhausted state, while days 12 and 14 are estimated to be in the Exhausted state (FIG. 11A).

Increased inhibitory receptor levels alone are not sufficient to determine the Exhausted state of a population of cell (FIG. 11A). Rather, it is the measurement of secreted cytokine levels after stimulation coupled with inhibitory receptor expression that enables one to approximate the Exhausted state of a group of cells. Performing this sort of multifaceted analysis is not only laborious, but also infeasible in FFPE tumor samples. Our Exhausted TCS model addresses these challenges and thus provides a powerful tool in profiling the immune response in a tumor.

Figure 11B:
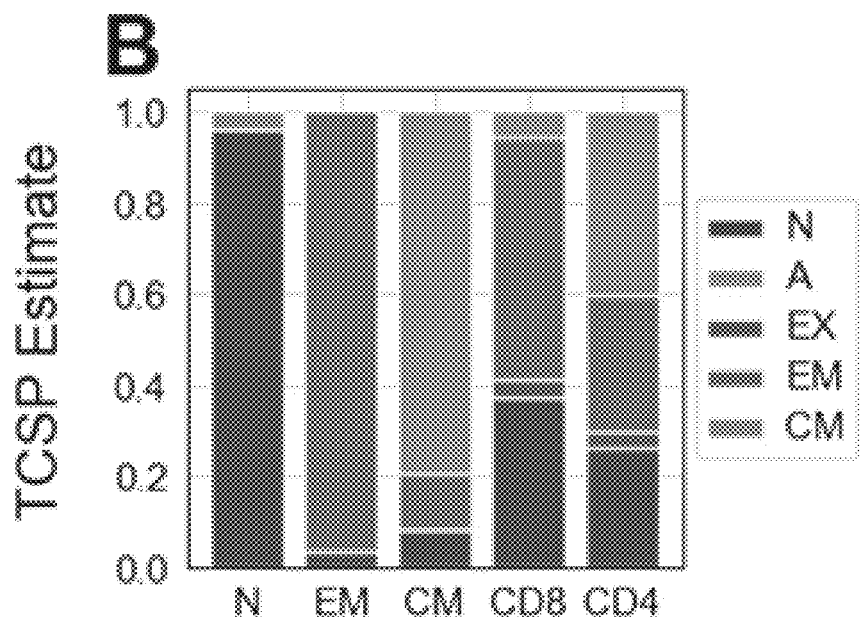
FIG. 11B shows T Cell state profiling results, specifically, the sum-normalized T Cell State estimates of T Cell populations isolated from blood: Naïve CD8+ T cells (N, n=5), Effector Memory CD8+ T Cells (EM, n=5), Central Memory CD8+ T Cells (CM, n=3), CD8+ T cells (CD8, n=8), and CD4+ T cells (CD4, n=8).

We next evaluated the performance of TCSP using PBMCs. For a single donor, live T cells were sorted for naïve, EM, and CM cells via flow cytometry. Samples were profiled and normalized to the total estimated abundance of all five TCSs. TCSP correctly characterized the naïve and EM isolates as predominately being Naïve and EM states, respectively. The CM isolate was estimated to be ~80% the CM state, but also estimated some fraction of the isolate to be Naïve and EM states (See FIG. 11B, which shows greater than 90% estimated naïve cells in the N population, greater than 90% estimated EM cells in the EM population, ~80% estimated CM cells in the CM population, ~25% naïve and ~60% EM cells in the CD8 population, and approximately equal amounts of naïve, EM, and CM cells in the CD4 population). We also profiled the CD4+ and CD8+ isolates of PBMCs from 8 donors. The CD8+ isolates had a mean estimate of 37% Naïve, 0% Activated, 4% Exhausted, 53% EM, and 5% CM, while the CD4+ isolates had a mean estimate of 26% Naïve, 0% Activated, 4% Exhausted, 30% EM, and 40% CM. The estimated abundances of the Naïve, EM, and CM states in CD4+ and CD8+ T cells reflect those reported in other healthy donors. The CD4 and CD8 samples are estimated to have a low level of exhaustion, perhaps due to latent viral infections, for example from Epstein-Barr Virus, where up to 2.5% of CD8+ T cells are specific to EBV in healthy individuals. These results suggest that TCSP can accurately estimate TCSs across both CD4+ and CD8+ T cells.

Figure 11C:
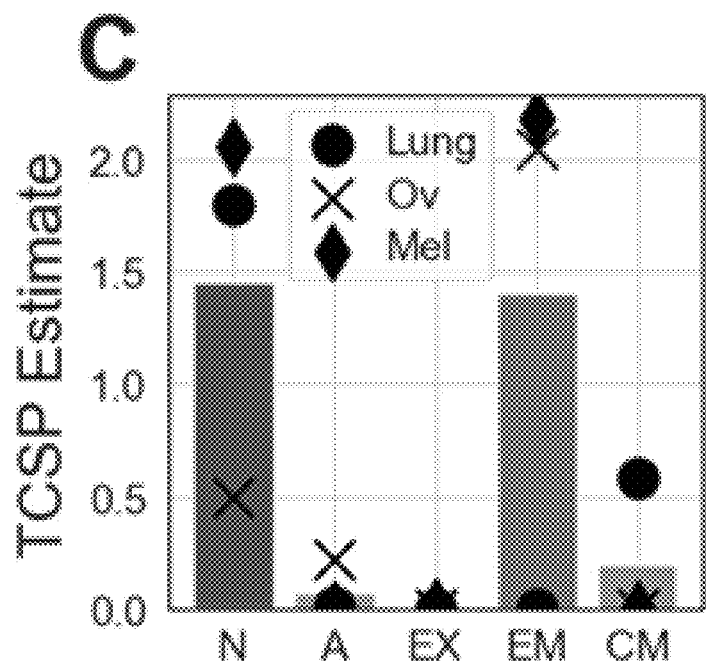
FIG. 11C shows T Cell state profiling results, specifically. T Cell state estimates of CD45− cells isolated from lung adenocarcinoma (Lung, n=1), ovarian adenocarcinoma (Ov, n=1), and melanoma (Mel, n=1) tumor samples.
Figure 11D:
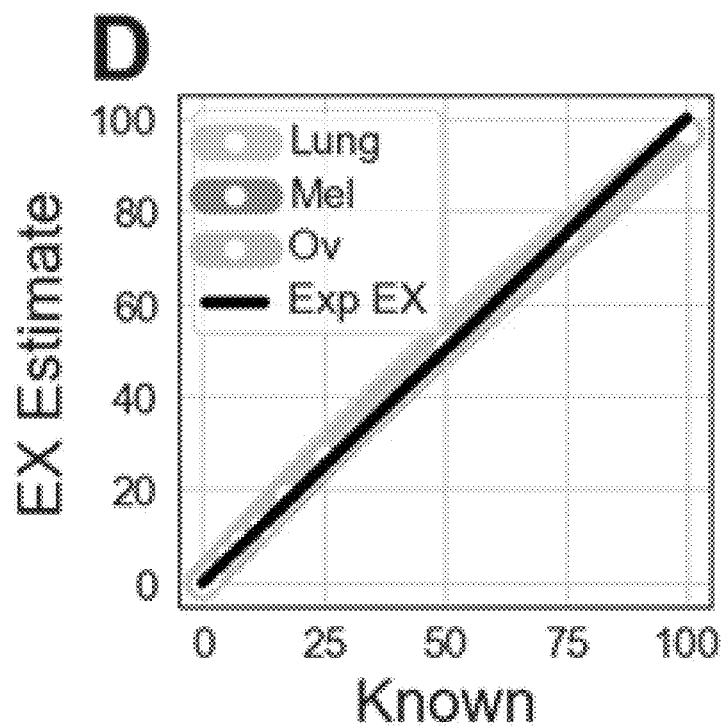
FIG. 11D shows T Cell state profiling results, specifically exhaustion model estimates of synthetic samples comprised of varying fractions of chronically stimulated CD8 T cells (day 14 from FIG. 11A) and CD45− cells isolated from tumor samples (from C).
Figure 11E:
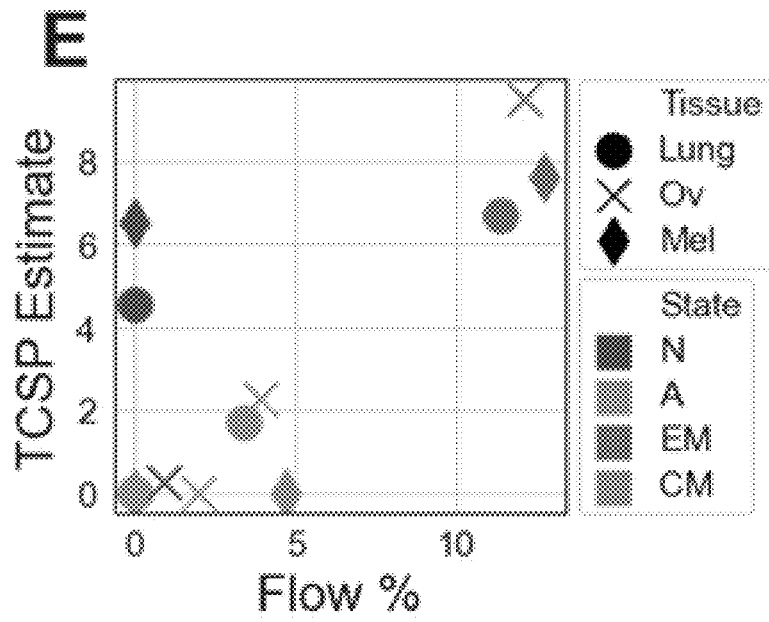
FIG. 11E shows T Cell state profiling results, specifically T Cell State Profiling of whole tumor samples (from C) compared against canonical flow cytometry estimation.
Figure 13:
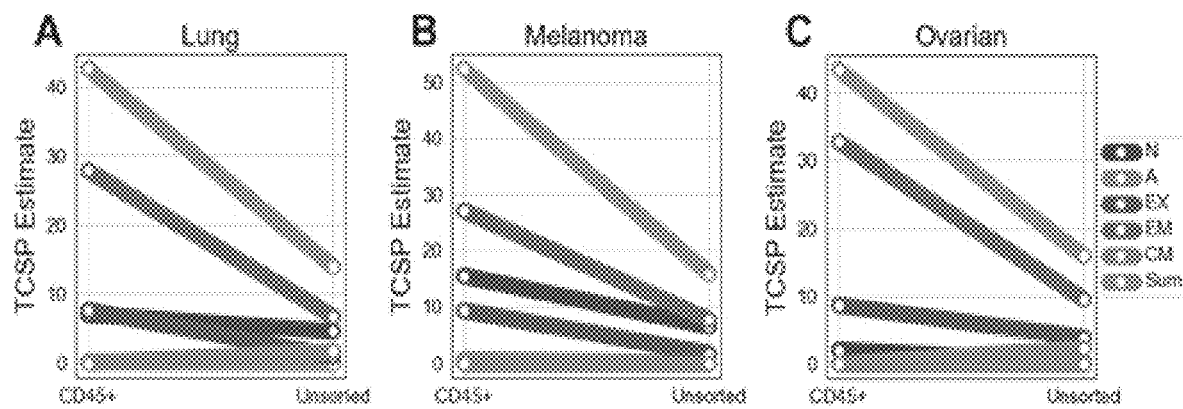
FIG. 13 shows T cell state model estimates from tumor samples. Cells from fresh tumors (Unsorted) were dissociated and sorted for CD45+ immune isolates (CD45+). Estimates are shown for three different tumor types (from FIG. 14C: A), Lung Adenocarcinoma (Lung); B), Melanoma; and C). Ovarian Adenocarcinoma (Ovarian). N, Naïve state model; A, Activated state model; EX, Exhausted state model; EM, Effector Memory state model: CM, Central Memory state model; Sum, Sum of all five state models.

TCSP of the tumor microenvironment is challenging because immune cells are integrated in and affected by a heterogenous mix of tumor and stroma. Therefore, we next aimed to validate performance with various isolates of dissociated tumor cells from single donors of lung cancer, melanoma, and ovarian cancer. CD45− isolates are devoid of immune cells and so were sorted to establish the specificity of TCS estimates. The average estimates across the three tissue types are <0.25 (out of 100 parts) for Activated and CM models, and effectively 0 for the Exhausted model (FIG. 11C). On average, the Naïve and EM models suffered from higher false positive estimation, although still very low and to different degrees depending on the cancer type (FIG. 11C). We further sought to explore the sensitivity of profiling the Exhaustion state by titrating RNA-seq data from an exhausted sample (from day 12 of the chronic stimulation) into the CD45− sample, in silico. In fractions of 1% to 100% exhausted reads, we see a reliable estimate when independently titrating in the 3 different cancer types (FIG. 11D). In these titrations, the level of the other four TCSs was at or near 0. Finally, we considered the unsorted lung, melanoma, and ovarian samples consisting of a mix of immune, stromal, and cancer cells. Estimates of these three samples correlate with flow cytometry measurements for EM, CM, and activated TCSs (FIG. 11E). The Naïve cell state was estimated to be higher than what was measured by flow cytometry, which may be a result of reduced specificity for this state (FIG. 11C). As described before, it is not possible to functionally characterize exhaustion level with only flow cytometry and so we were not able to evaluate our exhaustion estimates in these 3 samples. However, when comparing CD45+ isolates to the unsorted samples, the order of Exhausted state estimates are preserved among TCSs (FIG. 13). In FIG. 13, each of panels A B, and C all have the bar representing "sum" at the top of the figure, with the "EM" bar next beneath it. In panel A, both N and EX bars are at ~10% for the CD45+ sample, with the EX cells reaching ~0% in the unsorted. In panel B, N cells are at ~15% in CD45+ cells, EX cells at ~10% in CD45+ cells, and CM cells are at about 0% in CD45+ cells. In panel C. EX cells are at ~10% in CD45+, with the remaining cell states all near 0%. In all, these results build confidence in TCSP of infiltrating T cells in heterogeneous tumor samples.

Example 7: T-Cell State Profiling is Consistent with External Observations

TCSP is robust in estimating TCSs and can be used to characterize public datasets, making TCSP unique in its ability to investigate many biological and clinical questions across specimen types and datasets. In addition, the breadth of our functionally validated TCS models enables a uniquely detailed, yet comprehensive approach to investigate TCSs in the context of chronic infection and cancer. As such, we next sought to corroborate external observations in literature. Given the unique ability of TCSP to measure exhaustion in preserved clinical samples using our functionally valid model, we focused inquiry on T cell exhaustion.

We performed TCSP on a set of previously characterized CD39+ and CD39− sorted cell isolates from Non-small Cell Lung Cancer (NSCLC) and Colorectal Cancer (CRC) (Simoni, Yannick et al. *Nature* 557, 575-589(2018)). CD39+ tumor infiltrating T cells have been associated with both exhausted and effector memory phenotypes. As observed previously (Canale, Fernando P. et al., Cancer Res; 78(1); 115-28), both CD39+ and CD39− T cell isolates were estimated to be primarily in the EM state (FIG. 14A). In addition, we confirmed that the CD39+ isolate exhibited a higher relative exhaustion score than CD39− T cells (FIG. 14B). These two trends held in both subsets when NSCLC and CRC samples were analyzed individually (FIG. 15A and FIG. 15B). In FIG. 15A, for each cell status, the bars are arranged from left to right as CRC CD39−, CRC CD39+, NSCLC CD39−, and NSCLC CD39+.

Figure 14C:
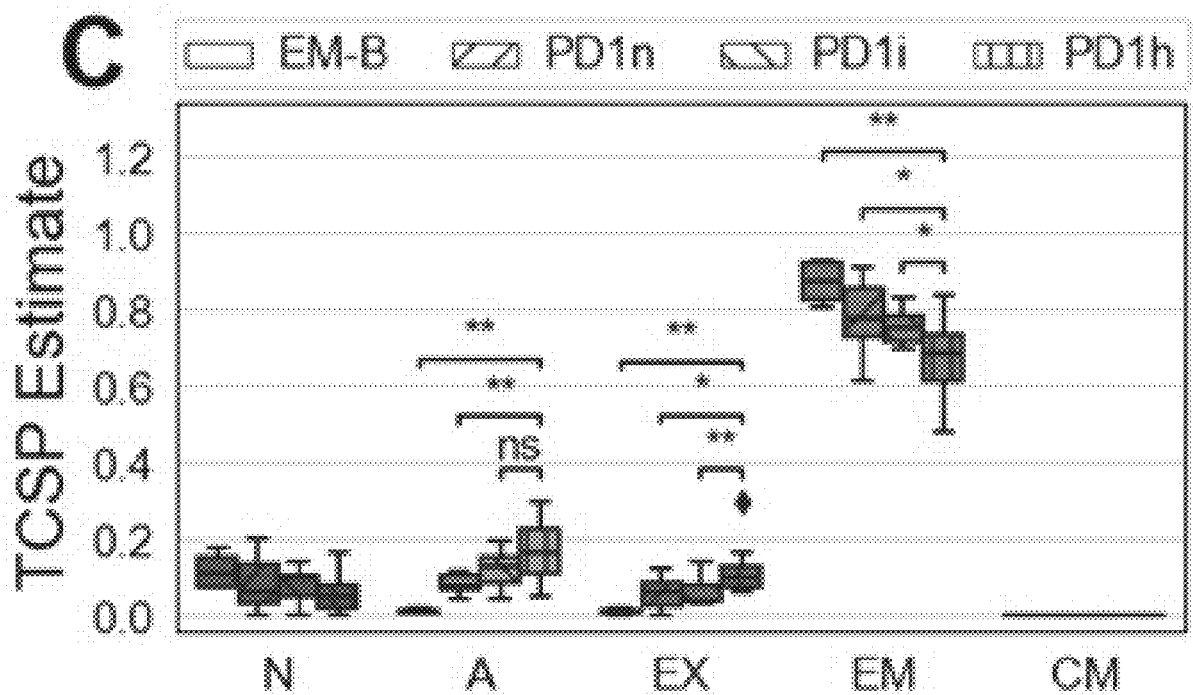
FIG. 14C shows sum-normalized T Cell State estimates for CD8+ T cell isolates sorted by varying levels of PD1 expression. EM CD8+ T cells isolated from blood (EM-B, n=4) were compared against CD8+ T cells isolated from NSCLC tumors with no PD1 (PD1n, n=11), intermediate PD1 (PD1i, n=11), and high PD1 (PD1h, n=11) expression.

High PD-1-expressing infiltrating T cells have also been associated with exhaustion. A previously characterized set of cell isolates from blood and NSCLC tumors (Thommen, Danila S. et al., Nature Medicine, 24, 994-1004(2019)) were profiled for TCSs. Exhausted model estimates increased as PD-1 expression increased in isolates, corroborating previous observations (FIG. 14D). EM cells isolated from blood had the lowest Exhausted estimates, while PD-1 high isolates from tumors had the highest. Similarly, Activated state estimates were positively correlated with PD-1 expression. Conversely, Naïve and EM model estimates were negatively correlated with PD-1 expression (FIG. 14C, FIG. 15D). This suggests that expression of PD-1 in CD8 infiltrates, along with expression of other classical inhibitory receptors (FIG. 15C), correlates with a population of cells that are increasingly antigen experienced with a decreasing effector function. In FIG. 15C, for each exhaustion associated inhibitor receptor in CD+ T cells, the leftmost bar represents expression levels in EM CD8+ T cells isolated from blood (EM-B, n=4), and the remaining bars show the pertinent expression level of exhaustion associated inhibitor receptor in CD8+ T cells isolated from NSCLC tumors with no PD1 (PD In, n=11), intermediate PD1 (ID1i, n=11), and high PD1 (PD1h, n=11) expression (left to right).

Figure 14E:
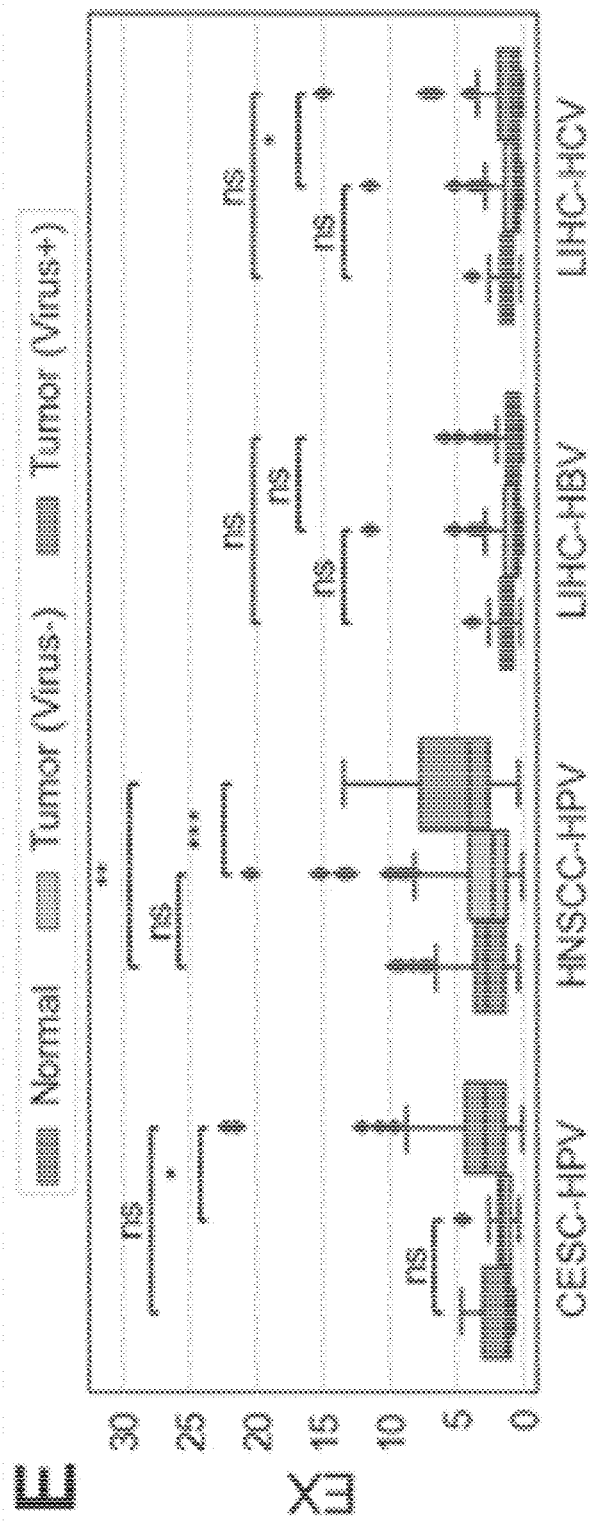
FIG. 14E shows Exhaustion estimates for normal and tumor tissue from three cancers with viral etiologies.
Figure 16A:
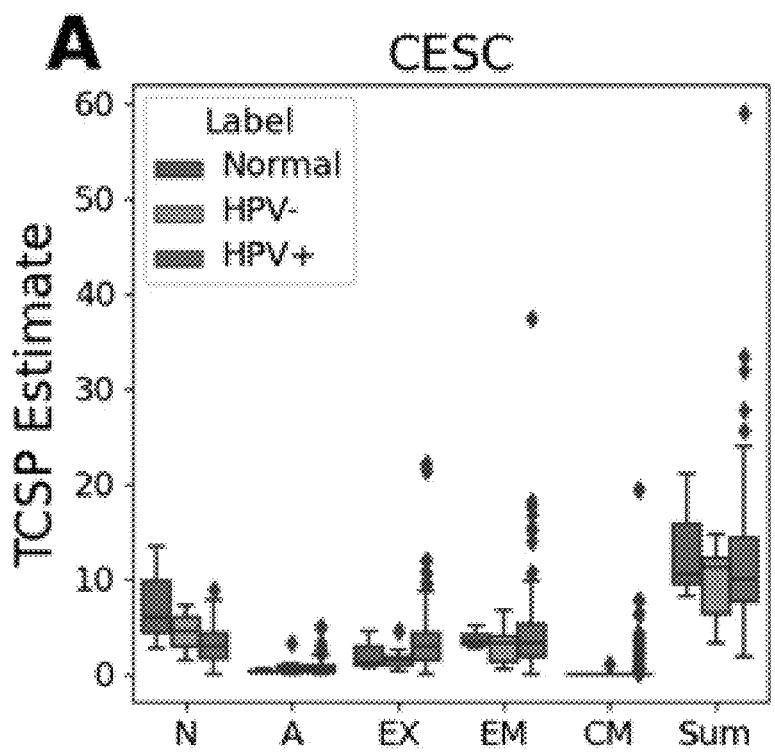
FIG. 16A shows T Cell State Profiling of normal and tumor tissue from Cervical Squamous Cell Cancer (CESC) with viral etiologies. Samples were grouped as tumor normal (Normal), tumor without viral infection (Tumor Virus−), and tumor with viral infection (Tumor Virus+) There are the following normal, tumor (virus−), and tumor (virus+) samples: CESC, 3/9/169.
Figure 16B:
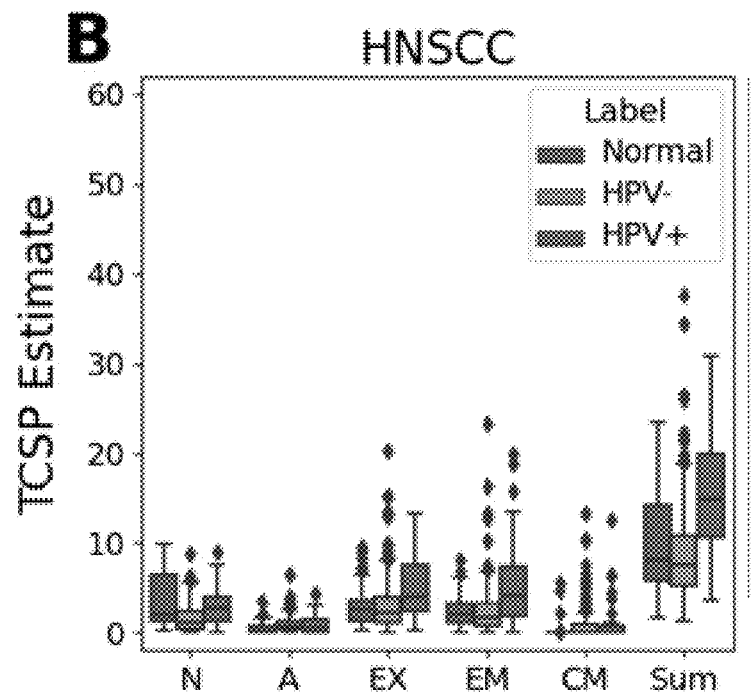
FIG. 16B shows T Cell State Profiling of normal and tumor tissue from Head and Neck Squamous Cell Cancer (HNSCC) with viral etiologies. Samples were grouped as tumor normal (Normal), tumor without viral infection (Tumor Virus−), and tumor with viral infection (Tumor Virus+). There are the following normal, tumor (virus−), and tumor (virus+) samples: HNSCC, 44/241/36.
Figure 16C:
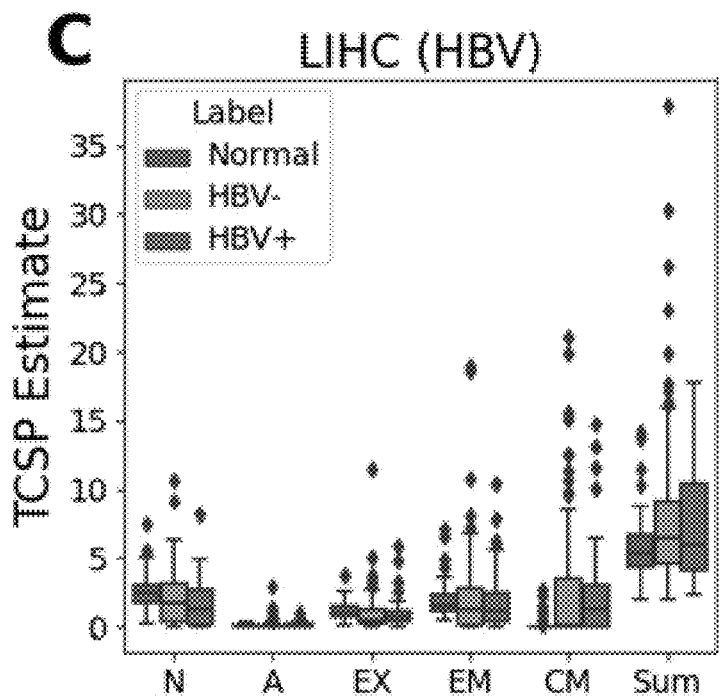
FIG. 16C shows T Cell State Profiling of normal and tumor tissue from Liver Hepatocellular Carcinoma (LIHC) with Hepatitis B (HBV) viral etiologies. Samples were grouped as tumor normal (Normal), tumor without viral infection (Tumor Virus−), and tumor with viral infection (Tumor Virus+). There are the following normal, tumor (virus−), and tumor (virus+) samples: LIHC-HBV, 50/118/44.
Figure 16D:
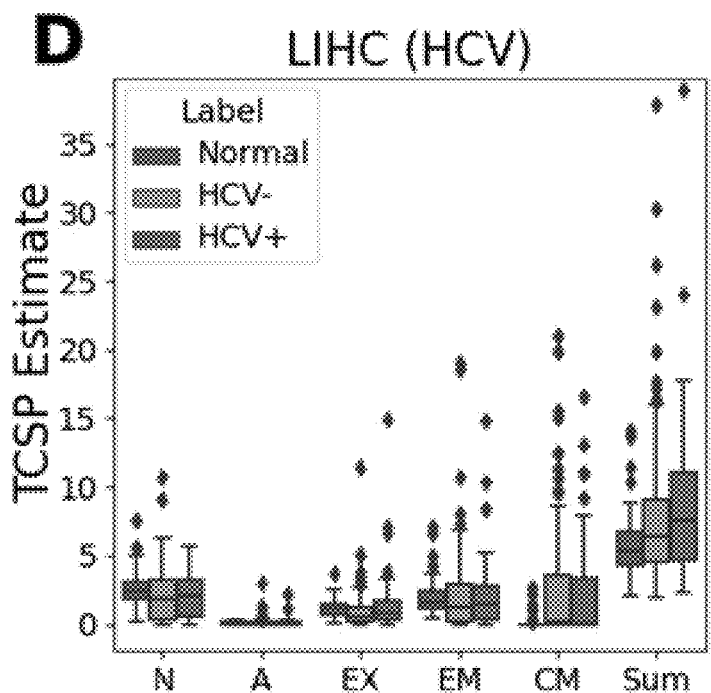
FIG. 16D shows T Cell State Profiling of normal and tumor tissue from Liver Hepatocellular Carcinoma (LIHC) with Hepatitis C (HCV) viral etiologies. Samples were grouped as tumor normal (Normal), tumor without viral infection (Tumor Virus−), and tumor with viral infection (Tumor Virus+). There are the following normal, tumor (virus−), and tumor (virus+) samples; LIHC-HCV, 50/118/35.

T cell exhaustion and dysfunction may be caused by a variety of factors, but are typically associated with persistent, chronic antigen stimulation. This model of exhaustion has its origins in viral research but has also been demonstrated in solid tumors. We investigated viral and tumor induced exhaustion in tandem, by performing TCSP on solid tumors with etiologies involving persistent viral infection. In Cervical Squamous Cell Cancer (CESC), exhaustion was highest in tumor samples with HPV infection, as previously suggested (See, e.g. Ming, Ying et al., J Cancer 2018; 9(16): 2938-2945) (FIG. 14E). Interestingly, TCS estimates suggest that naïve T cells decrease in abundance from normal tissue to HPV− to HPV+ tumor tissue (FIG. 16A). In Head and Neck Squamous Cell Cancer (HNSCC), exhaustion was highest in HPV+ tumor samples, as previously observed (See, e.g. Gameiro, Steven F. et al, Oncoimmunology. 2018 Jul. 30; 7(10)e1498439) (FIG. 14E). In FIG. 14E, for each cell type the bar representing "normal" cells is at left, "Tumor (Virus−)" is in center, and "Tumor (Virus+)" is at right. In addition, a higher estimated abundance of total T cell infiltrate in HPV+ tumor samples corroborate previous HNSCC research (Lechner, Axel et al. Oncotarget. 2017 Jul. 4; 8(27)44418-44433) (FIG. 16B). In each of FIGS. 16A-C, the bars representing normal, HPV−, and HPV+ bars are shown from left to right. Similarly, FIG. 16D shows normal, HCV−, and HCV+ from left to right. In Liver Hepatocellular Cancer (LIHC), the exhaustion trends weren't as apparent, as exhaustion was only estimated to be higher in tumors with active HCV infections, but not HBV infections (FIG. 14B). TCSP was similar across both malignant and non-malignant tissue, and regardless of viral status. Other observations in literature (Cell. 2017 Jun. 15; 169(7):1327-1341.e23) also indicate few differences in T cell exhaustion, T cell type, and T cell abundance when comparing viral status in this LIHC dataset. Yet, in line with our estimates, other work has found HCV specific T cells to be highly exhausted. These data suggest that exhausted T cells are increased in at least some tumor types during concurrent viral infection, and may be dependent on the type of virus.

Example 8: T-Cell State Profiling Predicts Anti-PD-1 Response

TCSP is robust in measuring biologically relevant physiology. In addition, T cell biology is heavily implicated in the method of action of immunotherapies, especially in HNSSC, NSCLC, and Melanoma. Therefore, we used TCSP to study and retrospectively predict anti-PD1 therapy in these three cancer types.

Figure 18A:
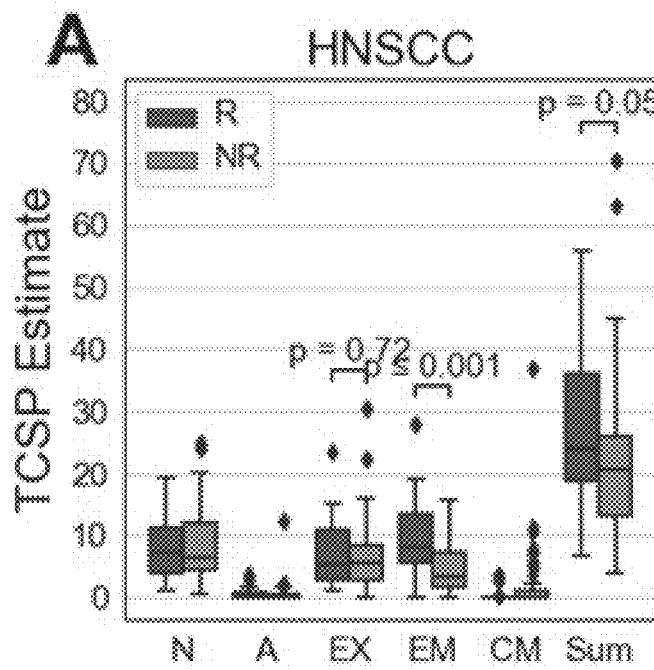
FIG. 18A shows T Cell state profiles of responders (R) and non-responder (NR) to anti-PD1 treatment a cohort of patients with recurrent and metastatic Head and Neck Squamous Cell Cancer (HNSCC). Hypothesis was tested using the one-sided Mann-Whitney U test.

First, we investigated response in recurrent and metastatic HNSCC. This cohort of 85 samples consists of non-nasopharyngeal samples collected from patients at Washington University and processed in house. With TCSP, we found that the EM state was more abundant in tumors of responders and that overall T cell infiltrate was higher in responders, in line with other work (Hanna, Glenn J. et al. JCI Insight. 2018 Feb. 22; 3(4):e98811) (FIG. 17A, FIG. 18A). Using machine learning, we built a multianalyte biomarker to predict response to anti-PD-1 treatment in this indication. We used bootstrap sampling to best approximate future performance in an independent validation set. Notably, this biomarker (AUC=0.70) better predicted objective response relative to PD-L1 IHC (CPS>=1) testing (AUC=0.62), which is an indicated companion diagnostic in this cohort (FIG. 17B). The TCSP based biomarker also predicted overall survival outcomes, with predicted responders having longer survival (FIG. 17C).

Figure 18B:
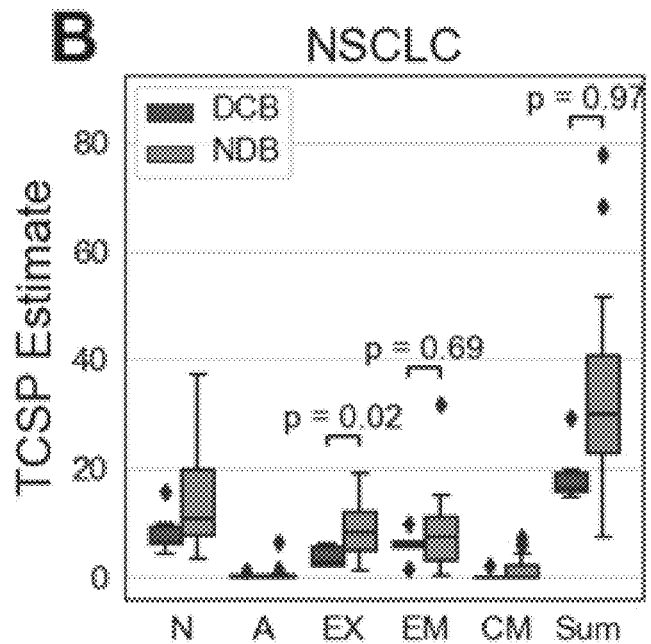
FIG. 18B shows T Cell state profiles of responders and non-responder to anti-PD treatment in a cohort of patients with recurrent and metastatic Non-small Cell Lung Cancer (NSCLC). The alternative hypothesis is that EX, EM, and Sum are higher in patients with durable clinical benefit (DCB, n=6) vs non-durable benefit (NDB, n=15). Hypothesis was tested using the one-sided Mann-Whitney U test.

Next, we considered a cohort of recurrent and metastatic NSCLC patients with primary tumors that were treated with anti-PD-1 therapies in early lines (Thommen, Danila S. et al., Nature Medicine, 24, 994-1004(2019)). We investigated the differences between 21 patients with durable clinical benefit (DCB) and non-durable benefit (NDB). DCB was defined as complete response (CR), partial response (PR), or stable disease (SD) as defined by RECIST 1.1 for at least 6 months. Similar to HNSCC, we observed a greater proportion of exhausted and EM T cells in NDB and DCB samples, respectively (FIG. 17D, FIG. 18B).

The sum-normalized Exhausted and EM state observations measured from FFPE tissue in two different cancers are reminiscent of the characteristics observed in tumor-isolated T Cells gated on CD39 and PD-1 (FIG. 14A and FIG. 14C) and suggest that CD39+ and/or PD1+ T cell populations may be higher in responders in both cancers. This corroborates the previously observed association of PD-1+ T cells and response in NSCLC. In this NSCLC cohort, we also observed that estimates of exhaustion were higher in NDB patients, consistent with previous work (Hu-Lieskovan S et al., Clinical Cancer Research, 20 May 2019, 25(16):5061-5068) (FIG. 18B). In contrast with previous work (Hu-Lieskovan S et al., Clinical Cancer Research, 20 May 2019, 25(16):5061-5068), however, we found that total infiltrate levels were higher in this population of NDB patients (FIG. 18B). Similar to HNSCC, we used the TCSP readouts as inputs to train a multianalyte biomarker and evaluate the performance in predicting DCB in NSCLC. The TCSP biomarker better predicted DCB (AUC=0.78) compared to both the indicated companion diagnostic, PD-L1 IHC (AUC=0.73), and also Tumor Mutational Burden (AUC=0.71) (FIG. 17E). In addition, patients predicted to have DCB by the TCSP-based biomarker had significantly longer overall survival (FIG. 17F).

Figure 18C:
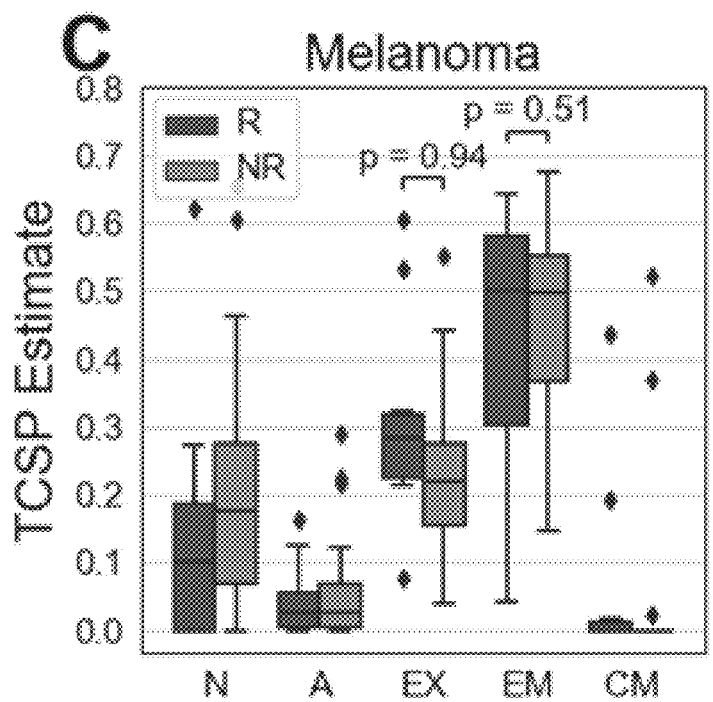
FIG. 18C shows T Cell state profiles of responders (R) and non-responder (NR) to anti-PD1 treatment in a cohort of patients with recurrent and metastatic Melanoma. The alternative hypothesis is that EX is lower and EM is higher in responders (R, n=10) vs non-responders (NR, n=21). Hypothesis was tested using the one-sided Mann-Whitney U test.

Last, we explored an existing public dataset of advanced Melanoma patients treated with Nivolumab (Riaz, Nadeem et al. Cell. 2017 Nov. 2; 171(4):934-949.e16). We investigated the TCSs in 31 on-treatment tumors. Patients who responded to Nivolumab were found to have higher levels of EX, EM, and total T cell infiltrate (FIG. 17G), echoing observations in HNSCC (FIG. 18A). However, no trends were observed when considering sum-normalized readouts (FIG. 18C). These observations agree with some previous studies, but not others. In line with the above HNSCC and NSCLC experimentation, we built a third multianalyte biomarker to predict response to Nivolumab. This biomarker also predicted objective response (AUC=0.69) and overall survival in this third indication (FIG. 17H and FIG. 17I).

Although varying across difference cancers, the TCSP of tumors is useful in predicting clinical outcomes to treatment with anti-PD-1 therapies. With its unique ability to characterize FFPE samples, TCSP can facilitate previously impossible translational research. To aid other researchers in characterizing the TCS of their cohorts and discovering other TCSP-based biomarkers, we have made TCSP available via tcsp.cofactorgenomics.com.

Example 9: T-Cell State Profiling Multiple Cancers

Figure 19:
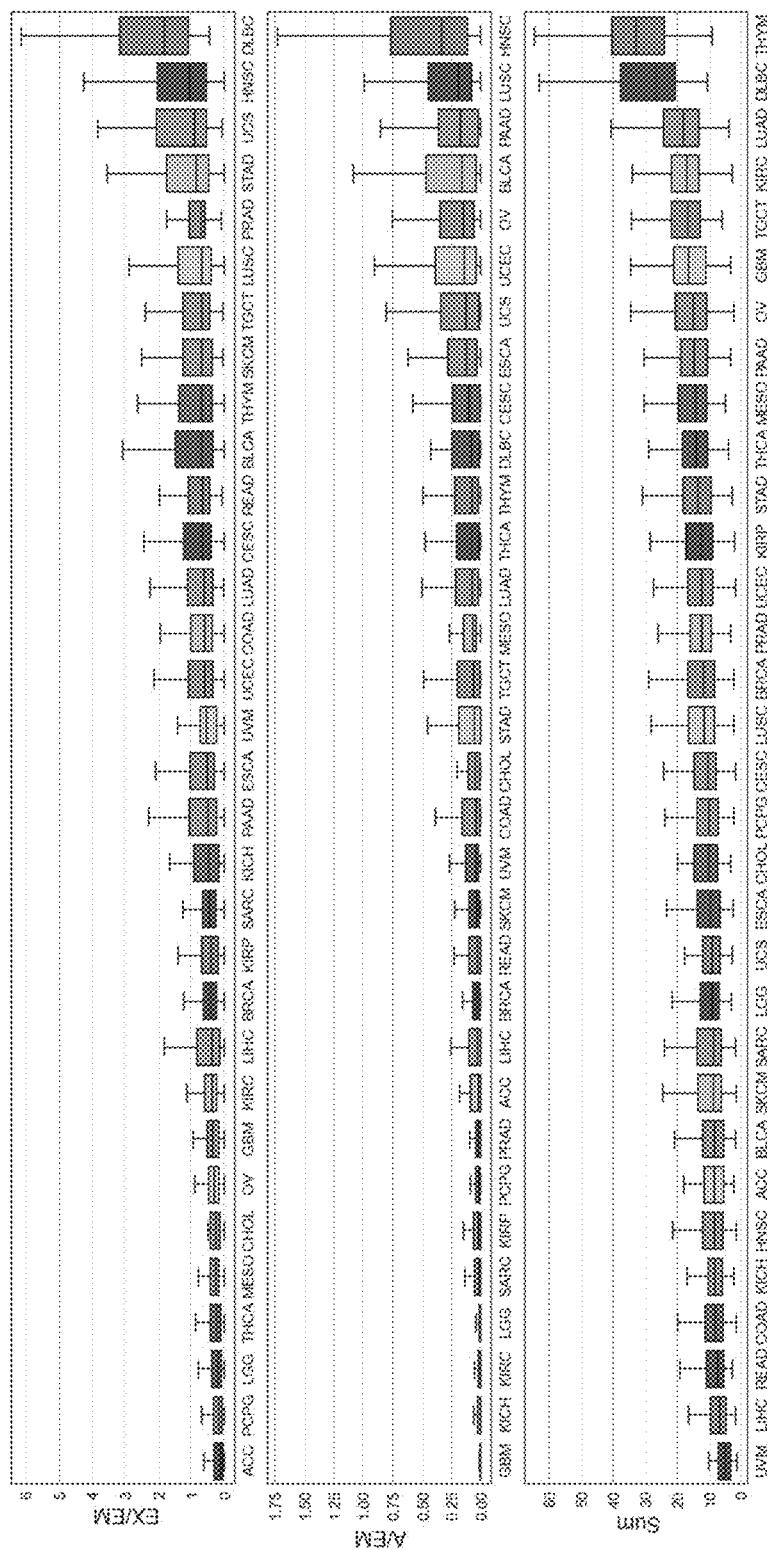
FIG. 19 shows T Cell state profiles of many cancers. Box and whisker plots show the inter- and intra-tumor variance of various TCGA projects for: the Effector Memory-normalized Exhaustion levels (EX/EM), and the Effector Memory-normalized Activation levels (A/EM), and the sum total infiltrate (Sum). Outliers are omitted for visual clarity.

Given the performance of TCSP-based biomarkers in HNSCC, NSCLC, and melanoma, we leveraged TCGA data to expand our investigation to 32 additional indications. To identify additional tumor types in which response to anti-PD-1 might be predicted, we searched for tumor types with similar characteristics to HNSCC, NSCLC, and melanoma. The HNSCC, NSCLC, and melanoma cohorts had a high ratio of Exhausted to EM cells (FIGS. 17A-I). As expected, in the TCGA data, Head and Neck Squamous Cell Cancer (HNSC), Lung Squamous Cell Cancer (LUSC), and Skin Cutaneous Melanoma (SKCM) %6 were among the eight highest EX/EM ratios (FIG. 19). Other indications with high EXEM ratio include Large B-cell Lymphoma (DLBC), Uterine Carcinosarcoma (UCS), and Stomach adenocarcinoma (STAD). HNSCC and LUSC are the two highest in the ratio of Activated to EM, followed by Pancreatic Adenocarcinoma (PAAD), Bladder Urothelial Carcinoma (BLCA), and Ovarian Serous Cystadenocarincoma (OV) (FIG. 19). These additional tumor types are potential candidates for TCSP-based biomarkers to predict anti-PD-1 response.

Figure 20:
FIG. 20 shows T Cell state profiles of many cancers. Box and whisker plots show the inter- and intra-tumor variance of various TCGA projects for the levels of Naïve (N), Activated (A), Exhausted (EX), Effector Memory (EM), and Central Memory (CM) T Cell States. Outliers are omitted for visual clarity.
Figure 21:
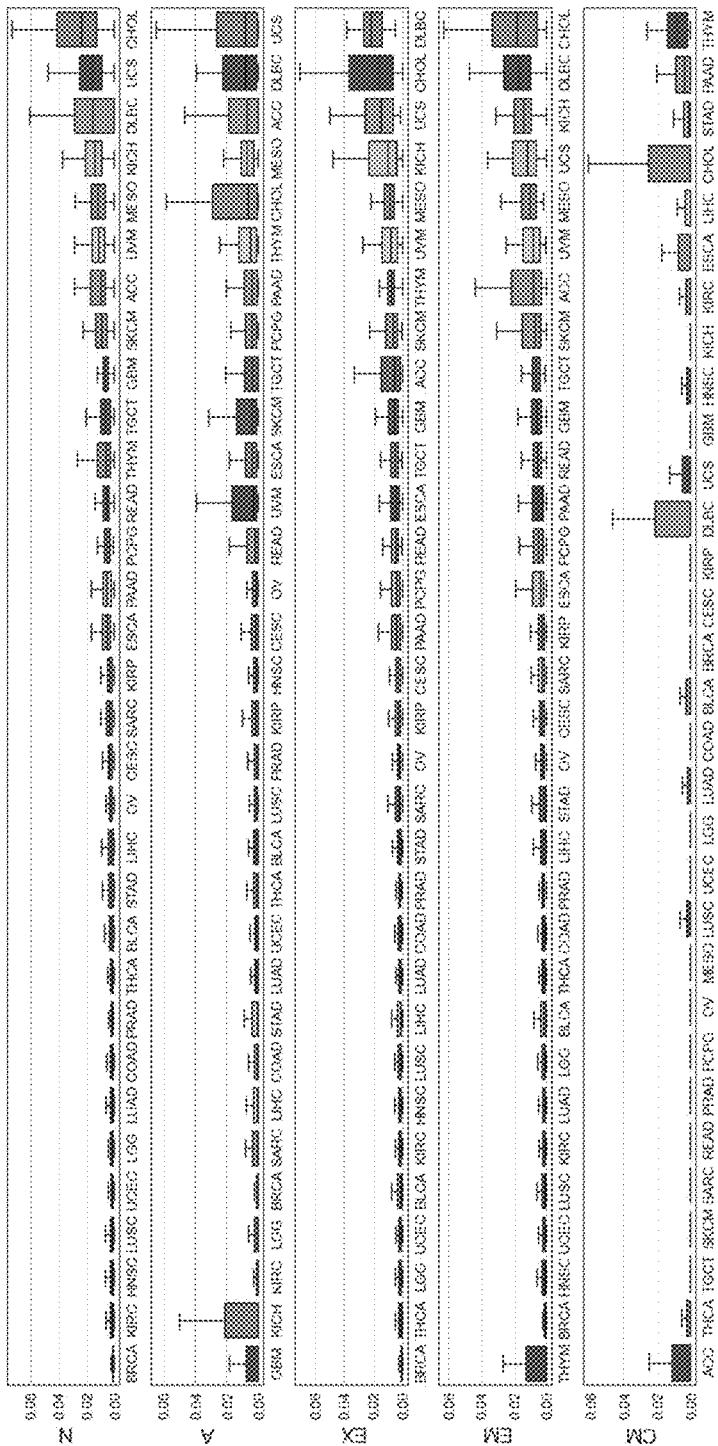
FIG. 21 shows normalized T Cell state profiles of many cancers. Box and whisker plots show the inter- and intra-tumor variance of various TCGA projects for the levels of sum-normalized T Cell States: Naïve (N), Activated (A), Exhausted (EX), Effector Memory (EM), and Central Memory (CM). Outliers are omitted for visual clarity.

We also investigated other general immunological trends across tumor types in TCGA. The inter-disease variance was as large as intra-disease variance (Supplementary FIG. 10) for many of the TCS readouts. Several observations fit expectations. Thymoma (THYM) and DLBC had the highest total infiltrate (FIG. 19), while Thyroid Carcinoma (THCA) had the highest presence of the Naïve T cells (FIG. 20). Almost all cancers lacked CM T cells, except THYM, which had the highest abundance (Supplementary FIG. 10). Other observations may provide new insights. UCS, DLBC, and Cholangiocarcinoma (CHOL) were the three highest exhausted diseases (FIG. 21). OV had the highest levels of Activated T Cells, while Glioblastoma Multiforme (GBM) had the highest abundance of EM T Cells (FIG. 20). To facilitate other researchers in exploring this characterization of TCGA, we have made the TCSP of TCGA samples available at tcsp.cofactorgenomics.com Example 10: Methods The following experimental protocols were used to generate the data described in Examples 5-9.

Isolation of T Cell Subsets by Flow Cytometry

Naïve T cells, effector memory T cells, and central memory T cells were isolated by FACS sorting. Cryopreserved human peripheral blood mononuclear cells (PBMCs) from normal healthy donors were obtained from StemExpress (Folsom, Calif.) and Astarte Biologics (Bothwell, Wash.). Cryopreserved CD4+ and CD8+ T cells, enriched by negative selection from PBMCs from normal healthy donors, were obtained from StemExpress. Cells were removed from liquid nitrogen storage and rapidly thawed in a 37° C. water bath with gentle hand shaking until only a small piece of ice remained. Cells were transferred to a 50 mL conical centrifuge tube. One mL of prewarmed media (RPMI-1640 (no phenol red) supplemented with 10% FBS, 10 mmol/L HEPES buffer, 1× GlutaMAX, 50 µg/mL gentamicin) was added dropwise to the cells. Fifteen mL prewarmed media was then slowly added. Cells were centrifuged at 200×g for 10 min at room temperature. The supernatant was aspirated, and cells were resuspended in FACS buffer (calcium- and magnesium-free Hank's balanced salt solution (HBSS) supplemented with 2% FBS). Seventy five µL aliquots of cell suspension (5 million cells) were transferred to tubes containing 25 µl T cell antibody panel (5 µl each of Brilliant Violet 421™ anti-human CD3 (clone UCHT1, BioLegend (San Diego, Calif.)), PerCP/Cyanine5.5 anti-human CD4 (clone SK3, BioLegend), APC-H7 anti-human CD8 (clone SKI, BD Biosciences (San Jose, Calif.)), PE anti-human CCR7 (clone G043H7, BioLegend), PE-Cy™ 7 anti-human CD45RA (clone L48, BD Biosciences), and incubated at 4° C. for 20 min. The cells were washed twice with 1 mL cold FACS buffer by centrifugation at 350×g, 5 min, 4° C. Pellets were each resuspended in 100 µL cold FACS buffer and then pooled. SYTOX™ Green dead cell stain (Thermo Fisher, Waltham, Mass.) was added to a final dilution of 1:1000. FACS sorting was performed using the BD Biosciences Aria Fusion at the Flow Cytometry Research Core Facility at Saint Louis University School of Medicine. Compensation was established using Anti-Mouse Ig, κ/Negative Control Compensation Particles Set (BD Biosciences) for conjugated antibodies, and PBMCs for SYTOX™ Green dead cell stain. Cells were sorted using a 70 µm nozzle into cold sort buffer (80% HBSS, 20% FBS). Gating for T cell subtypes was as follows: naïve CD4+ T cells (CD3+/CD4+/CD45RA+/CCR7+): naïve CD8+ T cells (CD3+/CD8+/CD45RA+/CCR7+); effector memory CD4+ T cells (CD3+/CD4+/CD45RA-/CCR7-); effector memory CD8+ T cells (CD3+/CD8+/CD45RA-/CCR7-); central memory CD4+ T cells (CD3+/CD4+/CD45RA-/CCR7+): central memory CD8+ T cells (CD3+/CD8+/CD45RA-/CCR7+); Sorted lymphocytes were centrifuged at 1000×g for 5 min and pellets lysed in 350 µL Buffer RLT Plus (Qiagen, Germantown, Md.) supplemented with 1/100th volume ß-mercaptoethanol. RNA was extracted using the RNeasy Plus Micro Kit (Qiagen, Germantown, Md.) according to the manufacturer's instructions, and used for RNA-seq library preparation and sequencing.

In Vitro T Cell Exhaustion

The in vitro generation of exhausted T cells was modified from Balkhi, et al. (ref.), and performed by STEMCELL Technologies (Vancouver, BC, Canada). Naïve CD8+ T cells were isolated from fresh leukapheresis samples from three normal healthy donors using the EasySep™ Human Naïve CD8+ T Cell Isolation Kit II (STEMCELL Technologies) following the manufacturer's recommended protocol. The isolated cells were resuspended in media (RPMI supplemented with 10% FBS) to a final concentration of $1.5-2\times10^6$ cells/mL. One hundred microliter aliquots of cell suspension ($1.5-2\times10^5$ cells) were transferred to 96-well U-bottom plates. Cultures were rested at 37° C., 5% CO2 for 30 minutes before the addition of tetrameric antibody complexes (ImmunoCult™ Human CD3/CD28/CD2 T Cell Activator, STEMCELL Technologies). A two-fold working stock of T Cell Activator was first prepared in media at a concentration of 50 µl/ml. One hundred microliters of working stock were then added to wells for a final concentration of 25 µl/ml. Cultures were incubated at 37° C., 5% CO2 for a total of 14 days with re-stimulation occurring every two days, as follows. Every two days (Day 2, 4, 6, 8, 10 and 12) average viable cell numbers were determined using the Cellometer Auto 2000 Cell Viability Counter (Nexcelom). Cells were pelleted by centrifugation, supernatants were removed and cells washed once with media before being resuspended in 200 µL media containing 25 µL/mL of the T Cell Activator. In each stimulation step, the number of viable cells was readjusted to the same number as originally seeded on Day 0 (1.5-2×105 cells/well depending on the donor). Likewise, at each timepoint, triplicate cell pellets were lysed with Buffer RLT Plus (Qiagen, Germantown. Md.) supplemented with $\frac{1}{100}^{th}$ volume ß-mercaptoethanol. RNA was then extracted using the RNeasy Plus Micro Kit (Qiagen) according to the manufacturer's instructions and used for RNA-seq library preparation and sequencing.

Cytokine Assays

At each 2 day timepoint of the in vitro generation of exhausted T cells, supernatants from triplicate wells were collected and stored at −80° C. for cytokine evaluation. Cytokine concentrations were measured using the Meso Scale Discovery (MSD®) multiplex immunoassay as follows. On the day of the assay, the V-Plex Custom Human Cytokine Proinflammatory Panel 1 (2-Plex) kit and the supernatant samples were brought to room temperature. The assay plates were washed three times with 150 µL of wash buffer (PBS supplemented with 0.05% Tween-20 (Sigma-Aldrich, Saint Louis, Mo.). Eight concentrations of the Calibrator Blend (standard) were prepared in Diluent 2 in microcentrifuge tubes, and 50 µL of each concentration of the Calibrator was added to each assay plate in duplicate. Next, 25 µL of Diluent 2 was added to the remaining wells of the assay plates. Supernatants were diluted 1:100 in PBS supplemented with 1% BSA (Sigma-Aldrich) and 25 µL of each sample (undiluted and 1:100) was added to the assay plates to yield final dilutions of 1:2 and 1:200. The assay plates were sealed with adhesive plate seals and incubated at room temperature on a plate shaker (650 rpm) for 2 hours. After the 2 hour incubation, the plates were washed three times with 150 µL of wash buffer. The detection antibody solution was prepared by combining 240 µL of each supplied detection antibody (IFN-γ and IL-2) with 11.52 mL of Diluent 3 and 25 µL of the detection antibody solution was then added to each well. The assay plates were sealed with adhesive plate seals and incubated at room temperature on a plate shaker (650 rpm) for 2 hours. After the 2 hour incubation, the plates were washed three times with 150 µL of 1× wash buffer and 150 µL of 2× Read Buffer T was then added to each well. The plates were read immediately on a Meso QuickPlex SQ 120 Instrument.

Flow Cytometric Analysis of T Cell Exhaustion Markers

At each 2 day timepoint of the in vitro generation of exhausted T cells, one sample from each was assessed for LAG3, Tim3 and PD-1 expression by flow cytometry. Cells were distributed into a %-well U-bottom plate for staining. Cells were first washed twice with FACS buffer followed by centrifugation at 1500 rpm for 5 minutes and removal of the supernatant. Human Fc block (BD Biosciences) was diluted in FACS buffer, and 50 µL of diluted Fc block was then added to each well (1 µg/sample), after which the cells were gently resuspended and incubated for 10 minutes at room temperature. Antibodies to surface markers CD8, LAG3, Tim3 and PD-1 were used to stain the cells to assess purity by flow cytometry. Working concentrations of the antibodies were prepared in FACS buffer (50 µL per staining point), and 50 µL of each diluted antibody mixture was added to the appropriate wells. For staining controls either previously stimulated and cryopreserved Concanavalin A (ConA) stimulated PBMCs were thawed and used, or extra ImmunoCult™ Human T Cell Activator stimulated cells from the study were used depending on the time point. After the appropriate antibody, or antibody mixture had been added to each well, cells were incubated at 4° C. in the dark for 30 minutes. At the end of the incubation period, cells were washed twice with FACS buffer, followed by centrifugation at 1500 rpm for 5 minutes and removal of the supernatant. Cells were then resuspended in 150 µL of FACS buffer followed by addition of the viability dye 7-AAD to the appropriate wells (2 µL/sample). Cells were analyzed by flow cytometry on a Beckman Coulter CytoFLEX Flow Cytometer, collecting 20,000-50,000 cell events (or a maximum of 60 seconds) per well for each sample. Antibodies were obtained from BioLegend (San Diego, Calif.): Brilliant Violet 421™ anti-human CD8, FITC anti-human LAG3, PE anti-human TIM3, APC anti-human PD-1.

RNA-Seq Library Preparation and Sequencing

Libraries were prepared using the TruSeq RNA Access Library Prep Kit from Illumina (San Diego, Calif.) according to the manufacturer's instructions (naïve, effector memory, central memory); or the NEBNext® Ultra™ II Directional RNA Library Prep Kit for Illumina® (NEB, Ipswich, Mass.) along with the xGen Exome Research Panel biotinylated oligonucleotide pool and xGen Hybridization and Wash Kit from Integrated DNA Technologies (Coralville, Iowa) according to the manufacturer's instructions (naïve, activated, exhausted, HNSCC and NSCLC FFPE specimens). Final libraries were sequenced as single-end 75 base pair reads on a NextSeq500 (Illumina, San Diego, Calif.) following the manufacturers protocols.

Dissociated Tumor Cells

Cryopreserved dissociated tumor cells from three indications (ovarian adenocarcinoma, lung adenocarcinoma, and melanoma) were obtained from Discovery Life Sciences (Huntsville, Ala.). Cells were processed and stained for FACS analysis and sorting as described above for cryopreserved PBMCs, except that prior to antibody staining Fc receptors were blocked using Human TruStain FcX™ according to manufacturer's instructions (BioLegend. San Diego, Calif.).

Processing of RNAseq Data

FASTQ files were preprocessed with trim_galore/cutadapt to remove adapter sequences as well as reads with PHRED quality scores less than 20 and reads that were shorter than 20 base pairs. The trimmed reads were aligned to the human genome GRCh38 with STAR using the 2-pass method. Read counts were generated using htseq-counts and annotation from Gencode v22.

T Cell State Model Creation

Differential expression of the five cell states was initially performed using DeSeq2. Eight, three, six, five, and three libraries were used for the naive, activated, exhausted, EM, CM states, respectively. For each state, genes were considered in descending order of log fold difference versus all other states. Genes with a coefficient of variation larger than 0.25 and a maximum counts per million (CPM) less than 15 were ignored until 10 genes were chosen. The mean CPM of respective libraries for these selected genes was used to create the preliminary model for each T cell state consisting of 123 genes. The genes in these models were then filtered using Cancer Cell Line Encyclopedia (CCLE). Cell lines with disease origins related to immune cells were not considered. Mean expression across all other cell lines was normalized per gene by the max value of the five T cell state models. Genes corresponding to a normalized, average CCLE expression>=0.2 were removed from the models. The final T cell state models were comprised of 46 genes. For select experiments, certain donors were omitted to remove bias, e.g. naive, activated, and exhausted libraries from one donor were removed to estimate those libraries during the performance evaluation of the models.

T Cell State Estimation

Estimation can be modelled as a linear combination of the gene expression of each cell type present in the bulk reduced capture RNA sequencing data: B=S×F, where B is a vector representing the gene expression of the 46 genes from a heterogenous sample comprised of tumor, stroma, and immune cells, S is a 46 by 5 matrix of T cell state models, and F is a vector of length 5 that represents the estimated mRNA fractions of each immune cell type present in the heterogenous sample. For every sample, S is known, B is sequenced, and T cell state profiling solves for F. CPMs of each gene of input samples were normalized to the max expression of the T cell state models. Then, linear epsilon Support Vector Regression was used to solve the above equation, yielding estimated mRNA fractions of the T cell states.

Data Creation and Access

Exhaustion titrations were created in silico by randomly selecting reads from CD45− libraries of 3 different tumors (Lung, Ovarian, Melanoma) and the day 14 library from donor 3. Mixes with ovarian CD45− libraries were created such that 0, 1, 2, 5, 8, 12, 17, 25, 50, 75, 100% of reads came from the exhausted library, while for mixes with lung and melanoma CD45− libraries, 0, 25, 50, 75, 100% of reads came from the exhausted library. Fastq files for CD39+ isolates (GSE113590), PD-1+ isolates (GSE99531), and Melanoma tumor (GSE91061) samples were downloaded from the European Nucleotide Archive (ENA) via the Aspera transfer tool. Head and Neck Squamous Cell Carcinoma (HNSCC), Cervical Squamous Cell Carcinoma (CESC), and Liver Hepatocellular Carcinoma (LIHC) counts files were downloaded via the GDC/TCGA REST API (api.gdc.cancer.gov). For these three datasets, virus status labels were used as published.

Specimens

HNSCC samples were collected from pre-immunotherapy tumor tissue obtained from patients with RM-HNSCC that were treated with a PD-1 inhibitor (pembrolizumab or nivolumab). Sequential sections of formalin-fixed and paraffin embedded (FFPE) tissue blocks were utilized for analysis via T cell state profiling and the on-label PD-L1 IHC assay. Patients were grouped according to tumor response to immunotherapy using RECIST criteria. The study design was approved by Washington University IRB.

NSCLC samples were collected at time of first diagnosis from patients before treatment with a PD-1 inhibitor (pembrolizumab or nivolumab) between April 2013 and January 2018 at the University Hospital Basel; the Cantonal Hospital Baselland, Switzerland; and the St Clara Hospital Basel. The groups of patients analyzed is a subset of a cohort previously published. PD-L1 IHC and TMB was performed and evaluated as previously described. The study was approved by the local Ethical Review Board (Ethikkommission Nordwestschweiz, Project-ID 2018-01751) and performed in compliance with all relevant ethical regulations.

Melanoma samples were a subset of a cohort previously published. Responders are defined as those with complete response and partial response and non-responders are defined as those with progressive disease according to RECIST criteria.

RNA was extracted from HNSCC FFPE samples using the RNAstorm™ Kit (Cell Data Sciences, Fremont, Calif.).

RNA was extracted from NSCLC FFPE samples using the RecoverAll™ Total Nucleic Acid Isolation Kit (Thermo Fisher Scientific, Waltham, Mass.).

TCSP-Based Biomarker Creation and Analysis

TCSP-based biomarkers were optimized independently for each of the three indications via cross validation. Input features were normalized and/or non-normalized TCSP readouts from optimized TCS models. After feature standardization, several feature projection (Principal Component Analysis, Independent Component Analysis, Kernel Principal Component Analysis) and machine learning algorithms (Adaboost, K-Nearest Neighbors, Random Forest, Support Vector Machine) were evaluated via cross validation. The machine learning (ML) model with the highest cross validated Area Under the Receiver Operating Characteristic curve (AUC) was chosen as the biomarker. Bootstrap sampling was used to cross validate and approximate ML model performance for future independent datasets. In bootstrap sampling, a set of samples are randomly sampled with replacement for training the ML model, with the remaining samples—called the out-of-bag set—used to evaluate the ML model's performance. This is done iteratively (hundreds of times) and a model's performance is evaluated by averaging the performance over all out-of-bag samples. Bootstrap sampling is the most rigorous statistical approach to predicting performance of a ML model in future prospective cohorts. Receiver Operating Characteristic (ROC) curves are used to show overall performance of TCSP-based biomarkers in predicting objective response. The curves shown for TCSP-based biomarkers are the mean out-of-bag ROC of the optimal ML model. PD-L1 IHC and TMB ROC curves include all samples without any sampling procedure. Kaplan-Meier plots are used to show the ability for the same TCSP-based biomarkers to predict overall survival. To do so, the average out-of-bag prediction scores of all samples was thresholded at 0.5 to determine if a sample was biomarker positive or negative. All ML model optimization and evaluation was performed with Python (3.8.3) via the Scipy library (1.5.0).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Numbered Embodiments

The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed.

1. A method of optimizing an immunotherapy regimen, the method comprising: (a) obtaining RNA sequencing data from a sample obtained from a subject being treated with an immunotherapy regimen; (b) applying a deconvolution algorithm to at least a subset of the RNA sequencing data to identify and quantify an amount or percentage of exhausted T-cells in the sample based on expression levels of one or more cell status signature genes; (c) determining if the sample displays an elevated level of exhausted T-cells; and (i) recommending an alternative therapy based on a determination that the sample has an elevated level of exhausted T-cells in (c); or (ii) recommending continuing with the immunotherapy regimen based on a determination that the sample does not have an elevated level of exhausted T-cells. 2. The method of embodiment 1, wherein the immunotherapy regimen comprises an immune cell therapy, a cancer vaccine, a cytokine therapy, an antibody therapy, or any combination thereof 3. The method of embodiment 2, wherein the antibody therapy comprises tumor targeting monoclonal antibodies, immune cell activating antibodies, or a combination thereof 4. The method of embodiment 2 or 3, wherein the immune cell therapy comprises chimeric antigen receptor T-cell (CAR-T) therapy. 5. The method of any one of the preceding embodiments, wherein the immunotherapy regimen comprises an active immunotherapy, a passive immunotherapy, or a combination thereof. 6. The method of any one of the preceding embodiments, wherein the elevated level of exhausted T-cells is at least 50% of the T-cells of the sample. 7. The method of any one of the preceding embodiments, wherein the elevated level of exhausted T-cells indicates the subject will not respond to the immunotherapy regimen. 8. Th method of any one of the preceding embodiments, wherein the elevated level of exhausted T-cells indicates the subject is not responding to the immunotherapy regimen. 9. The method of any one of the preceding embodiments, wherein the elevated level of exhausted T-cells indicates the immunotherapy regimen is ineffective. 10. The method of any one of the preceding embodiments, wherein the elevated level of exhausted T-cells indicates the immunotherapy regimen has lost efficacy. 11. The method of any one of the preceding embodiments, wherein applying the deconvolution algorithm further identifies or quantifies an amount or percentage of activated T-cells in the sample. 12. The method of embodiment 11, further comprising recommending the alternative therapy if the sample displays a low level of activated T-cells. 13. The method of embodiment 12, wherein the low level of activated T-cells comprises 20% or less of the T-cells of the sample. 14. The method of any one of the preceding embodiments, wherein the alternative therapy comprises chemotherapy, radiation therapy, surgery, or any combination thereof. 15. The method of any one of the preceding embodiments, wherein the alternative therapy is an additional immunotherapy. 16. The method of any one of embodiments 1-14, wherein the alternative therapy is a non-immunotherapy. 17. The method of any one of the preceding embodiments, wherein the T-cells comprise CD4+ cells, CD8+ cells, Natural Killer T-Cells (NKT), or any combination thereof. 18. The method of any one of the preceding embodiments, wherein the one or more cell status signature genes comprise one or more genes selected from Table 1. 19. The method of any one of the preceding embodiments, wherein the deconvolution algorithm applies a deconvolution matrix to the RNA sequencing data to quantify the T-cells having a particular status. 20. The method of embodiment 19, wherein the deconvolution matrix comprises a plurality of cell status signature genes. 21. The method of embodiment any one of the preceding embodiments, wherein the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. 22. The method of any one of the preceding embodiments, wherein the one or more cell status signature genes comprises at least 100 cell status signature genes. 23. The method of any one of the preceding embodiments, wherein the one or more cell status signature genes comprises at least 10 cell status signature genes. 24. The method of any one of the preceding embodiments, wherein the one or more exhaustion status signature genes have a bimodal expression signature between at least two different cell statuses with no more than a 50% overlap between modes. 25. The method of any one of the preceding embodiments, wherein the deconvolution algorithm requires no more than 100 cell status signature genes to identify and quantify the amount or percentage of T-cells in the sample having a particular status with a 90% accuracy for 100 independent samples. 26. The method of any one of the preceding embodiments, wherein (a) comprises obtaining RNA molecules from the sample and measuring the level of gene expression on the RNA molecules. 27. The method of any one of the preceding embodiments, wherein (a) comprises obtaining RNA molecules from the sample and performing reverse transcription polymerase chain reaction on the RNA molecules to generate complementary deoxyribonucleic acid (cDNA) molecules, and sequencing the cDNA molecules. 28. The method of embodiment 27, wherein the cDNA molecules are tagged with unique molecular identifiers and amplified by polymerase chain reaction prior to sequencing. 29. The method of any one of the preceding embodiments, wherein (a) comprises performing next generation RNA sequencing on a cDNA library generated from the sample. 30. The method of any one of the preceding embodiments, wherein the sample is a tumor biopsy. 31. The method of any one of the preceding embodiments, wherein the sample is at least one formalin-fixed paraffin-embedded (FFPE) curl. 32. The method of any one of the preceding embodiments, wherein the sample has an RNA integrity number (RIN) of no more than 6.0. 33. The method of any one of the preceding embodiments, wherein the sample has an RNA integrity number (RIN) of no more than 2.0. 34. The method of any one of the preceding embodiments, wherein the sample comprises RNA molecules at least 200 nucleotides in size that constitute no more than 90% of total RNA in the sample. 35. The method of any one of the preceding embodiments, wherein the sample comprises RNA molecules at least 200 nucleotides in size that constitute no more than 60% of total RNA in the sample. 36. The method of any one of the preceding embodiments, wherein the sample comprises RNA molecules at least 200 nucleotides in size that constitute no more than 30% of total RNA in the sample. 37. The method of any one of the preceding embodiments, wherein the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. 38. The method of any one of the preceding embodiments, wherein the subject has cancer. 39. The method of any one of the preceding embodiments, wherein the immunotherapy regimen is a cancer vaccine, cytokine therapy, immune cell therapy, antibody therapy, or a combination thereof. 40. The method of any one of the preceding embodiments, wherein the immunotherapy regimen is chimeric antigen receptor T-cell (CAR-T) therapy. 41. The method of any one of the preceding embodiments, further comprising the step of determining or predicting the effectiveness of the immunotherapy regimen based on the identification and quantification of the amount or percentage of T-cells having an exhausted status. 42. The method of embodiment 41, wherein determining or predicting the effectiveness of the immunotherapy regimen comprises determining a ratio of activated:exhausted T-cells in the sample. 43. The method of any one of the preceding embodiments, further comprising the step of applying a second deconvolution algorithm to at least a second subset of the RNA sequencing data to identify and quantify one or more T-cell subtypes that are present in the sample based on expression levels of one or more expression signature genes. 44. The method of any one of the preceding embodiments, further comprising analyzing at least a subset of the RNA sequencing data to determine level of gene expression for at least one immune modulatory gene.

45. A method for treating a subject, the method comprising: (a) administering an immunotherapy regimen to a subject in need thereof; (b) obtaining a sample from the subject; (c) sending the sample for analysis of cell status, wherein the analysis of cell status comprises: (i) generating RNA sequencing data from the sample; and (ii) applying a deconvolution algorithm to at least a subset of the RNA sequencing data to identify and quantify an amount or percentage of cells in the sample having one or more cell statuses based on expression levels of one or more cell status signature genes; and (d) determining if the immunotherapy regimen is effective based on the identity and quantity of the one or more cell statuses. 46. The method of embodiment 45, wherein analysis of cell status measures the status of at least one immune cell type. 47. The method of embodiment 46, wherein the at least one immune cell type is selected from T-cells, natural killer (NK) cells, B-cells, macrophages, and plasma cells. 48. The method of embodiment 46, wherein the at least one immune cell type is selected from the group consisting of CD4+ memory T-cells, CD4+ naive T-cells, CD4+ T-cells, central memory T (Tcm) cells, effector memory T (Tem) cells, CD4+ Tcm, CD4+ Tem, CD8+ T-cells, CD8+ naive T-cells, CD8+ Tcm, CD8+ Tem, regulatory T cells (Tregs), T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, and plasma cells. 49. The method of embodiment 46, wherein the at least one immune cell type is selected from the group consisting of M1 macrophages, M2 macrophages, CD19+ B cells, CD14+ monocytes, CD56+ NK cells, CD8+ T cells, Treg cells, and CD4+ T cells. 50. The method of embodiment 46, wherein the at least one immune cell type comprises T-cells. 51. The method of embodiment 50, wherein the T-cells comprise CD8+ cells, CD4+ cells, or a combination thereof 52. The method of any one of embodiments 45-51, wherein the one or more cell statuses comprises naïve status, activated status, activation recovered status, terminally exhausted status, progenitor exhausted stats, central memory status, effector memory status, stem cell memory status or any combination thereof. 53. The method of any one of embodiments 45-52, wherein the one or more cell statuses comprises exhausted status. 54. The method of any one of embodiments 45-53, wherein the immunotherapy regimen comprises an immune cell therapy, a cancer vaccine, a cytokine therapy, an antibody therapy, or any combination thereof. 55. The method of any one of embodiments 45-54, wherein the antibody therapy comprises tumor targeting monoclonal antibodies, immune cell activating antibodies, or a combination thereof. 56. The method of any one of embodiments 45-55, wherein the immune cell therapy comprises chimeric antigen receptor T-cell (CAR-T) therapy. 57. The method of any one of embodiments 45-56, wherein the immunotherapy regimen comprises an active immunotherapy, a passive immunotherapy, or a combination thereof. 58. The method of any one of embodiments 45-57, wherein determining if the immunotherapy regimen is effective based on the identity and quantity of the one or more cell statuses comprises comparing the quantity of cells having a particular cell status to a predetermined threshold for the particular cell status. 59. The method of embodiment 58, wherein the particular cell status is exhaustion. 60. The method of embodiment 58 or 59, wherein the predetermined threshold is at least 50% of the cells. 61. The method of any one of embodiments 45-60, further comprising (e) administering an alternative therapy if the immunotherapy is determined to be ineffective. 62. The method of embodiment 61, wherein the alternative therapy comprises chemotherapy, radiation therapy, surgery, or any combination thereof. 63. The method of embodiment 61, wherein the alternative therapy is an additional immunotherapy. 64. The method of embodiment 61, wherein the alternative therapy is a non-immunotherapy. 65. The method of any one of embodiments 45-64, wherein the one or more cell status signature genes comprise one or more genes selected from Table 1. 66. The method of any one of embodiments 45-65, wherein the deconvolution algorithm applies a deconvolution matrix to the RNA sequencing data to quantify the T-cells having a particular status. 67. The method of embodiment 66, wherein the deconvolution matrix comprises a plurality of cell status signature genes. 68. The method of any one of embodiments 45-67, wherein the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. 69. The method of any one of embodiments 45-68, wherein the one or more cell status signature genes comprises at least 100 cell status signature genes. 70. The method of any one of embodiments 45-69, wherein the one or more cell status signature genes comprises at least 10 cell status signature genes. 71. The method of any one of embodiments 45-70, wherein the one or more cell status signature genes have a bimodal expression signature between at least two different cell statuses with no more than a 50% overlap between modes. 72. The method of any one of embodiments 45-71, wherein the deconvolution algorithm requires no more than 100 cell status signature genes to identify and quantify the amount or percentage of T-cells in the sample having a particular status with a 90% accuracy for 100 independent samples. 73. The method of any one of embodiments 45-72, wherein (i) comprises obtaining RNA molecules from the sample and measuring the level of gene expression on the RNA molecules. 74. The method of any one of embodiments 45-73, wherein (i) comprises obtaining RNA molecules from the sample and performing reverse transcription polymerase chain reaction on the RNA molecules to generate complementary deoxyribonucleic acid (cDNA) molecules, and sequencing the cDNA molecules. 75. The method of embodiment 74, wherein the cDNA molecules are tagged with unique molecular identifiers and amplified by polymerase chain reaction prior to sequencing. 76. The method of any one of embodiments 45-75, wherein (i) comprises performing next generation RNA sequencing on a cDNA library generated from the sample. 77. The method of any one of embodiments 45-76, wherein the sample is a tumor biopsy. 78. The method of any one of embodiments 45-77, wherein the sample is at least one formalin-fixed paraffin-embedded (FFPE) curl. 79. The method of any one of embodiments 45-78, wherein the sample has an RNA integrity number (RIN) of no more than 6.0. 80. The method of any one of embodiments 45-79, wherein the sample has an RNA integrity number (RIN) of no more than 2.0. 81. The method of any one of embodiments 45-80, wherein the sample comprises RNA molecules at least 200 nucleotides in size that constitute no more than 90% of total RNA in the sample. 82. The method of any one of embodiments 45-81, wherein the sample comprises RNA molecules at least 200 nucleotides in size that constitute no more than 60% of total RNA in the sample. 83. The method of any one of embodiments 45-82, wherein the sample comprises RNA molecules at least 200 nucleotides in size that constitute no more than 30% of total RNA in the sample. 84. The method of any one of embodiments 45-83, wherein the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. 85. The method of any one of embodiments 45-84, wherein the subject has cancer. 86. The method of any one of embodiments 45-85, wherein the analysis of cell status further comprises the step of applying a second deconvolution algorithm to at least a second subset of the RNA sequencing data to identify and quantify one or more T-cell subtypes that are present in the sample based on expression levels of one or more expression signature genes. 87. The method of any one of embodiments 45-86, wherein the analysis of cell status further comprises the step of comprising analyzing at least a subset of the RNA sequencing data to determine level of gene expression for at least one immune modulatory gene.

88. A method of preparing an immune cell therapy, the method comprising: (a) obtaining immune cells derived from a subject in need immune cell therapy; (b) assessing the status of the immune cells by: (i) generating RNA sequencing data from a subset of the immune cells; and (ii) applying a deconvolution algorithm to at least a subset of the RNA sequencing data to identify and quantify an amount or percentage of immune cells in the sample having at least one particular status based on expression levels of one or more cell status signature genes; and (c) activating the immune cells to target cancerous tissue in the subject. 89. The method of embodiment 88, wherein step (b) is performed multiple times. 90. The method of embodiment 88, wherein step (b) is performed at a plurality of time points in the process. 91. The method of any one of embodiments 88-90, wherein step (b) is performed at least prior to activating the immune cells. 92. The method of any one of embodiments 88-91, wherein step (b) is performed at least once after activating the immune cells. 93. The method of any one of embodiments 88-92, wherein step (b) is performed multiple times after activating the immune cells. 94. The method of any one of embodiments 88-93, wherein the at least one particular status comprises naïve status, activated status, activation recovered status, terminally exhausted status, progenitor exhausted status, central memory status, effector memory status, stem cell memory status or any combination thereof. 95. The method of any one of embodiments 88-94, further comprising predicting the efficacy of the immune cell therapy based on the identity and quantity of immune cells having at least one particular status. 96. The method of embodiment 95, wherein predicting the efficacy of the immune cell therapy comprises comparing the identity and quantity of immune cells having at least one particular status to a reference. 97. The method of embodiment 96, wherein the at least one particular status compared to the reference comprises an exhaustion status. 98. The method of embodiment % or 97, wherein the at least one particular status compared to the reference comprises an activated status. 99. The method of any one of embodiments 96-98, wherein the at least one particular status compared to the reference comprises a naïve status. 100. The method of any one of embodiments 96-99, wherein the efficacy is predicted based on the identity and quantity of immune cells having a particular status prior to activating the immune cells. 101. The method of any one of embodiments 96-99, wherein the efficacy is predicted based on the identity and quantity of immune cells having a particular status after activation. 102. The method of any one of embodiments 88-101, wherein the immune cells comprise T-cells, natural killer (NK) cells, B-cells, macrophages, plasma cells, or any combination thereof. 103. The method of any one of embodiments 88-102, wherein the immune cells comprise CD4+ memory T-cells, CD4+ naive T-cells. CD4+ T-cells, central memory T (Tcm) cells, effector memory T (Tem) cells, CD4+ Tcm. CD4+ Tem, CD8+ T-cells, CD8+ naive T-cells, CD8+ Tcm, CD8+ Tem, regulatory T cells (Tregs). T helper (Th) 1 cells, Th2 cells, gamma delta T (Tgd) cells, natural killer (NK) cells, natural killer T (NKT) cells, B-cells, naive B-cells, memory B-cells, class-switched memory B-cells, pro B-cells, plasma cells, or any combination thereof. 104. The method of any one of embodiments 88-103, wherein the immune cells comprise M1 macrophages, M2 macrophages, CD19+ B cells, CD14+ monocytes, CD56+ NK cells, CD8+ T cells, Treg cells, CD4+ T cells, or any combination thereof. 105. The method of any one of embodiments 88-104, wherein the immune cells comprise CD8+ cells, CD4+ cells, or a combination thereof. 106. The method of any one of embodiments 88-105, wherein the immune cell therapy is chimeric antigen receptor T-cell (CAR-T) therapy, tumor-infiltrating lymphocyte (TIL) therapy, engineered T-cell receptor (TCR) therapy, or natural killer (NK) cell therapy. 107. The method of any one of embodiments 88-106, wherein the immune cell therapy is CAR-T therapy. 108. The method of embodiment 107, wherein the CAR-T therapy is a CD9-targeting CAR-T cell therapy. 109. The method of embodiment 107 or 108, wherein the CAR-T therapy is axicabtagene ciloleucel or tisagenlecleucel. 110. The method of any one of embodiments 88-109, wherein activating the immune cells comprises, inserting a chimeric antigen receptor gene into the immune cells. 111. The method of any one of embodiments 88-110, wherein activating the immune cells comprises inserting an engineered T-cell receptor gene into the immune cells. 112. The method of any one of embodiments 88-111, wherein activating the immune cells comprises incubating the immune cells with a tumor cell antigen. 113. The method of any one of embodiments 88-112, further comprising proliferating the immune cells. 114. The method of any one of embodiments 88-113, further comprising identifying an optimal dosing status of the immune cells. 115. The method of embodiment 114, wherein the optimal dosing status is determined by comparing the amount or percentage of immune cells in the sample having at least one particular status to a reference. 116. The method of any one of embodiments 88-115, further comprising administering the immune cells to the subject. 117. The method of any one of embodiments 88-116, wherein the one or more cell status signature genes comprise one or more genes selected from Table 1. 118. The method of any one of embodiments 88-117, wherein the deconvolution algorithm applies a deconvolution matrix to the RNA sequencing data to quantify the immune cells having a particular status. 119. The method of embodiment 118, wherein the deconvolution matrix comprises a plurality of cell status signature genes. 120. The method of any one of embodiments 88-119, wherein the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. 121. The method of any one of embodiments 88-120, wherein the one or more cell status signature genes comprises at least 100 exhaustion status signature genes. 122. The method of any one of embodiments 88-121, wherein the one or more cell status signature genes comprises at least 10 exhaustion status signature genes. 123. The method of any one of embodiments 88-122, wherein the one or more exhaustion status signature genes have a bimodal expression signature between at least two different cell statuses with no more than a 50% overlap between modes. 124. The method of any one of embodiments 88-123, wherein the deconvolution algorithm requires no more than 100 cell status signature genes to identify and quantify the amount or percentage of T-cells in the sample having a particular status with a 90% accuracy for 100 independent samples. 125. The method of any one of embodiments 88-124, wherein (i) comprises obtaining RNA molecules from the sample and measuring the level of gene expression on the RNA molecules. 126. The method of any one of embodiments 88-125, wherein (i) comprises obtaining RNA molecules from the sample and performing reverse transcription polymerase chain reaction on the RNA molecules to generate complementary deoxyribonucleic acid (cDNA) molecules, and sequencing the cDNA molecules. 127. The method of any one of embodiments 88-126, wherein the cDNA molecules are tagged with unique molecular identifiers and amplified by polymerase chain reaction prior to sequencing. 128. The method of any one of embodiments 88-127, wherein (a) comprises performing next generation RNA sequencing on a cDNA library generated from the sample. 129. The method of any one of embodiments 88-128, wherein the sample is a tumor biopsy. 130. The method of any one of embodiments 88-129, wherein the sample is at least one formalin-fixed paraffin-embedded (FFPE) curl. 131. The method of any one of embodiments 88-130, wherein the sample has an RNA integrity number (RIN) of no more than 6.0. 132. The method of any one of embodiments 88-131, wherein the sample has an RNA integrity number (RIN) of no more than 2.0. 133. The method of any one of embodiments 88-132, wherein the sample comprises RNA molecules at least 200 nucleotides in size that constitute no more than 90% of total RNA in the sample. 134. The method of any one of embodiments 88-133, wherein the sample comprises RNA molecules at least 200 nucleotides in size that constitute no more than 60% of total RNA in the sample. 135. The method of any one of embodiments 88-134, wherein the sample comprises RNA molecules at least 200 nucleotides in size that constitute no more than 30% of total RNA in the sample. 136. The method of any one of embodiments 88-135, wherein the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. 137. The method of any one of embodiments 88-136, wherein the subject has cancer.

138. A method for processing data to determine cellular status, the method comprising: (a) obtaining RNA sequencing data from a sample obtained from a subject; (b) applying a deconvolution algorithm to at least a subset of the RNA sequencing data to identify and quantify an amount or percentage of T-cells in the sample having a particular status based on expression levels of one or more cell status signature genes. 139. The method of embodiment 138, wherein the particular status of the T-cells comprises naïve status, activated status, activation recovered status, terminally exhausted status, progenitor exhausted status, central memory status, effector memory status, stem cell memory status, or any combination thereof. 140. The method of embodiment 138 or 139, wherein the T-cells comprise CD4+ cells, CD8+ cells, Natural Killer T-Cells (NKT), or any combination thereof. 141. The method of any one of embodiments 138-140, wherein the one or more cell status signature genes comprise one or more genes selected from Table 1. 142. The method of any one of embodiments 138-141, wherein the deconvolution algorithm applies a deconvolution matrix to the RNA sequencing data to quantify the T-cells having a particular status. 143. The method of embodiment 142, wherein the deconvolution matrix comprises a plurality of cell status signature genes. 144. The method of any one of embodiments 138-143, wherein the deconvolution algorithm identifies and quantifies the one or more cell types that are present in the sample using linear least-squares regression (LLSR) quadratic programming (QP), perturbation model for gene expression deconvolution (PERT), robust linear regression (RLR), microarray microdissection with analysis of differences (MMAD), digital sorting algorithm (DSA), or support vector regression. 145. The method of any one of embodiments 138-144, wherein the one or more cell status signature genes comprises at least 100 cell status signature genes. 146. The method of any one of embodiments 138-145, wherein the one or more cell status signature genes comprises at least 10 cell status signature genes. 147. The method of any one of embodiments 138-146, wherein the one or more cell status signature genes have a bimodal expression signature between at least two different cell statuses with no more than a 50% overlap between modes. 148. The method of any one of embodiments 138-147, wherein the deconvolution algorithm requires no more than 100 cell status signature genes to identify and quantify the amount or percentage of T-cells in the sample having a particular status with a 9)% accuracy for 100 independent samples. 149. The method of any one of embodiments 138-148, wherein (a) comprises obtaining RNA molecules from the sample and measuring the level of gene expression on the RNA molecules. 150. The method of any one of embodiments 138-149, wherein (a) comprises obtaining RNA molecules from the sample and performing reverse transcription polymerase chain reaction on the RNA molecules to generate complementary deoxyribonucleic acid (cDNA) molecules, and sequencing the cDNA molecules. 151. The method of embodiment 150, wherein the cDNA molecules are tagged with unique molecular identifiers and amplified by polymerase chain reaction prior to sequencing. 152. The method of any one of embodiments 138-151, wherein (a) comprises performing next generation RNA sequencing on a cDNA library generated from the sample. 153. The method of any one of embodiments 138-152, wherein the sample is a tumor biopsy. 154. The method of any one of embodiments 138-153, wherein the sample is at least one formalin-fixed paraffin-embedded (FFPE) curl. 155. The method of any one of embodiments 138-154, wherein the sample has an RNA integrity number (RIN) of no more than 6.0. 156. The method of any one of embodiments 138-155, wherein the sample has an RNA integrity number (RIN) of no more than 2.0. 157. The method of any one of embodiments 138-156, wherein the sample comprises RNA molecules at least 200 nucleotides in size that constitute no more than 90% of total RNA in the sample. 158. The method of any one of embodiments 138-157, wherein the sample comprises RNA molecules at least 200 nucleotides in size that constitute no more than 60% of total RNA in the sample. 159. The method of any one of embodiments 138-158, wherein the sample comprises RNA molecules at least 200 nucleotides in size that constitute no more than 30% of total RNA in the sample. 160. The method of any one of embodiments 138-159, wherein the sample is obtained from skin, blood, brain, bladder, bone, bone marrow, breast, colon, stomach, esophagus, ovary, uterus, gallbladder, fallopian tube, testicle, kidney, liver, pancreas, adrenal gland, cervix, endometrium, head or neck, lung, prostate, thymus, thyroid, lymph node, or urinary bladder. 161. The method of any one of embodiments 138-160, wherein the subject has cancer. 162. The method of any one of embodiments 138-161, wherein the subject has received an immunotherapy regimen. 163. The method of embodiment 162, wherein the immunotherapy regimen is a cancer vaccine, cytokine therapy, immune cell therapy, antibody therapy, or a combination thereof. 164. The method of embodiment 162 or 163, wherein the immunotherapy regimen is chimeric antigen receptor T-cell (CAR-T) therapy. 165. The method of any one of embodiments 162-164, further comprising the step of determining or predicting the effectiveness of the immunotherapy regimen based on the identification and quantification of the amount or percentage of T-cells having a particular status. 166. The method of embodiment 165, wherein determining or predicting the effectiveness of the immunotherapy regimen comprises determining a ratio of activated:exhausted T-cells in the sample. 167. The method of embodiment 165, wherein the immunotherapy regiment is determined or predicted to be effective if at most 10% of T-cells in the sample are exhausted. 168. The method of any one of embodiments 138-167, further comprising the step of applying a second deconvolution algorithm to at least a second subset of the RNA sequencing data to identify and quantify one or more T-cell subtypes that are present in the sample based on expression levels of one or more expression signature genes. 169. The method of any one of embodiments 138-168, further comprising the step of analyzing at least a subset of the RNA sequencing data to determine level of gene expression for at least one immune modulatory gene.

What is claimed is:
1. A method comprising:
(a) obtaining ribonucleic acid (RNA) sequencing data from a tumor tissue sample obtained from a subject, the RNA sequencing data comprising expression levels of one or more genes associated with T-cell status; and
(b) applying a deconvolution algorithm to at least a subset of the RNA sequencing data to identify and quantify an amount or percentage of T-cells in the tumor tissue sample having a particular status based on the expression levels of one or more genes associated with T-cell status, wherein the particular status of the T-cells comprises naive status, activated status, activation recovered status, terminally exhausted status, progenitor exhausted status, central memory status, effector memory status, stem cell memory status, or any combination thereof,
(c) determining that the subject will be responsive to an immunotherapy regimen based at least on the amount or percentage of T-cells in the tumor tissue having the particular status based on the expression levels of the one or more genes associated with T-cell status, and
(d) administering the immunotherapy regimen to the subject, wherein the immunotherapy regimen is administered to the subject based at least on the amount or percentage of T-cells in the tumor tissue sample having the particular status, wherein the immunotherapy regimen comprises an immune checkpoint inhibitor that is an antibody or antigen binding fragment that binds an immune checkpoint target of a target cell of the subject.

2. The method of claim 1, wherein the T-cells comprise CD4+ cells, CD8+ cells, Natural Killer T-Cells (NKT), or any combination thereof.

3. The method of claim 1, wherein the one or more genes associated with T-cell status comprise at least one gene selected from the group consisting of CFH, BAIAP3, MMP25, TENM1, PLEKHB1, MCM10, RASGRP2, PTPN3, TRIB2, ACTN1, ADD2, CST7, TP73, BIRC5, ITGA6, PCSK5, CACNA1I, CSF2RB, ASB2, DOK5, VSIG1, SYP, CTSH, TNFRSF10A, EBI3, CD79A, AEBP1, ACTA2, IL2, IL23A, IFNG, SASH1, ARFGEF3, SLC16A10, KIF20A, STC2, VIPR1, IGFBP2, EPHA4, CAMSAP2, NRP2, DUSP1, LY9, MT1G, PKMYT1, LIF, RAP1GAP2, ARHGEF11, CABLES1, KLRD1, PRR5L, SYTL2, CYP1B1, MYOF, CEP55, USO1, LPAR6, MYO1F, CDC42BPA, EPHA1, CHMP7, NTRK2, CRIM1, NR3C2, JAKMIP1, NR4A2, AK5, GPR15, PPP2R2B, KIT, DGKI, AUTS2, B4GALT5, ACE, CCR5, PLXDC1, ZG16B, AK4, NFIA, ATF3, CCDC141, CDC25A, ITGA2, CSF2, TMEM200A, AQP3, MELK, RRAD, C15orf48, TTC16, LAIR2, ANGPTL4, IL7R, NSG1, PTK2, ITGAM, NPAS2, CAVIN3, C3AR1, MAL, RAB37, NBEA, CD248, ZDHHC14, ZBED2, MAF, FUT7, FCRL6, AMIGO1, ANXA2, DENND5A, DUSP8, MYBL1, KIF18B, BCL2L15, NUGGC, PLXNB2, MAML3, RASGEF1A, CR1, TCEA3, SMIM26, HIST2H4B, CCL5, HNF1B, AMY2B, ATP8B4, C17orf107, C1orf228, CCDC65, CCR2, CFP, GCNT4, GP5, LAG3, LEF1, TBX21, and ZBTB32.

4. The method of claim 3, wherein the one or more genes associated with T-cell status comprise at least one gene selected from the group consisting of MMP25, EBI3, LEF1, CCDC141, GP5, ZBTB32, CD79A, CCDC65, CSF2, DUSP8, RASGRP2, IL2, LPAR6, TTC16, NUGGC, TBX21, IL23A, NR3C2, C3AR1, C1orf228, LAG3, SLC16A10, NR4A2, MAL, C17orf107, CSF2RB, CCR2, GPR15, CD248, AMY2B, ASB2, LY9, PPP2R2B, ZDHHC14, DOK5, MT1G, CCR5, GCNT4, VSIG1, CFP, PLXDC1, ZBED2, ATP8B4, KLRD1, ZG16B, and MAF.

5. The method of claim 3, wherein the one or more genes associated with T-cell status comprise at least one gene selected from the group consisting of CFH, BAIAP3, MMP25, TENM1, PLEKHB1, MCM10, RASGRP2, PTPN3, TRIB2, ACTN1, ADD2, CST7, TP73, BIRC5, ITGA6, PCSK5, CACNA1I, CSF2RB, ASB2, DOK5, VSIG1, SYP, CTSH, TNFRSF10A, EBI3, CD79A, AEBP1, ACTA2, IL2, IL23A, IFNG, SASH1, ARFGEF3, SLC16A10, KIF20A, STC2, VIPR1, IGFBP2, EPHA4, CAMSAP2, NRP2, DUSP1, LY9, MT1G, PKMYT1, LIF, RAP1GAP2, ARHGEF11, CABLES1, KLRD1, PRR5L, SYTL2, CYP1B1, MYOF, CEP55, USO1, LPAR6, MYO1F, CDC42BPA, EPHA1, CHMP7, NTRK2, CRIM1, NR3C2, JAKMIP1, NR4A2, AK5, GPR15, PPP2R2B, KIT, DGKI, AUTS2, B4GALT5, ACE, CCR5, PLXDC1, ZG16B, AK4, NFIA, ATF3, CCDC141, CDC25A, ITGA2, CSF2, TMEM200A, AQP3, MELK, RRAD, C15orf48, TTC16, LAIR2, ANGPTL4, IL7R, NSG1, PTK2, ITGAM, NPAS2, CAVIN3, C3AR1, MAL, RAB37, NBEA, CD248, ZDHHC14, ZBED2, MAF, FUT7, FCRL6, AMIGOI, ANXA2, DENND5A, DUSP8, MYBL1, KIF18B, BCL2L15, NUGGC, PLXNB2, MAML3, RASGEF1A, CR1, TCEA3, SMIM26, HIST2H4B, CCL5, and HNF1B.

6. The method of claim 3, wherein the one or more genes associated with T-cell status comprise at least one gene selected from the group consisting of LEF1, NR4A2, CD248, DUSP8, EBI3, IL2, IL23A, TBX21, LAG3, CSF2, ASB2, CSF2RB, CCR2, KLRD1, MAF, CCR5, LY9, GCNT4, and VSIG1.

7. The method of claim 1, wherein the deconvolution algorithm applies a deconvolution matrix to the RNA sequencing data to quantify the T-cells having a particular status.

8. The method of claim 7, wherein the deconvolution matrix comprises a plurality of genes associated with T-cell status.

9. The method of claim 1, wherein the one or more genes associated with T-cell status comprise at least 10 genes.

10. The method of claim 1, wherein the immune checkpoint inhibitor comprises an anti-PD-1 or anti-PD-L1 antibody or antigen binding fragment.

11. The method of claim 1, wherein the immune checkpoint inhibitor comprises Enoblituzumab, Ipilimumab, Tremelimumab, Lirilumab, BMS986016, Pembrolizumab, Nivolumab, Pidilizumab, Atezolizumab, BMS-936559, Durvalumab, Avelumab, Bavituximab, or a combination thereof.

12. A method for treating a subject, the method comprising:
(a) administering an immunotherapy regimen to a subject in need thereof, wherein the immunotherapy regimen comprises an immune checkpoint inhibitor;
(b) obtaining a sample from the subject, wherein the sample comprises a plurality of cells;
(c) identifying a cell status of the plurality of cells, wherein identifying comprises:
(i) generating RNA sequencing data from the sample, the RNA sequencing data comprising expression levels of one or more genes associated with T-cell status; and
(ii) applying a deconvolution algorithm to at least a subset of the RNA sequencing data to identify and quantify an amount or percentage of cells in the sample having one or more cell statuses based on expression levels of the one or more genes associated with T-cell status, wherein the one or more cell statuses comprises naïve status, activated status, activation recovered status, terminally exhausted status, progenitor exhausted stats, central memory status, effector memory status, stem cell memory status, or any combination thereof,
(d) determining that the immunotherapy regimen of (a) is ineffective based on the identity and quantity of the one or more cell statuses, and
(e) discontinuing the immunotherapy regimen of (a).

13. The method of claim 12, wherein the immunotherapy regimen further comprises an immune cell therapy, a cancer vaccine, a cytokine therapy, or any combination thereof.

14. The method of claim 13, wherein the immune cell therapy is chimeric antigen receptor T-cell (CAR-T) therapy, tumor-infiltrating lymphocyte (TIL) therapy, engineered T-cell receptor (TCR) therapy, or natural killer (NK) cell therapy.

15. The method of claim 12, wherein determining if the immunotherapy regimen is effective based on the identity and quantity of the one or more cell statuses comprises comparing the quantity of cells having a particular cell status to a predetermined threshold for the particular cell status.

16. The method of claim 12, wherein the cells in the sample comprise CD4+ cells, CD8+ cells, Natural Killer T-Cells (NKT), or any combination thereof.

17. The method of claim 12, wherein the one or more genes associated with T-cell status comprise at least one gene selected from the group consisting of CFH, BAIAP3, MMP25, TENM1, PLEKHB1, MCM10, RASGRP2, PTPN3, TRIB2, ACTN1, ADD2, CST7, TP73, BIRC5, ITGA6, PCSK5, CACNA1I, CSF2RB, ASB2, DOK5, VSIG1, SYP, CTSH, TNFRSF10A, EBI3, CD79A, AEBP1, ACTA2, IL2, IL23A, IFNG, SASH1, ARFGEF3, SLC16A10, KIF20A, STC2, VIPR1, IGFBP2, EPHA4, CAMSAP2, NRP2, DUSP1, LY9, MT1G, PKMYT1, LIF, RAP1GAP2, ARHGEF11, CABLES1, KLRD1, PRR5L, SYTL2, CYP1B1, MYOF, CEP55, USO1, LPAR6, MYO1F, CDC42BPA, EPHA1, CHMP7, NTRK2, CRIM1, NR3C2, JAKMIP1, NR4A2, AK5, GPR15, PPP2R2B, KIT, DGKI, AUTS2, B4GALT5, ACE, CCR5, PLXDC1, ZG16B, AK4, NFIA, ATF3, CCDC141, CDC25A, ITGA2, CSF2, TMEM200A, AQP3, MELK, RRAD, C15orf48, TTC16, LAIR2, ANGPTL4, IL7R, NSG1, PTK2, ITGAM, NPAS2, CAVIN3, C3AR1, MAL, RAB37, NBEA, CD248, ZDHHC14, ZBED2, MAF, FUT7, FCRL6, AMIGO1, ANXA2, DENND5A, DUSP8, MYBL1, KIF18B, BCL2L15, NUGGC, PLXNB2, MAML3, RASGEFIA, CR1, TCEA3, SMIM26, HIST2H4B, CCL5, HNF1B, AMY2B, ATP8B4, C17orf107, C1orf228, CCDC65, CCR2, CFP, GCNT4, GP5, LAG3, LEF1, TBX21, and ZBTB32.

18. The method of claim 17, wherein the one or more genes associated with T-cell status comprise at least one gene selected from the group consisting of MMP25, EBI3, LEF1, CCDC141, GP5, ZBTB32, CD79A, CCDC65, CSF2, DUSP8, RASGRP2, IL2, LPAR6, TTC16, NUGGC, TBX21, IL23A, NR3C2, C3AR1, C1orf228, LAG3, SLC16A10, NR4A2, MAL, C17orf107, CSF2RB, CCR2, GPR15, CD248, AMY2B, ASB2, LY9, PPP2R2B, ZDHHC14, DOK5, MT1G, CCR5, GCNT4, VSIG1, CFP, PLXDC1, ZBED2, ATP8B4, KLRD1, ZG16B, and MAF.

19. The method of claim 17, wherein the one or more genes associated with T-cell status comprise at least one gene selected from the group consisting of CFH, BAIAP3, MMP25, TENM1, PLEKHB1, MCM10, RASGRP2, PTPN3, TRIB2, ACTN1, ADD2, CST7, TP73, BIRC5, ITGA6, PCSK5, CACNA1I, CSF2RB, ASB2, DOK5, VSIG1, SYP, CTSH, TNFRSF10A, EBI3, CD79A, AEBP1, ACTA2, IL2, IL23A, IFNG, SASH1, ARFGEF3, SLC16A10, KIF20A, STC2, VIPR1, IGFBP2, EPHA4, CAMSAP2, NRP2, DUSP1, LY9, MTIG, PKMYT1, LIF, RAP1GAP2, ARHGEF11, CABLES1, KLRD1, PRR5L, SYTL2, CYP1B1, MYOF, CEP55, USO1, LPAR6, MYO1F, CDC42BPA, EPHA1, CHMP7, NTRK2, CRIM1, NR3C2, JAKMIP1, NR4A2, AK5, GPR15, PPP2R2B, KIT, DGKI, AUTS2, B4GALT5, ACE, CCR5, PLXDC1, ZG16B, AK4, NFIA, ATF3, CCDC141, CDC25A, ITGA2, CSF2, TMEM200A, AQP3, MELK, RRAD, C15orf48, TTC16, LAIR2, ANGPTL4, IL7R, NSG1, PTK2, ITGAM, NPAS2, CAVIN3, C3AR1, MAL, RAB37, NBEA, CD248, ZDHHC14, ZBED2, MAF, FUT7, FCRL6, AMIGOI, ANXA2, DENND5A, DUSP8, MYBL1, KIF18B, BCL2L15, NUGGC, PLXNB2, MAML3, RASGEF1A, CR1, TCEA3, SMIM26, HIST2H4B, CCL5, and HNF1B.

20. The method of claim 12, wherein the one or more genes associated with T-cell status comprise at least one gene selected from the group consisting of LEF1, NR4A2, CD248, DUSP8, EB13, IL2, IL23A, TBX21, LAG3, CSF2, ASB2, CSF2RB, CCR2, KLRD1, MAF, CCR5, LY9, GCNT4, and VSIG1.

21. The method of claim 12, wherein the one or more genes associated with T-cell status comprise at least 10 genes.

22. A method for treating a subject, the method comprising:
   (a) administering an immunotherapy regimen to a subject in need thereof, wherein the immunotherapy regimen comprises chimeric antigen receptor T-cell (CAR-T) therapy,
   (b) obtaining a sample from the subject;
   (c) sending the sample for analysis of cell status, wherein the analysis of cell status comprises:
      (i) generating RNA sequencing data from the sample, the RNA sequencing data comprising expression levels of one or more genes associated with T-cell status; and
      (ii) applying a deconvolution algorithm to at least a subset of the RNA sequencing data to identify and quantify an amount or percentage of cells in the sample having one or more cell statuses based on expression levels of the one or more genes associated with T-cell status, wherein the one or more cell statuses comprises naïve status, activated status, activation recovered status, terminally exhausted status, progenitor exhausted stats, central memory status, effector memory status, stem cell memory status, or any combination thereof,
   (d) determining if the immunotherapy regimen is effective based on the identity and quantity of the one or more cell statuses, wherein the immunotherapy regimen is continued or discontinued based at least on the determination of effectiveness, wherein the chimeric antigen receptor T-cell (CAR-T) therapy comprises axicabtagene ciloleucel or tisagenlecleucel.

* * * * *